(12) United States Patent
Wallace et al.

(10) Patent No.: US 7,576,072 B2
(45) Date of Patent: Aug. 18, 2009

(54) HETEROCYCLIC INHIBITORS OF MEK AND METHODS OF USE THEREOF

(75) Inventors: Eli Wallace, Lyons, CO (US); Jeongbeob Seo, Broomfield, CO (US); Joseph P. Lyssikatos, Superior, CO (US); Hong Woon Yang, Superior, CO (US); T. Brian Hurley, Boulder, CO (US); Allison L. Marlow, Louisville, CO (US); James Blake, Longmont, CO (US)

(73) Assignee: Array BioPharma Inc., Boulder, CO (US)

( * ) Notice: Subject to any disclaimer, the term of this patent is extended or adjusted under 35 U.S.C. 154(b) by 815 days.

(21) Appl. No.: 10/992,479

(22) Filed: Nov. 18, 2004

(65) Prior Publication Data

US 2005/0153942 A1  Jul. 14, 2005

Related U.S. Application Data

(60) Provisional application No. 60/523,270, filed on Nov. 19, 2003.

(51) Int. Cl.
*A61K 31/655* (2006.01)
*C07D 471/02* (2006.01)

(52) U.S. Cl. .................. 514/151; 514/301; 514/302; 514/303; 546/114; 546/115; 546/117

(58) Field of Classification Search .................. 514/151, 514/301, 302, 303; 546/114, 115, 117
See application file for complete search history.

(56) References Cited

U.S. PATENT DOCUMENTS

| | | | |
|---|---|---|---|
| 5,231,094 A | 7/1993 | Bru-Magniez et al. | |
| 5,525,625 A | 6/1996 | Bridges et al. | |
| 6,310,060 B1 | 10/2001 | Barrett et al. | |
| 6,469,004 B1 | 10/2002 | Barrett et al. | |
| 6,506,798 B1 | 1/2003 | Barrett et al. | |
| 2003/0004193 A1 | 1/2003 | Barrett et al. | |
| 2003/0045521 A1 | 3/2003 | Tecle | |
| 2003/0078428 A1 | 4/2003 | Barrett et al. | |
| 2003/0092748 A1 | 5/2003 | Barrett et al. | |
| 2003/0195183 A1 | 10/2003 | Zhilov | |
| 2003/0216460 A1 | 11/2003 | Wallace et al. | |
| 2003/0232869 A1 | 12/2003 | Wallace et al. | |
| 2004/0116710 A1 | 6/2004 | Wallace et al. | |

FOREIGN PATENT DOCUMENTS

| | | |
|---|---|---|
| WO | WO 95/03286 A1 | 2/1995 |
| WO | WO 98/43960 A1 | 10/1998 |
| WO | WO 99/01421 A1 | 1/1999 |
| WO | WO 99/01426 A1 | 1/1999 |
| WO | WO 00/40235 A2 | 7/2000 |
| WO | WO 00/40237 A1 | 7/2000 |
| WO | WO 00/41505 A2 | 7/2000 |
| WO | WO 00/41994 A1 | 7/2000 |
| WO | WO 00/42002 A1 | 7/2000 |
| WO | WO 00/42003 A1 | 7/2000 |
| WO | WO 00/42022 A1 | 7/2000 |
| WO | WO 00/42029 A1 | 7/2000 |
| WO | WO 00/68201 A1 | 11/2000 |
| WO | WO 01/05390 A2 | 1/2001 |
| WO | WO 01/05391 A2 | 1/2001 |
| WO | WO 01/05392 A2 | 1/2001 |
| WO | WO 01/05393 A2 | 1/2001 |
| WO | WO 01/68619 A1 | 9/2001 |
| WO | WO 02/06213 A2 | 1/2002 |
| WO | WO 02/18319 A1 | 3/2002 |
| WO | WO 02/44166 A1 | 6/2002 |
| WO | WO 03/077855 A2 | 9/2003 |
| WO | WO 03/077914 A1 | 9/2003 |

OTHER PUBLICATIONS

Mc Viaud et al., Acylation of Oxazolo[4,5-b] Pyridin-2(3H)-Ones, 2-Phenyloxazolo[4,5-b] Pyridines and Pyrrolo[2,3-b] Pyridin-2(2-H)-Ones, Tetrahedron, vol. 53, No. 14, pp. 5159-5168, 1997. Published by Elsevier Science Ltd.
Moreau, S et al., Synthesis and Anticonvulsant Properties of Triazolo- and Imidazopyridazinyl Carboxamides and Carboxylic Acids, Bioorganic & Medicinal Chemistry 6 (1998) 983-991.
PCT/US04/39053 International Search Report (Sep. 16, 2005).
Bachman "Further Studies of Aminobenzacridines"; Journal of Organic Chemistry; 1948; pp. 89-96; vol. 13.

*Primary Examiner*—James O. Wilson
*Assistant Examiner*—Ebenezer Sackey
(74) *Attorney, Agent, or Firm*—John R. Moore; Hogan & Hartson LLP

(57) ABSTRACT

Disclosed are compounds of the Formula I

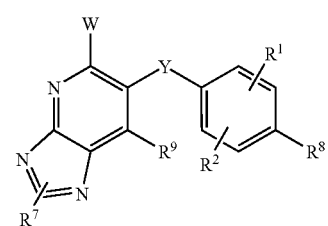

and pharmaceutically acceptable salts and prodrugs thereof, wherein $R^1$, $R^2$, $R^7$, $R^8$ and $R^9$, W, X, Y and Z are as defined in the specification. Such compounds are MEK inhibitors and are useful in the treatment of hyperproliferative diseases, such as cancer and inflammation, in mammals, and inflammatory conditions. Also disclosed are methods of using such compounds in the treatment of hyperproliferative diseases in mammals and pharmaceutical compositions containing such compounds.

18 Claims, 21 Drawing Sheets

HETEROCYCLIC INHIBITORS OF MEK AND METHODS OF USE THEREOF

CROSS-REFERENCE TO RELATED APPLICATIONS

This application claims the benefit of U.S. Provisional Application Ser. No. 60/523,270, filed Nov. 19, 2003, which is incorporated herein in its entirety by reference.

BACKGROUND OF THE INVENTION

1. Field of the Invention

This invention relates to a series of novel heterocyclic compounds that are useful in the treatment of hyperproliferative diseases, such as cancer and inflammation, in mammals. This invention also relates to a method of using such compounds in the treatment of hyperproliferative diseases in mammals, especially humans, and to pharmaceutical compositions containing such compounds.

2. Description of the State of the Art

Cell signaling through growth factor receptors and protein kinases is an important regulator of cell growth, proliferation and differentiation. In normal cell growth, growth factors, through receptor activation (i.e. PDGF or EGF and others), activate MAP kinase pathways. One of the most important and most well understood MAP kinase pathways involved in normal and uncontrolled cell growth is the Ras/Raf kinase pathway. Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al, *Methods in Enzymology*, 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., *Methods in Enzymology*, 2001, 332, 417-431). Phosphorylated ERK dimerizes and then translocates to the nucleus where it accumulates (Khokhlatchev et al., *Cell*, 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell*, 2000, 6, 1343-1354). Overall, treatment of cells with growth factors leads to the activation of ERK1 and 2 which results in proliferation and, in some cases, differentiation (Lewis et al., *Adv. Cancer Res.*, 1998, 74, 49-139).

In proliferative diseases, genetic mutations and/or overexpression of the growth factor receptors, downstream signaling proteins, or protein kinases involved in the ERK kinase pathway lead to uncontrolled cell proliferation and, eventually, tumor formation. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science*, 1993, 260, 1834-1837). Recently, bRaf mutations have been identified in more than 60% of malignant melanoma (Davies, H. et al., *Nature*, 2002, 417, 949-954). These mutations in bRaf result in a constitutively active MAP kinase cascade. Studies of primary tumor samples and cell lines have also shown constitutive or overactivation of the MAP kinase pathway in cancers of pancreas, colon, lung, ovary and kidney (Hoshino, R. et al., *Oncogene*, 1999, 18, 813-822). Hence, there is a strong correlation between cancers and an overactive MAP kinase pathway resulting from genetic mutations.

As constitutive or overactivation of MAP kinase cascade plays a pivotal role in cell proliferation and differentiation, inhibition of this pathway is believed to be beneficial in hyperproliferative diseases. MEK is a key player in this pathway as it is downstream of Ras and Raf. Additionally, it is an attractive therapeutic target because the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al., *Nature-Medicine*, 1999, 5 (7), 810-816; Trachet et al., AACR Apr. 6-10, 2002, Poster #5426; Tecle, H., IBC 2nd International Conference of Protein Kinases, Sep. 9-10, 2002), block static allodynia in animals (WO 01/05390 published Jan. 25, 2001) and inhibit growth of acute myeloid leukemia cells (Milella et al., *J. Clin. Invest.*, 2001, 108 (6), 851-859).

Small molecule inhibitors of MEK have been disclosed, including in U.S. Patent Publication Nos. 2003/0232869, 2004/0116710, and 2003/0216460, and U.S. patent application Ser. Nos. 10/654,580 and 10/929,295, each of which is hereby incorporated by reference. At least fifteen additional patent applications have appeared in the last several years. See, for example: U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; WO 02/06213; WO 03/077914; and WO 03/077855.

SUMMARY OF THE INVENTION

This invention provides for novel heterocyclic compounds, and pharmaceutically acceptable salts and prodrugs thereof that are useful in the treatment of hyperproliferative diseases. Specifically, one aspect the present invention relates to compounds of Formulas I-V that act as MEK inhibitors.

More specifically, one embodiment of the present invention provides compounds of the Formulas I-V:

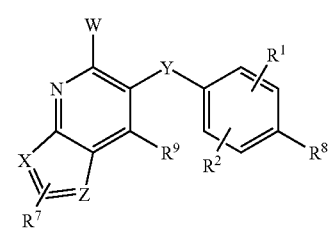

I

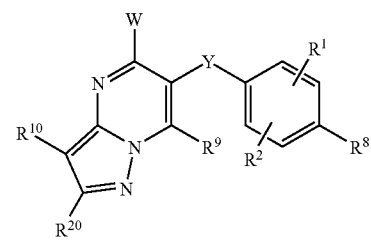

II

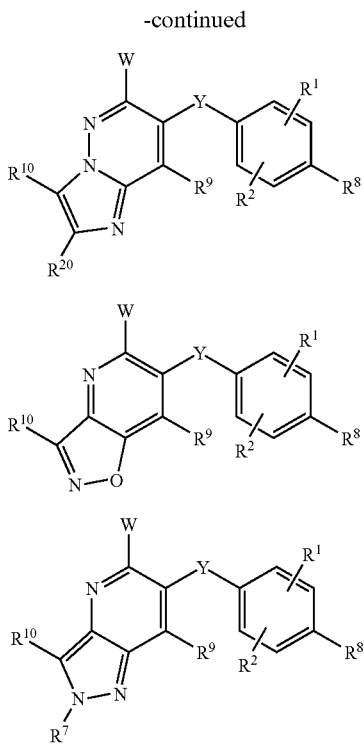

and pharmaceutically accepted salts, prodrugs and solvates thereof, wherein:

X is C or N;

Y is $NR^{15}$, O, S, S(O), S(O)$_2$, C(O) or CH$_2$;

Z is C or N;

$R^1$, $R^2$, $R^8$, $R^9$, $R^{10}$ and $R^{20}$ are independently hydrogen, hydroxy, halogen, cyano, nitro, trifluoromethyl, difluoromethyl, fluoromethyl, fluoromethoxy, difluoromethoxy, trifluoromethoxy, azido, —SR$^{11}$, —OR$^3$, —C(O)R$^3$, —C(O)OR$^3$, —NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^5$C(NCN)NR$^3$R$^4$, —NR$^3$R$^4$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, —S(O)$_j$(C$_1$-C$_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethoxy, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

$R^7$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, C$_1$-C$_{10}$ alkyl, C$_2$-C$_{10}$ alkenyl, C$_2$-C$_{10}$ alkynyl, C$_3$-C$_{10}$ cycloalkyl, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

$R^3$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN) NR$^{12}$R$^{13}$, —OR$^{11}$, aryl, heteroaryl, arylalkyl, heteroarylalkyl, heterocyclyl, and heterocyclylalkyl;

or $R^3$ and $R^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN) NR$^{12}$R$^{13}$, —OR$^{11}$, aryl, heteroaryl, arylalkyl, heteroarylalkyl, heterocyclyl, and heterocyclylalkyl;

$R^4$ and $R^5$ independently are hydrogen or C$_1$-C$_6$ alkyl, or $R^4$ and $R^5$ together with the atom to which they are attached form a 4 to 10 membered carbocyclic, heteroaryl or heterocyclic ring, wherein said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O) R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN) NR$^{12}$R$^{13}$, —OR$^{11}$, aryl, heteroaryl, arylalkyl, heteroarylalkyl, heterocyclyl, and heterocyclylalkyl;

$R^6$ is trifluoromethyl, C$_1$-C$_{10}$ alkyl, C$_3$-C$_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, $-NR^{11}SO_2R^{14}$, $-SO_2NR^{11}R^{12}$, $-C(O)R^{11}$, $C(O)OR^{11}$, $-OC(O)R^{11}$, $-NR^{11}C(O)OR^{14}$, $-NR^{11}C(O)R^{12}$, $-C(O)NR^{11}R^{12}$, $-SR^{11}$, $-S(O)R^{14}$, $-SO_2R^{14}$, $-NR^{11}R^{12}$, $-NR^{11}C(O)NR^{12}R^{13}$, $-NR^{11}C(NCN)NR^{12}R^{13}$, $OR^{11}$, aryl, heteroaryl, arylalkyl, heteroarylalkyl, heterocyclyl, and heterocyclylalkyl;

$R^{11}$, $R^{12}$ and $R^{13}$ independently are hydrogen, lower alkyl, lower alkenyl, aryl or arylalkyl, and $R^{14}$ is lower alkyl, lower alkenyl, aryl or arylalkyl;

or any two of $R^{11}$, $R^{12}$, $R^{13}$ or $R^{14}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

W is heteroaryl, heterocyclyl, $-C(O)OR^3$, $-C(O)NR^3R^4$, $-C(O)NR^4OR^3$, $-C(O)R^4OR^3$, $-C(O)NR^4SO_2R^3$, $-C(O)(C_3-C_{10}$ cycloalkyl), $-C(O)(C_1-C_{10}$ alkyl), $-C(O)(aryl)$, $-C(O)(heteroaryl)$, $-C(O)(heterocyclyl)$ or $CR^3OR^3$, wherein any of said heteroaryl, heterocyclyl, $-C(O)OR^3$, $-C(O)NR^3R^4$, $-C(O)NR^4OR^3$, $-C(O)R^4OR^3$, $-C(O)NR^4SO_2R^3$, $-C(O)(C_3-C_{10}$ cycloalkyl), $-C(O)(C_1-C_{10}$ alkyl), $-C(O)(aryl)$, $-C(O)(heteroaryl)$, $-C(O)(heterocyclyl)$ and $CR^3OR^3$ are optionally substituted with one or more groups independently selected from halogen, cyano, nitro, azido, $-NR^3R^4$, $-OR^3$, $C_1-C_{10}$ alkyl, $C_2-C_{10}$ alkenyl, $C_2-C_{10}$ alkynyl, cycloalkyl and heterocloalkyl, wherein any of said $C_1-C_{10}$ alkyl, $C_2-C_{10}$ alkenyl, $C_2-C_{10}$ alkynyl, cycloalkyl and heterocycloalkyl are optionally substituted with 1 or more groups independently selected from $-NR^3R^4$ and $-OR^3$;

$R^{15}$ is hydrogen, halogen, methyl, fluoromethyl, difluoromethyl, trifluoromethyl or ethyl;

m is 0, 1, 2, 3, 4 or 5; and j is 0, 1 or 2.

In a further aspect the present invention provides compositions that inhibit MEK comprising compounds of Formulas I-V.

The invention is also directed to pharmaceutically acceptable prodrugs, pharmaceutically active metabolites, and pharmaceutically acceptable salts of compounds of Formula I-V. Methods of making the compounds of Formula I-V are also described.

In a further aspect the present invention provides a method of using the compounds of this invention to treat diseases or medical conditions mediated by MEK, such as cancer. For example, this invention provides a method for treatment of a hyperproliferative disorder or an inflammatory condition in a mammal comprising administrating to said mammal one or more compounds of Formulas I-V or a pharmaceutically acceptable salt or prodrug thereof in an amount effective to treat said hyperproliferative disorder.

In a further aspect the present invention provides methods for treating or preventing an MEK-mediated condition, comprising administering to a human or animal in need thereof a pharmaceutical composition comprising a compound of Formula I-V, or a pharmaceutically-acceptable salt or in vivo cleavable prodrug thereof, in an amount effective to treat or prevent said MEK-mediated condition.

The inventive compounds may further be used advantageously in combination with other known therapeutic agents.

Yet another embodiment of the present invention provides pharmaceutical compositions comprising an effective amount of an agent selected from compounds of Formulas I-V or a pharmaceutically acceptable prodrug, pharmaceutically active metabolite, or pharmaceutically acceptable salt thereof.

An additional aspect of the invention is the use of a compound of Formula I, Formula II, Formula III, Formula IV or Formula V in the preparation of a medicament for the treatment or prevention of a disease or medical condition mediated by MEK in a warm-blooded animal, preferably a mammal, more preferably a human, suffering from such disorder. More particularly, the invention includes the use of a compound of the invention in the preparation of a medicament for the treatment or prevention of a hyperproliferative disorder or an inflammatory condition in a mammal.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
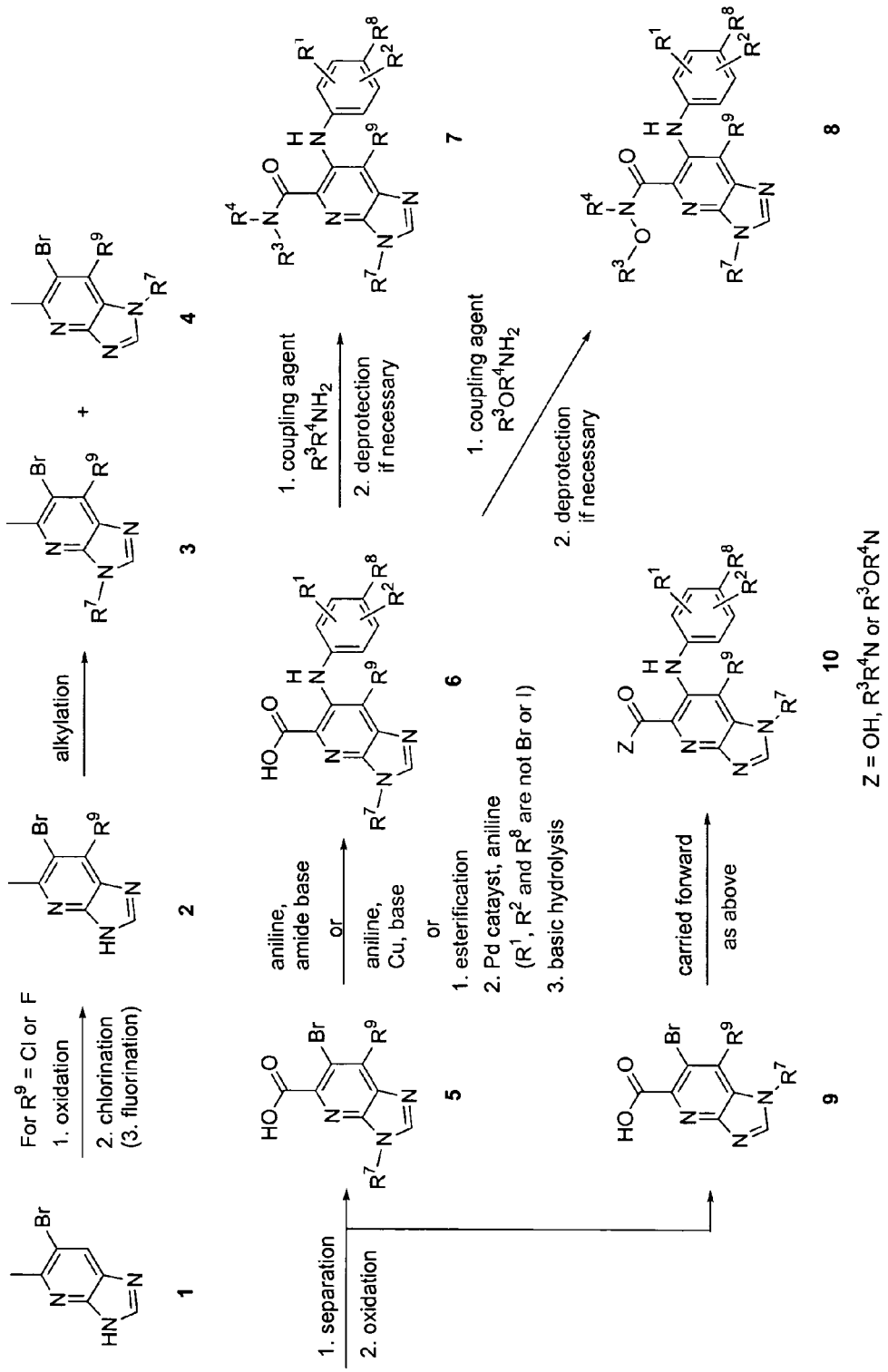
FIG. 1 shows a reaction scheme for the synthesis of compounds 6-8 and 10.

The inventive compounds of the Formulas I-V and the pharmaceutically acceptable salts and prodrugs thereof of this invention are useful in the treatment of hyperproliferative diseases. Specifically, one aspect the present invention relates to compounds of Formula I-V that act as MEK inhibitors. More specifically, one embodiment of the invention provides compounds, including pharmaceutically acceptable salts, prodrugs and solvates thereof, having the general Formula I:

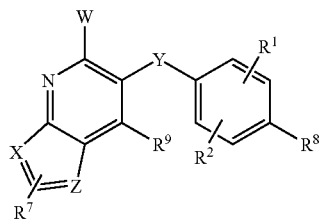

I and pharmaceutically acceptable salts, prodrugs and solvates thereof, where:

X is C or N;

Y is $NR^{15}$, O, S, S(O), S(O)$_2$, C(O) or CH$_2$;

Z is C or N;

$R^1$, $R^2$, $R^8$, and $R^9$ are independently hydrogen, hydroxy, halogen, cyano, nitro, trifluoromethyl, difluoromethyl, fluoromethyl, fluoromethoxy, difluoromethoxy, trifluoromethoxy, azido, —SR$^{11}$, —OR$^3$, —C(O)R$^3$, —C(O)OR$^3$, —NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^5$C(NCN)NR$^3$R$^4$, —NR$^3$R$^4$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, —S(O)$_j$(C$_1$-C$_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O) NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

$R^7$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, C$_1$-C$_{10}$ alkyl, C$_2$-C$_{10}$ alkenyl, C$_2$-C$_{10}$ alkynyl, C$_3$-C$_{10}$ cycloalkyl, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

$R^3$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O) R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN) NR$^{11}$R$^{12}$, —OR$^{11}$, aryl, heteroaryl, arylalkyl, heteroarylalkyl, heterocyclyl, and heterocyclylalkyl;

or $R^3$ and $R^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O) OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$; —NR$^{11}$R$^{12}$, —NR$^{11}$C(O)NR$^{12}$R$^{13}$, —NR$^{11}$C(NCN) NR$^{12}$R$^{13}$, —OR$^{11}$, aryl, heteroaryl, arylalkyl, heteroarylalkyl, heterocyclyl, and heterocyclylalkyl;

$R^4$ and $R^5$ independently are hydrogen or C$_1$-C$_6$ alkyl, or $R^4$ and $R^5$ together with the atom to which they are attached form a 4 to 10 membered carbocyclic, heteroaryl or heterocyclic ring, wherein said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^6$ is trifluoromethyl, C$_1$-C$_{10}$ alkyl, C$_3$-C$_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{14}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^{11}$, R$^{12}$ and R$^{13}$ independently are hydrogen, lower alkyl, lower alkenyl, aryl or arylalkyl, and R$^{14}$ is lower alkyl, lower alkenyl, aryl or arylalkyl;

or any two of R$^{11}$, R$^{12}$, R$^{13}$ or R$^{14}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) or CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) and CR$^3$OR$^3$ are optionally substituted with one or more groups independently selected from halogen, cyano, nitro, azido, —NR$^3$R$^4$, —OR$^3$, C$_1$-C$_{10}$ alkyl, C$_2$-C$_{10}$ alkenyl, C$_2$-C$_{10}$ alkynyl, cycloalkyl and heterocycloalkyl, wherein any of said C$_1$-C$_{10}$ alkyl, C$_2$-C$_{10}$ alkenyl, C$_2$-C$_{10}$ alkynyl, cycloalkyl and heterocycloalkyl are optionally substituted with 1 or more groups independently selected from —NR$^3$R$^4$ and —OR$^3$;

R$^{15}$ is hydrogen, halogen, methyl, fluoromethyl, difluoromethyl, trifluoromethyl or ethyl;

m is 0, 1, 2, 3, 4 or 5; and j is 0, 1 or 2.

In one preferred embodiment, W is selected from

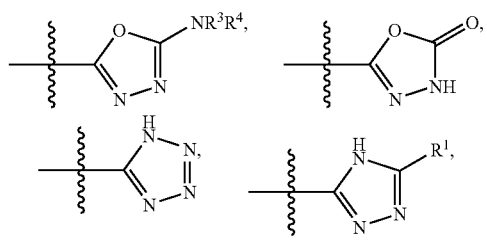

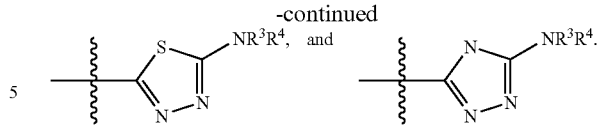

Figure 2:
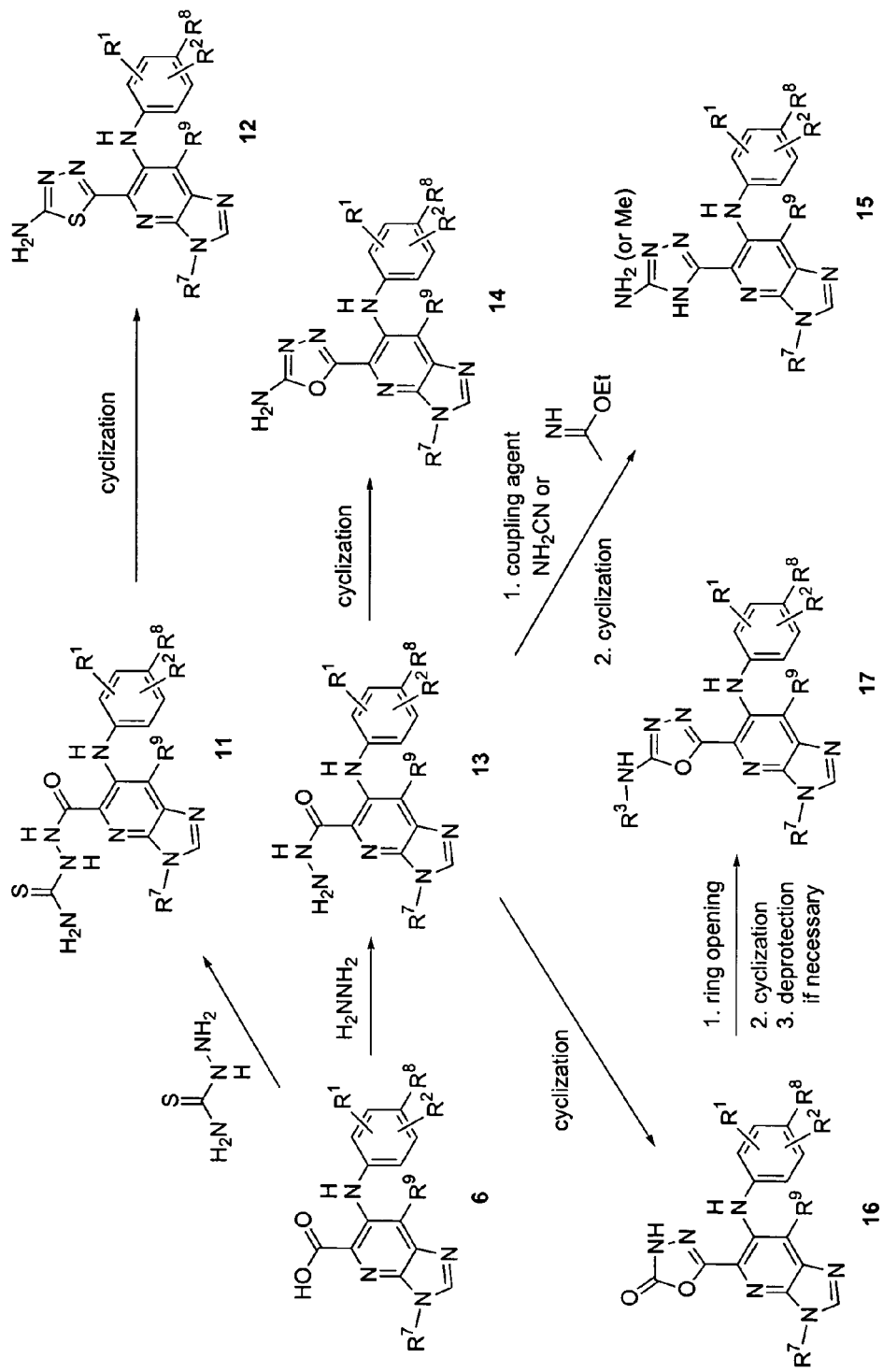
FIG. 2 shows a reaction scheme for the synthesis of compounds 11-17.

FIGS. 1-2 show non-limiting examples of the synthesis of compounds of this invention having the general Formula I.

In addition to compounds of the general Formula I, this invention further includes compounds of the general Formula II:

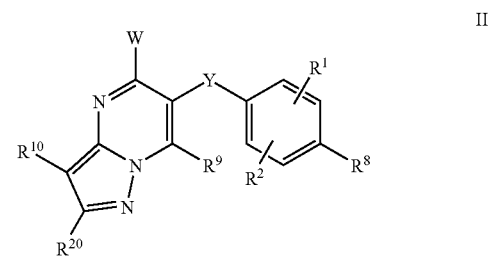

and pharmaceutically accepted salts, prodrugs and solvates thereof, where:

Y is NR$^{15}$, O, S, S(O), S(O)$_2$, C(O) or CH$_2$;

R$^1$, R$^2$, R$^8$, R$^9$, R$^{10}$ and R$^{20}$ are independently hydrogen, hydroxy, halogen, cyano, nitro, trifluoromethyl, difluoromethyl, fluoromethyl, fluoromethoxy, difluoromethoxy, trifluoromethoxy, azido, —SR$^{11}$, —OR$^3$, —C(O)R$^3$, —C(O)OR$^3$, —NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^5$C(NCN)NR$^3$R$^4$, —NR$^3$R$^4$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, —S(O)$_j$(C$_1$-C$_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

R$^3$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

or R$^3$ and R$^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^4$ and R$^5$ independently are hydrogen or C$_1$-C$_6$ alkyl, or

R$^4$ and R$^5$ together with the atom to which they are attached form a 4 to 10 membered carbocyclic, heteroaryl or heterocyclic ring, wherein said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R , —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^6$ is trifluoromethyl, C$_1$-C$_{10}$ alkyl, C$_3$-C$_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^{11}$, R$^{12}$ and R$^{13}$ independently are hydrogen, lower alkyl, lower alkenyl, aryl or arylalkyl, and R$^{14}$ is lower alkyl, lower alkenyl, aryl or arylalkyl;

or any two of R$^{11}$, R$^{12}$, R$^{13}$ or R$^{14}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) or CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) and CR$^3$OR$^3$ are optionally substituted with one or more groups independently selected from halogen, cyano, nitro, azido, —NR$^3$R$^4$, —OR$^3$, C$_1$-C$_{10}$ alkyl, C$_2$-C$_{10}$ alkenyl, C$_2$-C$_{10}$ alkynyl, cycloalkyl and heterocycloalkyl, wherein any of said C$_1$-C$_{10}$ alkyl, C$_2$-C$_{10}$ alkenyl, C$_2$-C$_{10}$ alkynyl, cycloalkyl and heterocycloalkyl are optionally substituted with 1 or more groups independently selected from —NR$^3$R$^4$ and —OR$^3$;

R$^{15}$ is hydrogen, halogen, methyl, fluoromethyl, difluoromethyl, trifluoromethyl or ethyl;

m is 0, 1, 2, 3, 4 or 5; and j is 0, 1 or 2.

Figure 3:
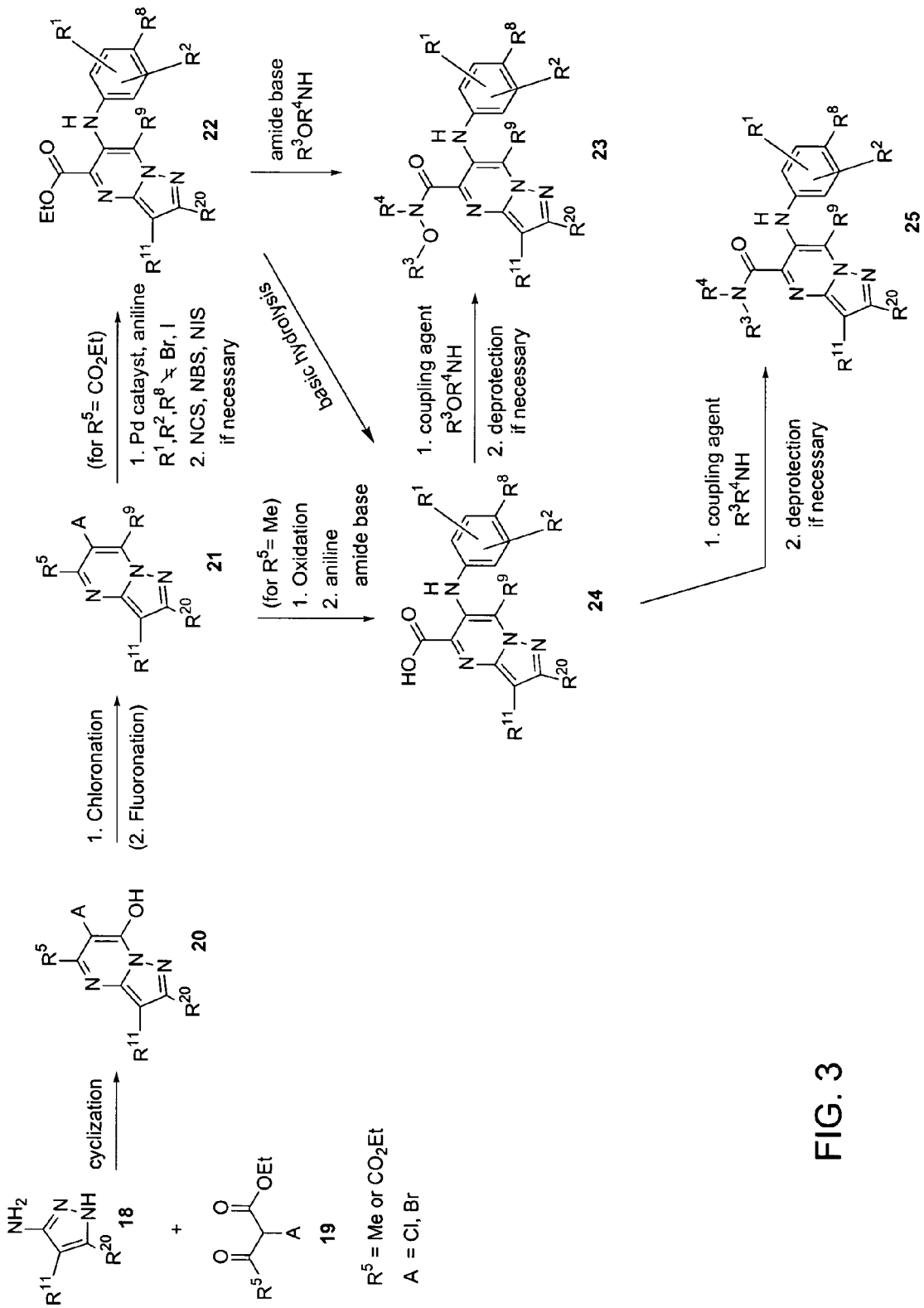
FIG. 3 shows a reaction scheme for the synthesis of compounds 22-25.
Figure 4:
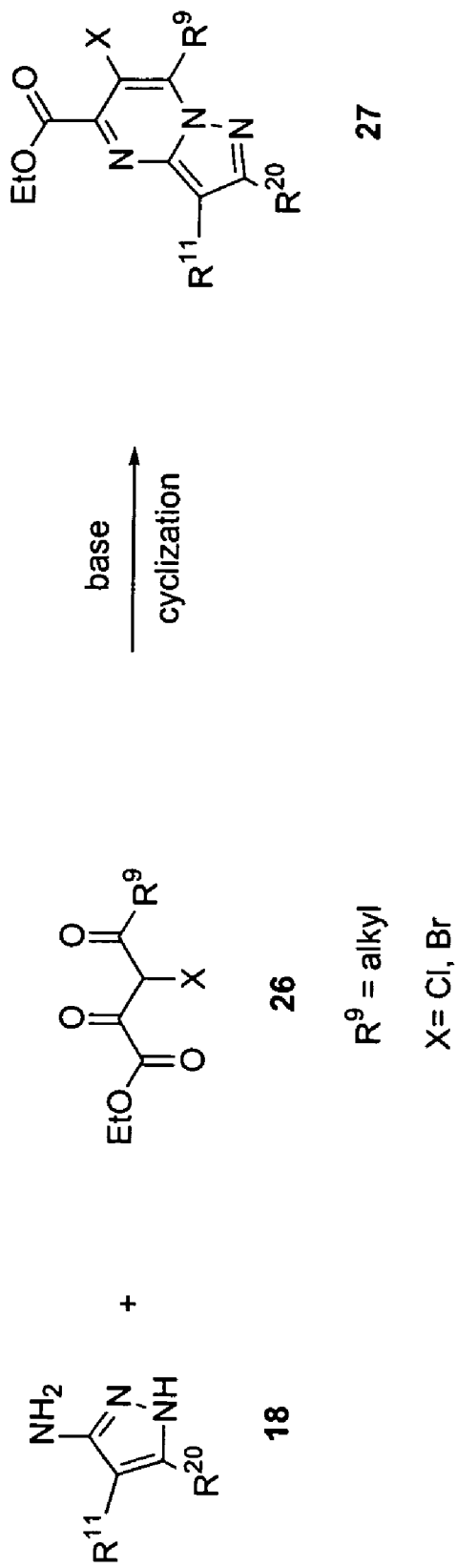
FIG. 4 shows a reaction scheme for the synthesis of compound 27.
Figure 5:
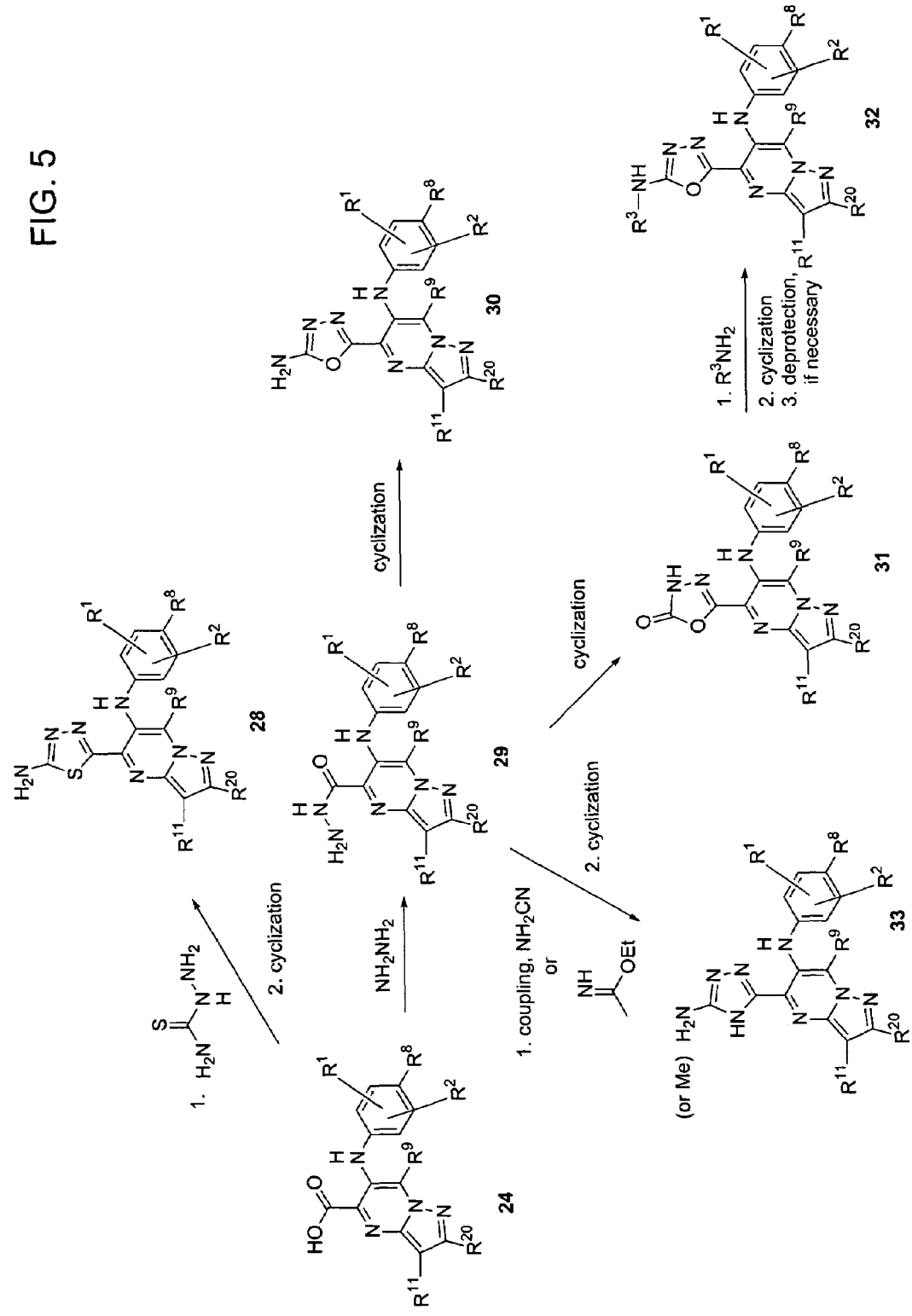
FIG. 5 shows a reaction scheme for the synthesis of compounds 28-33.

FIGS. 3-5 show non-limiting examples of the synthesis of compounds of this invention having the general Formula II.

In another embodiment, this invention relates to compounds of the general Formula III:

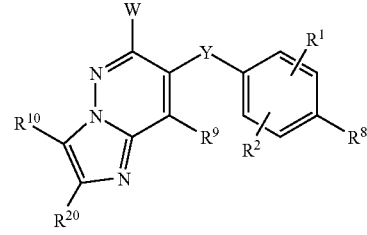

and pharmaceutically accepted salts, prodrugs and solvates thereof, where:

Y is NR$^{15}$, O, S, S(O), S(O)$_2$, C(O) or CH$_2$;

R$^1$, R$^2$, R$^8$, R$^9$, R$^{10}$ and R$^{20}$ are independently hydrogen, hydroxy, halogen, cyano, nitro, trifluoromethyl, difluoromethyl, fluoromethyl, fluoromethoxy, difluoromethoxy, trifluoromethoxy, azido, —SR$^{11}$, —OR$^3$, —C(O)R$^3$, —C(O)OR$^3$, —NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^5$C(NCN)NR$^3$R$^4$, —NR$^3$R$^4$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, —S(O)$_j$(C$_1$-C$_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

R$^3$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

or R$^3$ and R$^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^4$ and R$^5$ independently are hydrogen or C$_1$-C$_6$ alkyl, or

R$^4$ and R$^5$ together with the atom to which they are attached form a 4 to 10 membered carbocyclic, heteroaryl or heterocyclic ring, wherein said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^6$ is trifluoromethyl, C$_1$-C$_{10}$ alkyl, C$_3$-C$_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^{11}$, R$^{12}$ and R$^{13}$ independently are hydrogen, lower alkyl, lower alkenyl, aryl or arylalkyl, and R$^{14}$ is lower alkyl, lower alkenyl, aryl or arylalkyl;

or any two of R$^{11}$, R$^{12}$, R$^{13}$ or R$^{14}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) or CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) and CR$^3$OR$^3$ are optionally substituted with one or more groups independently selected from halogen, cyano, nitro, azido, —NR$^3$R$^4$, —OR$^3$, C$_1$-C$_{10}$ alkyl, C$_2$-C$_{10}$ alkenyl, C$_2$-C$_{10}$ alkynyl, cycloalkyl and heterocycloalkyl, wherein any of said C$_1$-C$_{10}$ alkyl, C$_2$-C$_{10}$ alkenyl, C$_2$-C$_{10}$ alkynyl, cycloalkyl and heterocycloalkyl are optionally substituted with 1 or more groups independently selected from —NR$^3$R$^4$ and —OR$^3$;

R$^{15}$ is hydrogen, halogen, methyl, fluoromethyl, difluoromethyl, trifluoromethyl or ethyl;

m is 0, 1, 2, 3, 4 or 5; and j is 0, 1 or 2.

FIGS. 6-18 show non-limiting examples of the synthesis of compounds of this invention having the general Formula III.

In another embodiment, this invention relates to compounds of the general Formula IV:

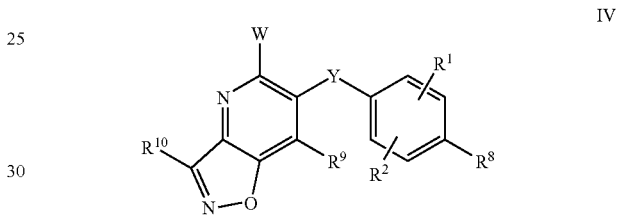

and pharmaceutically accepted salts, prodrugs and solvates thereof, where:

Y is NR$^{15}$, O, S, S(O), S(O)$_2$, C(O) or CH$_2$;

R$^1$, R$^2$, R$^8$, R$^9$ and R$^{10}$ are independently hydrogen, hydroxy, halogen, cyano, nitro, trifluoromethyl, difluoromethyl, fluoromethyl, fluoromethoxy, difluoromethoxy, trifluoromethoxy, azido, —SR$^{11}$, —OR$^3$, —C(O)R$^3$, —C(O)OR$^3$, —NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^5$C(NCN)NR$^3$R$^4$, —NR$^3$R$^4$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, —S(O)$_j$(C$_1$-C$_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, NR$^3$R$^4$ and OR$^3$;

R³ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —$NR^{11}SO_2R^{14}$, —$SO_2NR^{11}R^{12}$, —C(O)$R^{11}$, C(O)O$R^{11}$, —OC(O)$R^{11}$, —$NR^{11}$C(O)O$R^{14}$, —$NR^{11}$C(O)$R^{12}$, —C(O)$NR^{11}R$ , —$SR^{11}$, —S(O)$R^{14}$, —$SO_2R^{14}$, —$NR^{11}R^{12}$, —$NR^{11}$C(O)$NR^{12}R^{13}$, —$NR^{11}$C(NCN)$NR^{12}R^{13}$, —$OR^{11}$, aryl, heteroaryl, arylalkyl, heteroarylalkyl, heterocyclyl, and heterocyclylalkyl;

or R³ and R⁴ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —$NR^{11}SO_2R^{14}$, —$SO_2NR^{11}R^{12}$, —C(O)$R^{11}$, C(O)O$R^{11}$, —OC(O)$R^{11}$, —$NR^{11}$C(O)O$R^{14}$, —$NR^{11}$C(O)$R^{12}$, —C(O)$NR^{11}R^{12}$, —$SR^{11}$, —S(O)$R^{14}$, —$SO_2R^{14}$, —$NR^{11}R^{12}$, —$NR^{11}$C(O)$NR^{12}R^{13}$, —$NR^{11}$C(NCN)$NR^{12}R^{13}$, —$OR^{11}$, aryl, heteroaryl, arylalkyl, heteroarylalkyl, heterocyclyl, and heterocyclylalkyl;

R⁴ and R⁵ independently are hydrogen or $C_1$-$C_6$ alkyl, or

R⁴ and R⁵ together with the atom to which they are attached form a 4 to 10 membered carbocyclic, heteroaryl or heterocyclic ring, wherein said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —$NR^{11}SO_2R^{14}$, —$SO_2NR^{11}R^{12}$, —C(O)$R^{11}$, C(O)O$R^{11}$, —OC(O)$R^{11}$, —$NR^{11}$C(O)O$R^{14}$, —$NR^{11}$C(O)$R^{12}$, —C(O)$NR^{11}R^{12}$, —$SR^{11}$, —S(O)$R^{14}$, —$SO_2R^{14}$, —$NR^{11}R^{12}$, —$NR^{11}$C(O)$NR^{12}R^{13}$, —$NR^{11}$C(NCN)$NR^{12}R^{13}$, —$OR^{11}$, aryl, heteroaryl, arylalkyl, heteroarylalkyl, heterocyclyl, and heterocyclylalkyl;

R⁶ is trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —$NR^{11}SO_2R^{14}$, —$SO_2NR^{11}R^{12}$, —C(O)$R^{11}$, C(O)O$R^{11}$, —OC(O)$R^{11}$, —$NR^{11}$C(O)O$R^{14}$, —$NR^{11}$C(O)$R^{12}$, —C(O)$NR^{11}R^{12}$, —$SR^{11}$, —S(O)$R^{14}$, —$SO_2R^{14}$, —$NR^{11}R^{11}$, —$NR^{11}$C(O)$NR^{12}R^{13}$, —$NR^{11}$C(NCN)$NR^{12}R^{13}$, —$OR^{11}$, aryl, heteroaryl, arylalkyl, heteroarylalkyl, heterocyclyl, and heterocyclylalkyl;

$R^{11}$, $R^{12}$ and $R^{13}$ independently are hydrogen, lower alkyl, lower alkenyl, aryl or arylalkyl, and $R^{14}$ is lower alkyl, lower alkenyl, aryl or arylalkyl;

or any two of $R^{11}$, $R^{12}$, $R^{13}$ or $R^{14}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

W is heteroaryl, heterocyclyl, —C(O)O$R^3$, —C(O)$NR^3R^4$, —C(O)$NR^4OR^3$, —C(O)$R^4OR^3$, —C(O)$NR^4SO_2R^3$, —C(O)($C_3$-$C_{10}$ cycloalkyl), —C(O)($C_1$-$C_{10}$ alkyl), —C(O)(aryl), —C(O)(heteroaryl), —C(O)(heterocyclyl) or $CR^3OR^3$, wherein any of said heteroaryl, heterocyclyl, —C(O)O$R^3$, —C(O)$NR^3R^4$, —C(O)$NR^4OR^3$, —C(O)$R^4OR^3$, —C(O)$NR^4SO_2R^3$, —C(O)($C_3$-$C_{10}$ cycloalkyl), —C(O)($C_1$-$C_{10}$ alkyl), —C(O)(aryl), —C(O)(heteroaryl), —C(O)(heterocyclyl) and $CR^3OR^3$ are optionally substituted with one or more groups independently selected from halogen, cyano, nitro, azido, —$NR^3R^4$, —$OR^3$, $C_1$-$C_{10}$ alkyl, $C_2$-$C_{10}$ alkenyl, $C_2$-$C_{10}$ alkynyl, cycloalkyl and heterocycloalkyl, wherein any of said $C_1$-$C_{10}$ alkyl, $C_2$-$C_{10}$ alkenyl, $C_2$-$C_{10}$ alkynyl, cycloalkyl and heterocycloalkyl are optionally substituted with 1 or more groups independently selected from —$NR^3R^4$ and —$OR^3$;

R¹⁵ is hydrogen, halogen, methyl, fluoromethyl, difluoromethyl, trifluoromethyl or ethyl;

m is 0, 1, 2, 3, 4 or 5; and j is 0, 1 or 2.

Figure 19:
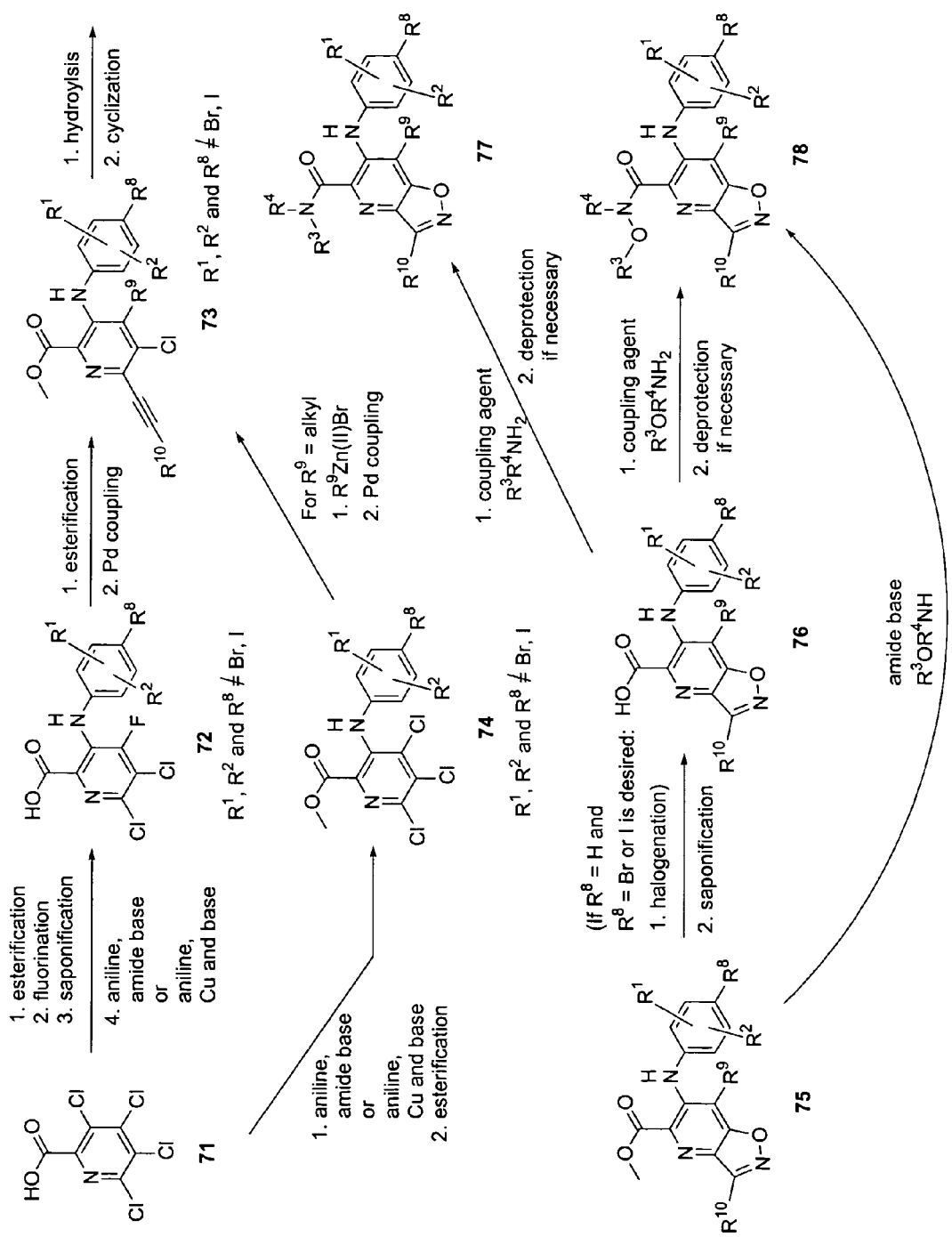
FIG. 19 shows a reaction scheme for the synthesis of compounds 75-78.
Figure 20:
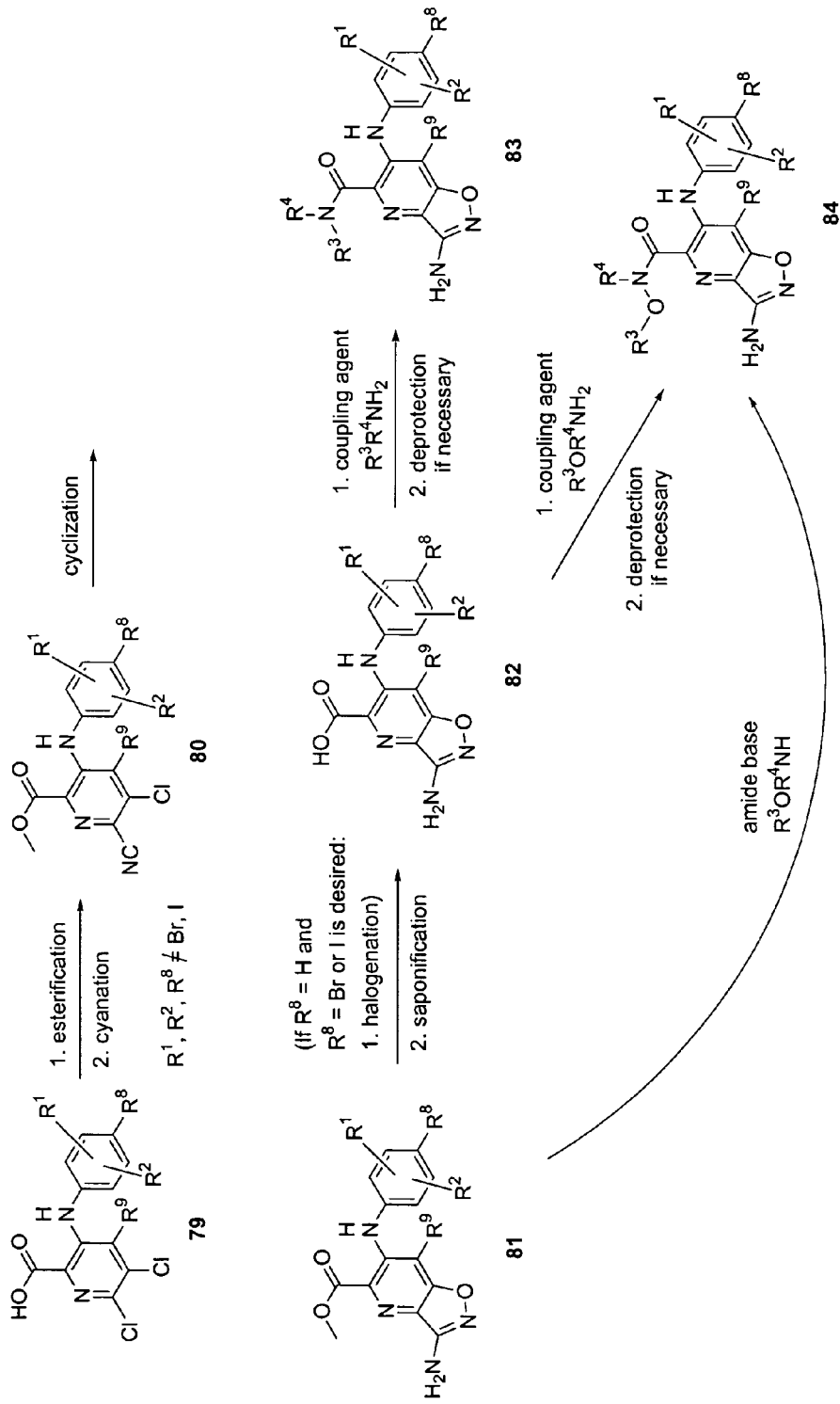
FIG. 20 shows a reaction scheme for the synthesis of compounds 81-84.
Figure 21:
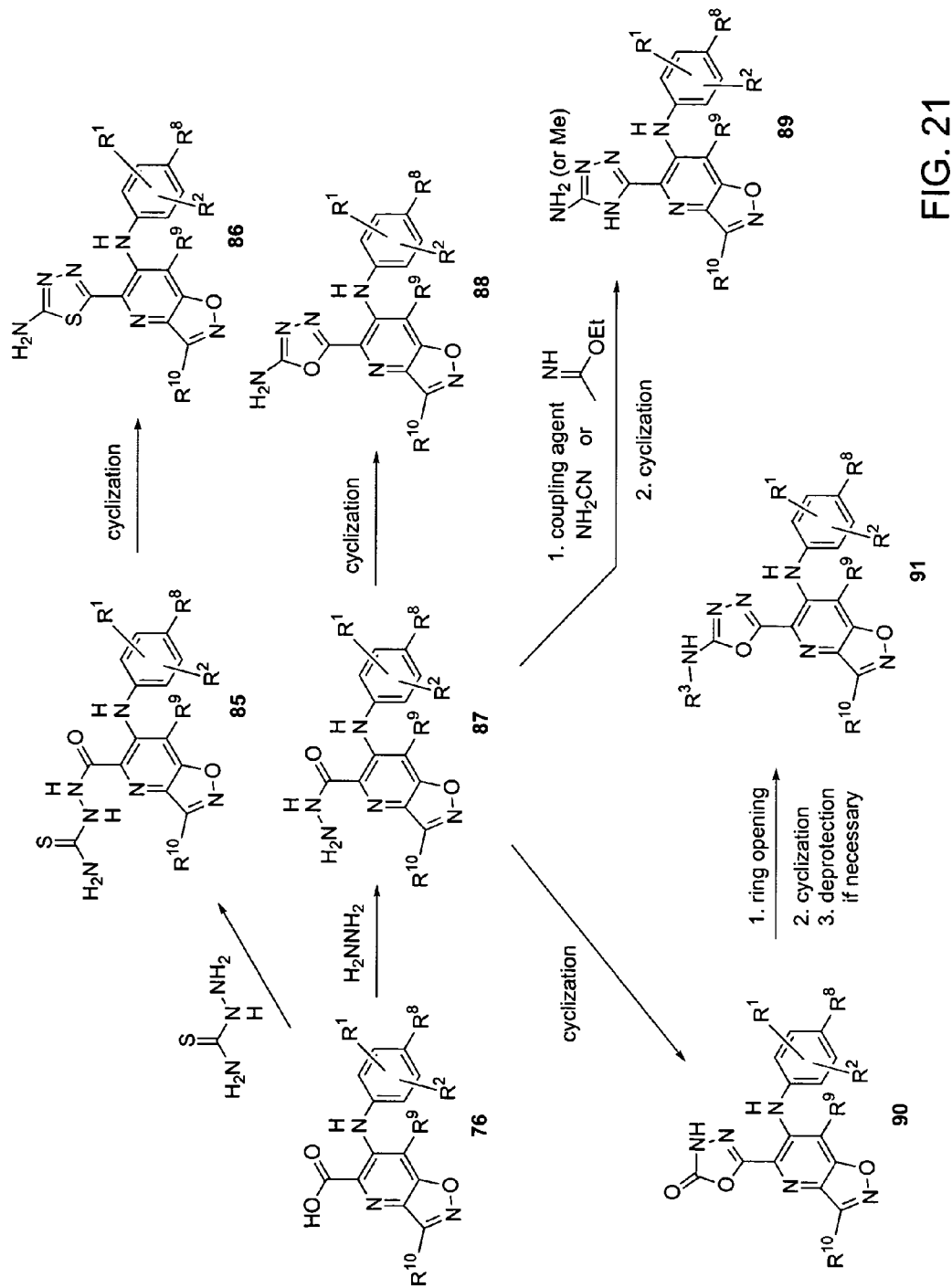
FIG. 21 shows a reaction scheme for the synthesis of compounds 85-91.

FIGS. 19-21 show non-limiting examples of the synthesis of compounds of this invention having the general Formula IV.

In another embodiment, this invention relates to compounds of the general Formula V:

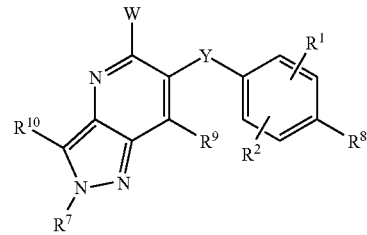

V and pharmaceutically accepted salts, prodrugs and solvates thereof, where:

Y is $NR^{15}$, O, S, S(O), S(O)$_2$, C(O) or CH$_2$;

R¹, R², R⁸, R⁹ and R¹⁰ are independently hydrogen, hydroxy, halogen, cyano, nitro, trifluoromethyl, difluoromethyl, fluoromethyl, fluoromethoxy, difluoromethoxy, trifluoromethoxy, azido, —$SR^{11}$, —$OR^3$, —C(O)$R^3$, —C(O)O$R^3$, —$NR^4$C(O)O$R^6$, —OC(O)$R^3$, —$NR^4SO_2R^6$, —$SO_2NR^3R^4$, —$NR^4$C(O)$R^3$, —C(O)$NR^3R^4$, —$NR^5$C(O)$NR^3R^4$, $NR^5$C(NCN)$NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —S(O)$_j$($C_1$-$C_6$ alkyl), —S(O)$_j$($CR^4R^5$)$_m$-aryl, aryl, arylalkyl, heteroaryl, heteroarylalkyl, heterocyclyl, heterocyclylalkyl, —O($CR^4R^5$)$_m$-aryl, —$NR^4$($CR^4R^5$)$_m$-aryl, —O($CR^4R^5$)$_m$-heteroaryl, —$NR^4$($CR^4R^5$)$_m$-heteroaryl, —O($CR^4R^5$)$_m$-heterocyclyl or —$NR^4$($CR^4R^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —$NR^4SO_2R^6$, —$SO_2NR^3R^4$, —C(O)$R^3$, —C(O)O$R^3$, —OC(O)$R^3$, —$NR^4$C(O)O$R^6$, —$NR^4$C(O)$R^3$, —C(O)$NR^3R^4$, —$NR^5$C(O)$NR^3R^4$, —$NR^5$C(NCN)$NR^3R^4$, —$OR^3$, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^7$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, $C_1$-$C_{10}$ alkyl, $C_2$-$C_{10}$ alkenyl, $C_2$-$C_{10}$ alkynyl, $C_3$-$C_{10}$ cycloalkyl, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl, and heterocyclylalkyl;

or $R^3$ and $R^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl, and heterocyclylalkyl;

$R^4$ and $R^5$ independently are hydrogen or $C_1$-$C_6$ alkyl, or $R^4$ and $R^5$ together with the atom to which they are attached form a 4 to 10 membered carbocyclic, heteroaryl or heterocyclic ring, wherein said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl, and heterocyclylalkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, aryl, heteroaryl, arylalkyl, heteroarylalkyl, heterocyclyl, and heterocyclylalkyl;

$R^{11}$, $R^{12}$ and $R^{13}$ independently are hydrogen, lower alkyl, lower alkenyl, aryl or arylalkyl, and $R^{14}$ is lower alkyl, lower alkenyl, aryl or arylalkyl;

or any two of $R^{11}$, $R^{12}$, $R^{13}$ or $R^{14}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

W is heteroaryl, heterocyclyl, —$C(O)OR^3$, —$C(O)NR^3R^4$, —$C(O)NR^4OR^3$, —$C(O)R^4OR^3$, —$C(O)NR^4SO_2R^3$, —$C(O)(C_3$-$C_{10}$ cycloalkyl), —$C(O)(C_1$-$C_{10}$ alkyl), —$C(O)(aryl)$, —$C(O)(heteroaryl)$, —$C(O)(heterocyclyl)$ or $CR^3OR^3$, wherein any of said heteroaryl, heterocyclyl, —$C(O)OR^3$, —$C(O)NR^3R^4$, —$C(O)NR^4OR^3$, —$C(O)R^4OR^3$, —$C(O)NR^4SO_2R^3$, —$C(O)(C_3$-$C_{10}$ cycloalkyl), —$C(O)(C_1$-$C_{10}$ alkyl), —$C(O)(aryl)$, —$C(O)(heteroaryl)$, —$C(O)(heterocyclyl)$ and $CR^3OR^3$ are optionally substituted with one or more groups independently selected from halogen, cyano, nitro, azido, —$NR^3R^4$, —$OR^3$, $C_1$-$C_{10}$ alkyl, $C_2$-$C_{10}$ alkenyl, $C_2$-$C_{10}$ alkynyl, cycloalkyl and heterocycloalkyl, wherein any of said $C_1$-$C_{10}$ alkyl, $C_2$-$C_{10}$ alkenyl, $C_2$-$C_{10}$ alkynyl, cycloalkyl and heterocycloalkyl are optionally substituted with 1 or more groups independently selected from —$NR^3R^4$ and —$OR^3$;

$R^{15}$ is hydrogen, halogen, methyl, fluoromethyl, difluoromethyl, trifluoromethyl or ethyl;

m is 0, 1, 2, 3, 4 or 5; and j is 0, 1 or 2.

Figure 22:
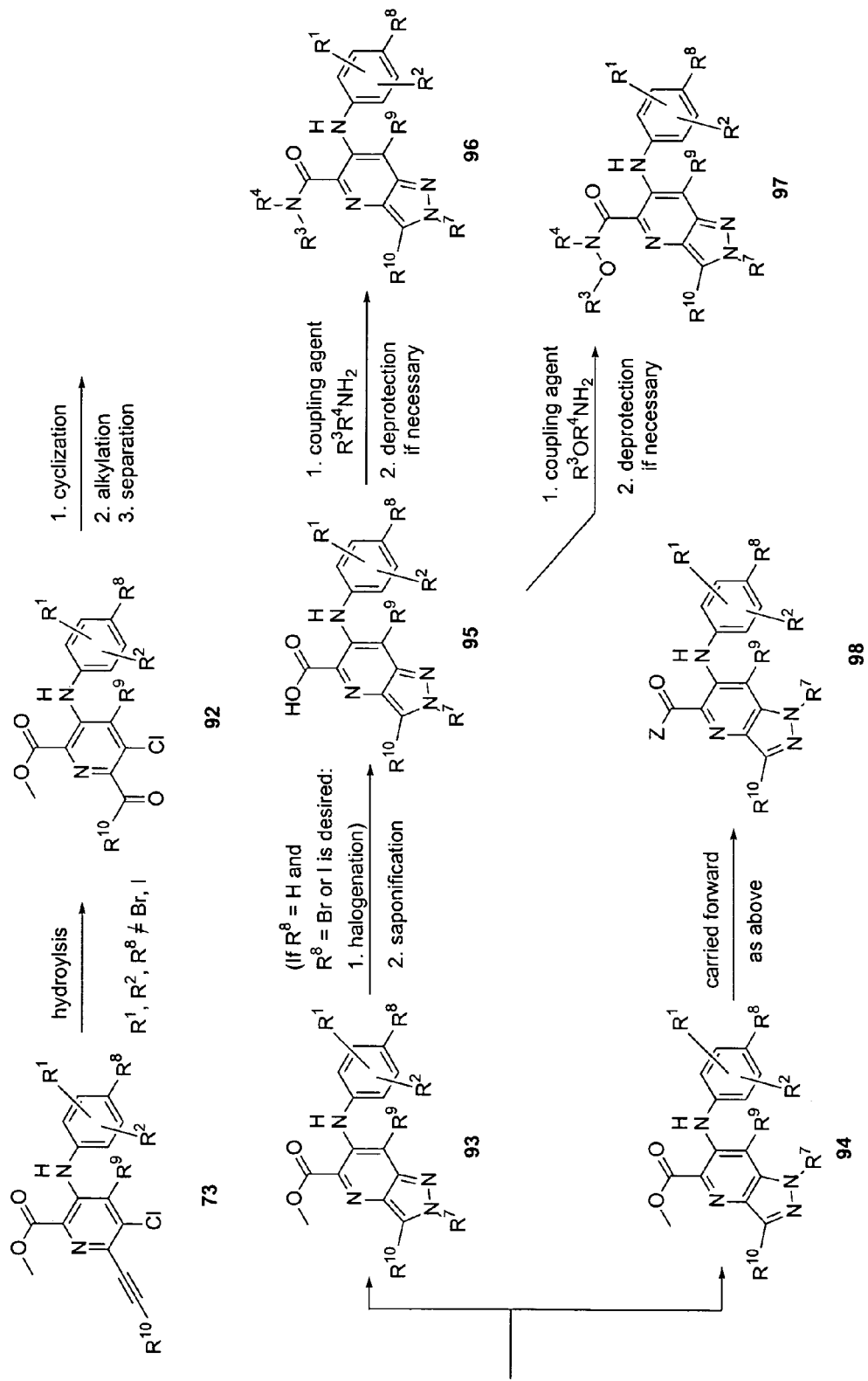
FIG. 22 shows a reaction scheme for the synthesis of compounds 93-98.
Figure 23:
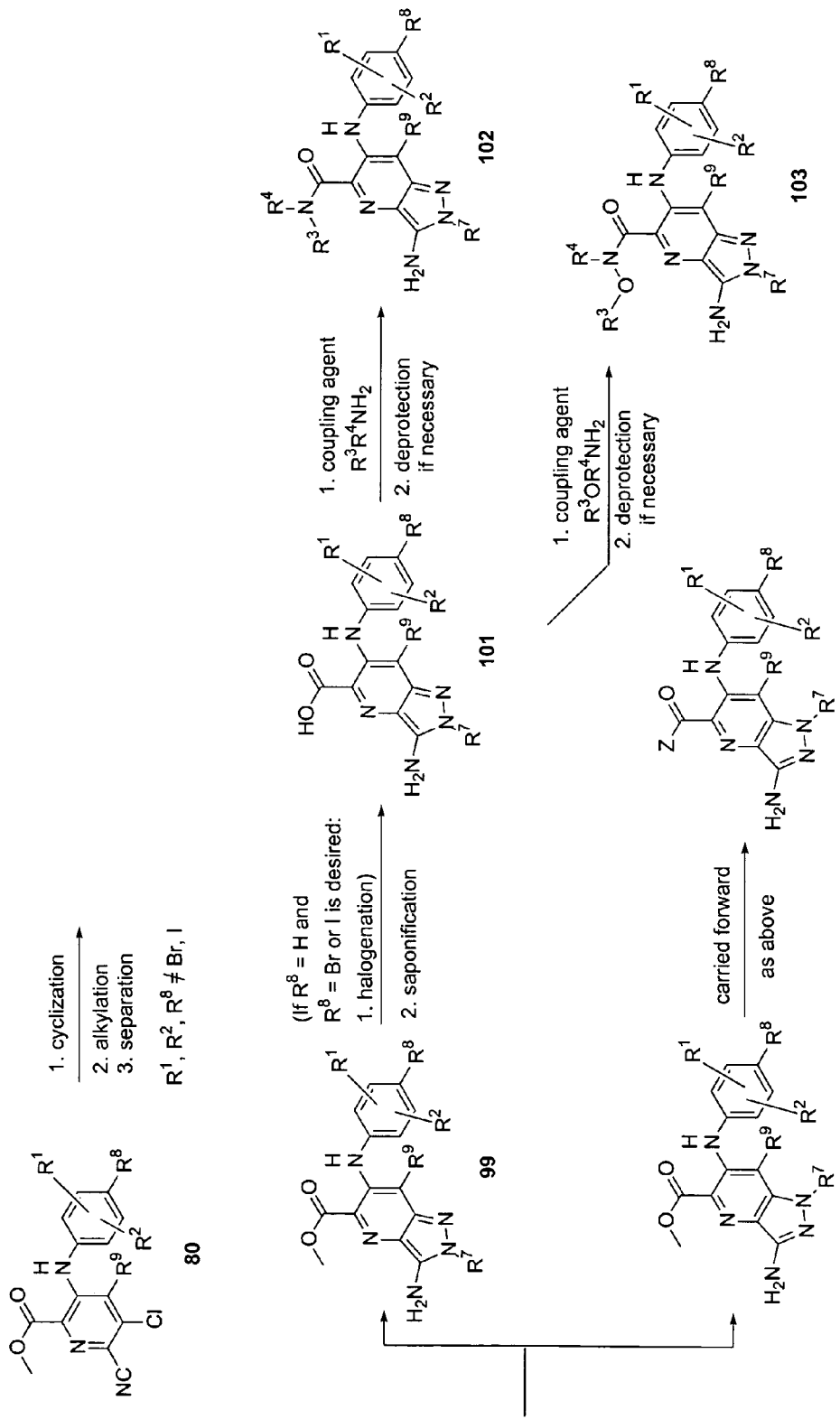
FIG. 23 shows a reaction scheme for the synthesis of compounds 99-104.
Figure 24:
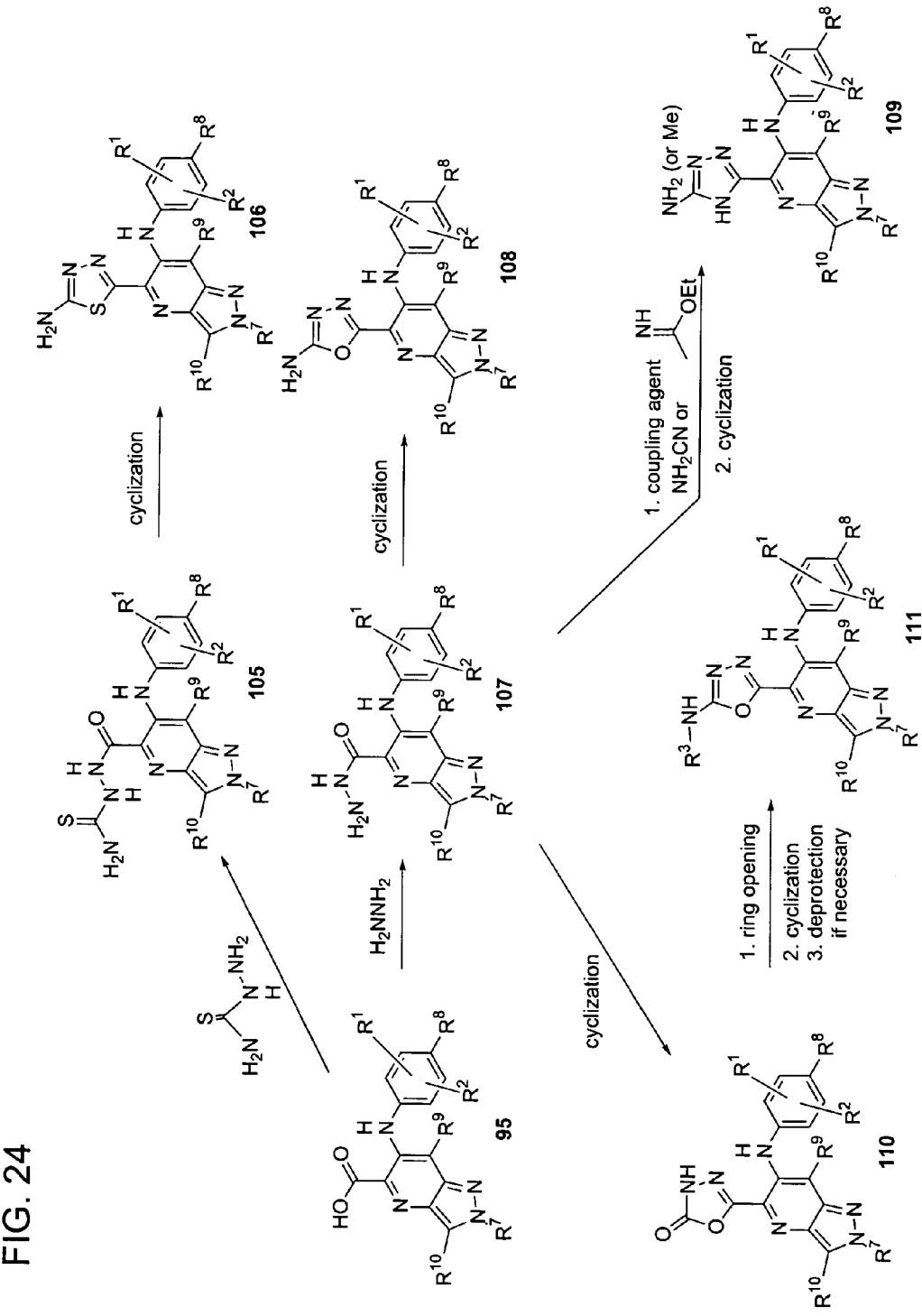
FIG. 24 shows a reaction scheme for the synthesis of compounds 105-111.

FIGS. 22-24 show non-limiting examples of the synthesis of compounds of this invention having the general Formula V.

The terms "$C_1$-$C_{10}$ alkyl", "alkyl" and "lower alkyl" as used herein refer to a saturated linear or branched-chain monovalent hydrocarbon radical having one to ten carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, neopentyl, tert-pentyl, hexyl, 2-hexyl, 3-hexyl, 3-methylpentyl, heptyl, octyl, and the like.

The terms "$C_2$-$C_{10}$ alkenyl", "lower alkenyl" and "alkenyl" refer to linear or branched-chain monovalent hydrocarbon radical having two to 10 carbon atoms and at least one double bond, and include, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations.

The terms "$C_2$-$C_{10}$ alkynyl," "lower alkynyl" and "alkynyl" refer to a linear or branched monovalent hydrocarbon radical of two to twelve carbon atoms containing at least one triple bond. Examples include, but are not limited to, ethynyl, propynyl, butynyl, pentyn-2-yl and the like, wherein the alkynyl radical may be optionally substituted independently with one or more substituents described herein.

The term "allyl" refers to a radical having the formula RC=CHCHR, wherein R is alkyl, alkenyl, alkynyl, cycloalkyl, heterocycloalkyl, aryl, heteroaryl, or any substituent as defined herein, wherein the allyl may be optionally substituted independently with one or more substituents described herein.

The terms "carbocycle," "carbocyclyl," "cycloalkyl" or "$C_3$-$C_{10}$ cycloalkyl" refer to saturated or partially unsaturated cyclic hydrocarbon radical having from three to ten carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. The cycloalkyl may be optionally substituted independently in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$) alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" or "hetercyclyl" refer to a saturated or partially unsaturated carbocyclic radical of 3 to 10 ring atoms in which at least one ring atom is a heteroatom selected from nitrogen, oxygen and sulfur, the remaining ring atoms being C, where one or more ring atoms may be optionally substituted independently with one or more substituent described below. The radical may be a carbon radical or heteroatom radical. The term further includes bicyclic and tricyclic fused ring systems which include a heterocycle fused to one or more carbocyclic or heterocyclic rings. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, trifluoromethyl, aryl, heteroaryl, and hydroxy.

The term "heteroaryl" refers to a monovalent aromatic radical of 5-, 6-, or 7-membered rings which includes fused ring systems (at least one of which is aromatic) of 5-10 atoms containing at least one and up to four heteroatoms selected from nitrogen, oxygen, or sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally mono-, di-, or trisubstituted with, e.g., substituents including, but not limited to, halogen, lower alkyl, lower alkoxy, haloalkyl, aryl, heteroaryl, and hydroxy.

The term "halogen" represents fluorine, bromine, chlorine, and iodine.

The term "arylalkyl" means an alkyl moiety (as defined above) substituted with one or more aryl moiety (also as defined above). More preferred arylalkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (also as defined above). More preferred heteroarylalkyl radicals are 5- or 6-membered heteroaryl-$C_{1-3}$-alkyls. Examples include oxazolylmethyl, pyridylethyl and the like.

The term "heterocyclylalkyl" means an alkyl moiety (as defined above) substituted with a heterocyclyl moiety (also defined above). More preferred heterocyclylalkyl radicals are 5- or 6-membered heterocyclyl-$C_{1-3}$-alkyls. Examples include tetrahydropyranylmethyl.

The term "cycloalkylalkyl" means an alkyl moiety (as defined above) substituted with a cycloalkyl moiety (also defined above). More preferred heterocyclyl radicals are 5- or 6-membered cycloalkyl-$C_{1-3}$-alkyls. Examples include cyclopropylmethyl.

The term "Me" means methyl, "Et" means ethyl, "Bu" means butyl and "Ac" means acetyl.

The term "amino acid residue" includes, but is not limited to, the 20 naturally occurring amino acids commonly designated by three letter symbols, and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone.

In general, the various moieties or functional groups of the compounds of Formulas I-V may be optionally substituted by one or more substituents. Examples of substituents suitable for purposes of this invention include, but are not limited to, oxo (with the proviso that the oxo substituent is not on an aryl or heteroaryl), halogen, cyano, nitro, trifluoromethyl, difluoromethoxy, trifluoromethoxy, azido, $-NR^4SO_2R^6$, $-SO_2NR^3R^4$, $-C(O)R^3$, $-C(O)OR^3$, $-OC(O)R^3$, $-NR^4C(O)OR^6$, $-NR^4C(O)R^3$, $-C(O)NR^3R^4$, $-NR^3R^4$, $-NR^5C(O)NR^3R^4$, $-NR^5C(NCN)NR^3R^4$, $-OR^3$, aryl, heteroaryl, arylalkyl, heteroarylalkyl, heterocyclyl, and heterocyclylalkyl, where $R^3$, $R^4$, $R^5$ and $R^6$ are as defined herein.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

In the compounds of the present invention, where a term such as $(CR^4R^5)_m$ is used, $R^4$ and $R^5$ may vary with each iteration of m above 1. For instance, where m is 2, the term $(CR^4R^5)_m$ may equal $-CH_2CH_2-$ or $-CH(CH_3)C(CH_2CH_3)(CH_2CH_2CH_3)-$ or any number of similar moieties falling within the scope of the definitions of $R^4$ and $R^5$.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures and pure enantiomers of the Formulas I-V. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced Organic Chemistry", 4th edition, J. March, John Wiley and Sons, New York, 1992).

This invention also encompasses pharmaceutical compositions containing a compound of Formula I-V and methods of treating proliferative disorders, or abnormal cell growth, by administering compounds of the present invention. Compounds of the present invention having free amino, amido, hydroxy or carboxylic groups can be converted into pharmaceutically acceptable prodrugs.

A "pharmaceutically acceptable prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. One preferred prodrug of this invention is a compound of Formula I-V covalently joined to a valine residue.

Additional types of prodrugs are also encompassed. For instance, free carboxyl groups can be derivatized as amides or alkyl esters. As another example, compounds of this invention comprising free hydroxy groups may be derivatized as prodrugs by converting the hydroxy group to a phosphate ester, hemisuccinate, dimethylaminoacetate, or phosphoryloxymethyloxycarbonyl, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.*, 1996, 39, 10. More specific examples include replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, P(O)(OH)$_2$, $-P(O)(O(C_1-C_6)$alkyl)$_2$ or glycosyl (the radical resulting from the removal of a hydroxyl group of the hemiacetal form of a carbohydrate).

Free amines can also be derivatized as amides, sulfonamides or phosphonamides. For example, a prodrug can be formed by the replacement of a hydrogen atom in the amine group with a group such as R-carbonyl, RO-carbonyl, NRR'-carbonyl where R and R' are each independently $(C_1-C_{10})$ alkyl, $(C_3-C_7)$cycloalkyl, benzyl, or R-carbonyl is a natural α-aminoacyl or natural α-aminoacyl-natural α-aminoacyl, $-C(OH)C(O)OY$ wherein Y is H, $(C_1-C_6)$alkyl or benzyl, $-C(OY_0)Y_1$ wherein $Y_0$ is $(C_1-C_4)$ alkyl and $Y_1$ is $(C_1-C_6)$ alkyl, carboxy$(C_1-C_6)$alkyl, amino$(C_1-C_4)$alkyl or mono-N- or di-N,N-$(C_1-C_6)$alkylaminoalkyl, $-C(Y_2)Y_3$ wherein $Y_2$ is H or methyl and $Y_3$ is mono-N- or di-N,N-$(C_1-C_6)$alkylamino, morpholino, piperidin-1-yl or pyrrolidin-1-yl.

All of these prodrug moieties may incorporate groups including but not limited to ether, amine and carboxylic acid functionalities.

In addition, the invention also includes solvates, pharmaceutically active metabolites, and pharmaceutically acceptable salts of compounds of Formulas I-V.

The term "solvate" refers to an aggregate of a molecule with one or more solvent molecules.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. Various forms of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "*Design and Application of Prodrugs*," by H. Bundgaard p. 113-191 (1991); c) H. Bundgaard, *Advanced Drug Delivery Reviews*, 8, 1-38 (1992); d) H. Bundgaard, et al., *Journal of Pharmaceutical Sciences*, 77:285 (1988); and e) N. Kakeya, et al., *Chem. Pharm. Bull.*, 32: 692 (1984), each of which is specifically incorporated herein by reference.

A "pharmaceutically acceptable salt" as used herein, unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alphahydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine.

Processes for the manufacture of the compounds of Formula I, Formula II, Formula III, Formula IV and Formula V are provided as further features of the invention. The inventive compounds may be prepared using the reaction routes and synthesis schemes as described below, employing the techniques available in the art using starting materials that are readily available or can be synthesized using methods known in the art.

Illustrations of the preparation of compounds of the present invention are shown in FIGS. 1-24.

FIG. 1 illustrates the synthesis of compounds of Formula I of the present invention. 6-Bromo-7-chloro-5-methyl-3H-imidazo[4,5-b]pyridine (compound 2 where $R^9$=Cl) can be prepared in a two-step procedure from the known bromoimidazo[4,5-b]pyridine 1 (Graboyes et al *J. Am. Chem. Soc.* 1957, 79, 6421-6426). Oxidation of imidazopyridine 1 can be accomplished using m-CPBA in suitable organic solvent or $H_2O_2$ in water or water/organic solvent systems. The intermediate N-oxide can then be chlorinated with $POCl_3$, or thionyl chloride, or oxalyl chloride or $PCl_5$, or MsCl in DMF. Most preferable is the use of m-CPBA in methylene chloride at or near room temperature followed by treatment with neat $POCl_3$. If a compound where $R^9$ is F is desired (compound 2 where $R^9$ is F), fluorination is accomplished through substitution of the chloride 2 ($R^9$ is Cl) intermediate by heating with either KF in DMSO, or KF and 18-Crown-6 in NMP, or CsF in MeCN.

With continued reference to FIG. 1, regardless of the nature of $R^9$ ($R^9$ is Me is known, Graboyes et al *J. Am. Chem. Soc.* 1957, 79, 6421-6426), alkylation of the imidazo[4,5-b]pyridine 2 is accomplished by use of an alkylating agent such as an alkyl halide and base such as LiH, NaH, or $K_2CO_3$ in suitable organic solvent such as DMF, MeCN, or THF at temperatures ranging from 0 to 80° C. The alkylation gives a mixture of N1 and N3 products 3 and 4 that are separable by standard techniques, including, for example, chromatography, trituration, and crystallization. The 5-methyl group of the N3-alkylsubstituted imidazo[4,5-b]pyridines 3 or 4 can be oxidized by standard method, including but not limited to $KMnO_4$ in water, $SeO_2$ in organic solvent such as dioxane, xylene, or pyridine, NaOCl/$RuCl_3$, $CrO_3$ in aqueous $H_2SO_4$, $K_2Cr_2O_7$, and $Na_2Cr_2O_7$ in water. Preferably this transformation is achieved with $KMnO_4$ in water. Incorporation of the appropriate aniline moiety to give carboxylic acid 6 can be accomplished by $S_NAr$ reaction. This can be done in a suitable organic solvent such as THF using an amide base such as LDA, LiHMDS, NaHMDS or KHMDS at appropriate temperatures (−78° C. to room temperature). Carboxylic acid 6 can also be prepared by treating imidazopyridine 5 with the appropriate aniline in the presence of CuI, Cu(OAc)$_2$, or Zn—Cu and a suitable base such as $K_2CO_3$, $Na_2CO_3$, or TEA. Additionally, preparation of carboxylic acid 6 can be achieved in a three-step sequence; esterification followed by palladium mediated cross-coupling reaction with the appropriate aniline (when $R^8$ is not Br or I) and then basic hydrolysis. Esterification can be achieved by standard methods including but not limited to Fisher esterification (MeOH, $H_2SO_4$), reaction with $TMSCHN_2$ or TMSCl in MeOH. In the second step, a suitable aniline is coupled with the intermediate ester by use of palladium catalyst, including not to limited to Pd(OAc)$_2$, Pd$_2$(dba)$_3$, or PdCl$_2$, and a ligand, such as BINAP, dppf, (o-tol)$_3$P, or (t-Bu)$_3$P, along with a base such as t-BuONa, t-BuOK, LiHMDS, or Cs$_2$CO$_3$, in a suitable organic solvent, DME, dioxane, toluene, xylene, THF, or DMF at temperatures ranging from 50 to 120° C. The aniline moiety can be further functionalized if desired by standard methods known to those skilled in the art such as halogenation. Finally, the ester is hydrolyzed by standard saponification conditions. The N3-substituted acid 6 is then converted to the N3-substituted amide analog 7 or hydroxamate analog 8 by standard coupling procedures including but not limited to EDCI, HOBt, or PyBOP and the appropriate amine or hydroxylamine in suitable organic solvents such as DMF, THF or dichloromethane. In some instances, the amine or hydroxylamine used in the coupling reaction contains a standard protecting group. In those cases, the protecting group can be removed by standard conditions known in the art. The corresponding N1-substituted imidazo[4,5-b]pyridine analog 10 can be prepared by the procedures described above after the separation step.

FIG. 2 illustrates the preparation of compounds of Formula I where W is heteroaryl or heterocyclic. The thiadiazole 12 can be prepared from the carboxylic acid 6 by treatment with thiosemicarbazide using standard EDCI coupling conditions followed by cyclization of the intermediate 11 employing PPh$_3$, TEA, and CCl$_4$ in dichloromethane. Furthermore, the N-3 substituted acid 6 can be converted to the hydrazide 13 by standard coupling procedures including but not limited to EDCI, HOBt, or PyBOP and hydrazine in suitable organic solvents such as DMF, THF or dichloromethane. The desired derivative can then be prepared by cyclization with an appropriate reagent. For aminooxadiazole 14 the hydrazide 13 is treated with BrCN and base such as NaHCO$_3$, in a suitable biphasic solvent system such as dioxane and water at room temperature. The triazole 15 can be prepared by reaction of the hydrazide 13 with an appropriate coupling agent, such as cyanamide or ethyl acetimidate, followed by cyclization using PPh$_3$, TEA, and CCl$_4$ in dichloromethane. For the preparation of the substituted aminooxadiazole 17, the hydrazide 13 is first cyclized to the oxadiazolone 16 using either CDI, phosgene or a phosgene equivalent in a suitable organic solvent such as DMF, PhMe, methylene chloride or mixtures thereof. Preferably, cyclization to form oxadiazolone 16 is accomplished by treating hydrazide 13 with CDI in DMF at room temperature. The aminooxadiazole 17 is then prepared by addition of an appropriate amine followed by re-cyclization of the intermediate obtained using PPh$_3$, TEA, and CCl$_4$ in dichloromethane. The corresponding N1-substituted imidazo[4,5-b]pyridine analogs, where W is heteroaryl or heterocyclyl, can be prepared by the procedures described above.

In FIG. 3, preparation of compounds of the Formula II is depicted. Pyrazolopyrimidine ester 20 can be prepared by the condensation of aminopyrazole 18 and ester 19 with acid (such as AcOH, HCl, ZnCl$_2$, HBr or p-TsOH) or base (such as alkylamine such as piperidine) or without acidic or basic conditions in a suitable organic solvent such as EtOH, toluene, DMF, MeCN or AcOH at elevated temperatures (80 to 120° C.). Preferably the condensation is achieved by treating the aminopyrazole 18 with ester 19 in AcOH and heating to 120° C. Chlorination of the pyrazolopyrimidine ester 20 can be accomplished with POCl$_3$, thionyl chloride, oxalyl chloride or PCl$_5$. Preferably this transformation is achieved with POCl$_3$ neat or in the presence of an amine such as triethylamine at room temperature. If a compound wherein R$^9$ is F is desired, a fluorination step can be incorporated at this stage. Fluorination of pyrazolopyrimidine ester 21 (where R$^9$ is Cl) can be accomplished with KF in the presence of 18-Crown-6 or in the presence of an amine such as trimethylamine in a suitable organic solvent such as MeCN, DMF, DMSO at the elevated temperature. Preferably this reaction is carried out with KF in the presence of 18-crown-6 in MeCN at the appropriate temperature.

With continued reference to FIG. 3, hydroxamate 23 or amide 25 can be prepared using one the following routes. The first route involves palladium mediated cross-coupling with appropriately substituted aniline and the chloro (or bromo) pyrazolopyrimidine 21 where R$^5$ is CO$_2$Et (and X is Cl or Br) to prepare ester 22. In this case, the cross-coupling can be done in a suitable organic solvent such as toluene, DME, DMF, THF, or dioxane in the presence of a base such as NaOt-Bu, KOt-Bu, K$_2$CO$_3$, Cs$_2$CO$_3$, Na$_2$CO$_3$, a phosphine ligands such as BINAP, DPPF, and (o-tol)$_3$P and a palladium catalysts such as Pd(OAc)$_2$, PdCl$_2$(dppf), Pd(dba)$_2$, and Pd$_2$(dba)$_3$ at elevated temperature (50 to 120° C.). Preferably this cross-coupling reaction is accomplished by treating the chloro (or bromo) pyrazolopyrimidine 21 with aniline (R$^8$ is not Br or I), Cs$_2$CO$_3$, BINAP, and Pd(OAc)$_2$ in toluene and heating to about 80° C. The aniline moiety can be further functionalized if desired by standard methods known to those skilled in the art such as halogenation. Hydroxamates 23 is then prepared from ester 22 using standard coupling procedures. This can be done in a suitable organic solvent such as THF using an amide base such as LiHMDS, NaHMDS or KHMDS at appropriate temperatures (0° C. to room temperature). Preferably, the hydroxylamine is added to LiHMDS in THF at low temperature (0° C.) followed by the addition of ester 22 and the reaction mixture is warm to room temperature. Ester 22 can also be converted to acid 24 by basic hydrolysis under standard conditions using either LiOH or NaOH in standard mixed aqueous/organic solvent systems. Carboxylic acid 24 can then be converted to the amide 25 or hydroxamate 23 by standard coupling procedures including but not limited to EDCI, HOBt, or PyBOP and the appropriate amine or hydroxylamine in suitable organic solvents such as DMF, THF or dichloromethane.

With continued reference to FIG. 3, an alternative second route includes a two-step procedure to carboxylic acid 24 is available when R$^5$ is Me through oxidation followed by S$_N$Ar reaction with appropriate aniline. In this case, oxidation of chloro (or bromo) pyrazolopyrimidine 21 where R$^5$ is Me (and X is Cl or Br) can be accomplished using standard methods including but not limited to KMO$_4$, NaOCl/RuCl$_3$ or Na$_2$Cr$_2$O$_7$/HCl. Incorporation of the aniline moiety is accomplished by S$_N$Ar reaction. This can be done in a suitable organic solvent such as THF using an amide base such as LDA, LiHMDS, NaHMDS or KHMDS at appropriate temperatures (−78° C. to room temperature). Preferably, the aniline is added to LDA or LiHMDS in THF at low temperature (−20 to −80° C.). The carboxylic acid intermediate is then added and the reaction mixture is warmed to room temperature to generate carboxylic acid 24. The hydroxamate 23 or amide 25 is then prepared as described above. Regardless of the route incorporated, in some instances, the amine or hydroxylamine used in the coupling reaction contains a standard protecting group. In those cases, the protecting group can be removed by standard conditions known in the art.

FIG. 4 outlines the synthesis of compounds of Formula II wherein the R$^9$ group is incorporated into the starting ethyl ester 26. Preparation of pyrazolopyrimidine ester 27 can be achieved by the condensation of aminopyrazole 18 and the ester 26 in the presence of base such as an alkylamine such as piperidine in a suitable organic solvent such as MeCN, EtOH, DMF or toluene at the appropriate temperature. Pyrazolopyrimidine ester 27 can then be carried forward to hydroxamate 23 or amide 25 as described in FIG. 3.

The preparation of compounds of Formula II where W is heteroaryl or heterocyclyl is shown in FIG. 5. The preparation of these analogs from carboxylic acid 24 is accomplished as described for the reaction schemes in FIG. 2 detailed above.

Figure 6:
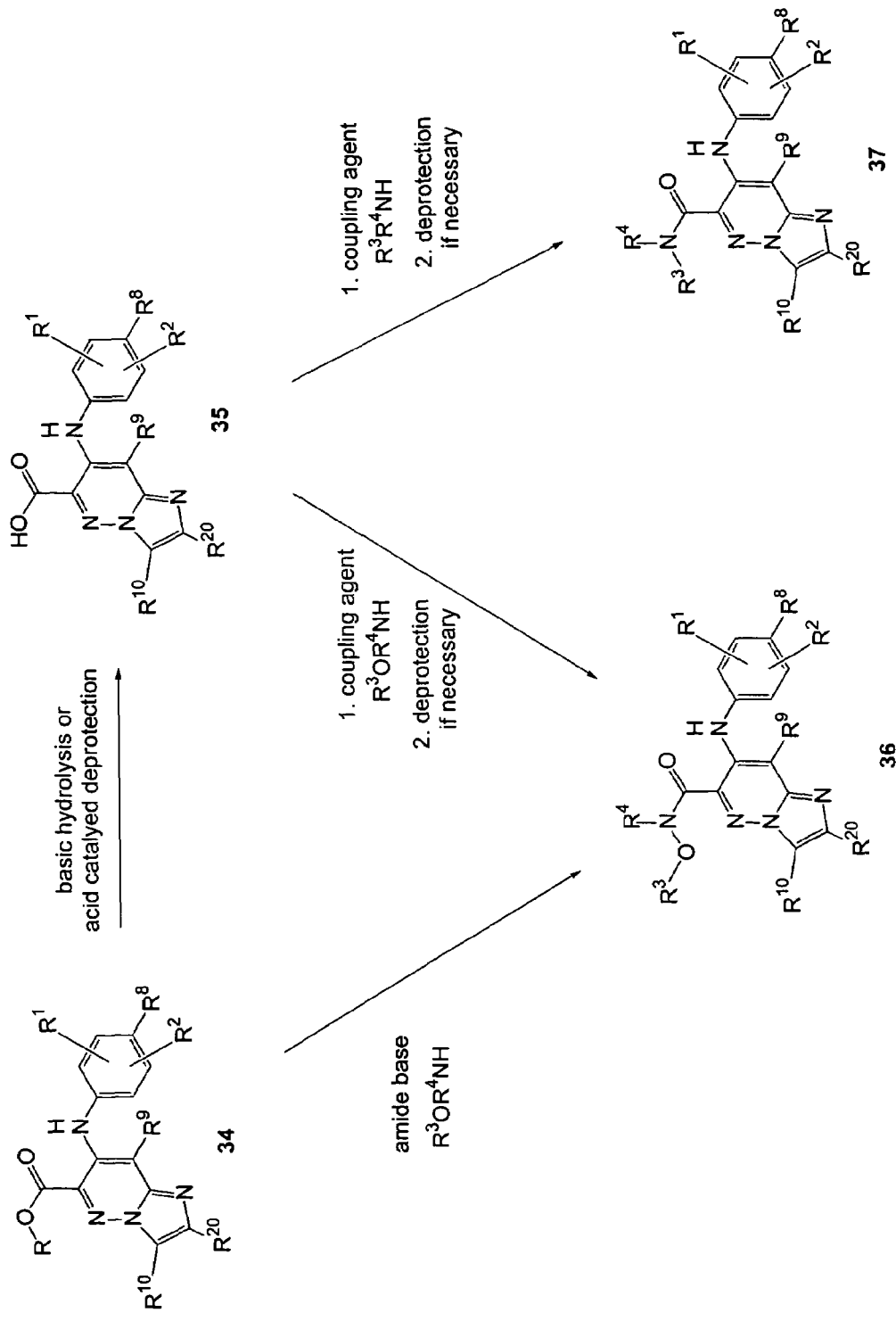
FIG. 6 shows a reaction scheme for the synthesis of compounds 35-37.

In FIG. 6, synthesis of compounds of Formula III is depicted. Imidazo[1,2-b]pyridazine ester 34, which can be synthesized as shown in FIGS. 7-11, can be converted to carboxylic acid 35, using standard saponification conditions such as LiOH or NaOH in standard mixed aqueous/organic solvent systems, when R=Me or Et. When a t-butyl ester is used, acid catalyzed deprotection of 34 can be accomplished by standard conditions including TFA in a suitable organic solvent such as methylene chloride or HCl in a suitable organic solvent such as dioxane. Hydroxamate 36 and amide 37 can be prepared using standard coupling procedures, including but not limited to EDCI, HOBt, or PyBOP and the appropriate amine or hydroxylamine in suitable organic solvents such as DMF, THF, or methylene chloride. Additionally, hydroxamate 36 and amide 37 can be prepared in two steps by initial conversion to the acid chloride by standard methods followed by addition of the appropriate amine or hydroxylamine. Alternatively imidazo[1,2-b]pyridazine ester 34 can be directly converted to hydroxamate 36 in a suitable organic solvent such as THF using the appropriate hydroxylamine and an amide base such as LDA, LiHMDS, NaHMDS, or KHMDS at appropriate temperatures (−78° C. to room temperature). In some instances, the amine or hydroxylamine used in the coupling reaction contains a standard protecting group. In those cases, the protecting group can be removed by standard conditions known in the art.

Figure 7:
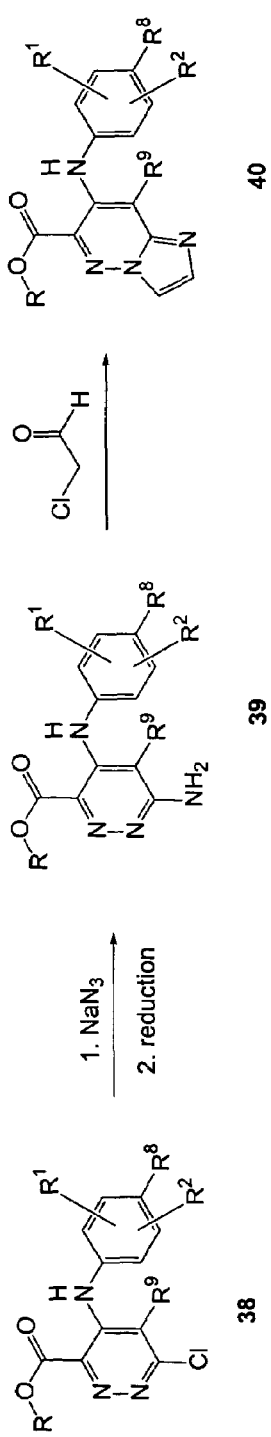
FIG. 7 shows a reaction scheme for the synthesis of compound 40.

In FIGS. 7-11, several syntheses of imidazo[1,2-b]pyridazine ester 34, which is utilized as the starting material in FIG. 6, are depicted, depending on the identity of $R^{10}$. FIG. 7 depicts the synthesis of imidazo[1,2-b]pyridazine ester 34 where $R^{10}$ is H. An appropriately functionalized 6-chloro-4-phenylaminopyridazine ester 38 (synthesized as shown in FIGS. 12-17) is converted to 6-amino-4-phenylaminopyridazine ester 39 in two steps. In the first step, sodium azide is added to 38 in an appropriate solvent, including but not limited to DMF. The 6-amino-4-phenylaminopyridazine ester 39 is prepared by reduction of the azide under standard conditions including but not limited to Zn dust/AcOH, Pt/C or $PtO_2$ in the presence of $H_2$ gas, $Ph_3P$ or $SnCl_2$/MeOH. In one embodiment, the azide reduction is accomplished by treatment with Zn dust in a mixture of methylene chloride and acetic acid. Cyclization to form imidazo[1,2-b]pyridazine 40 can be accomplished by treatment with chloroacetaldehyde or bromoacetaldehyde in suitable organic solvent such as DMF or EtOH at elevated temperatures (50 to 120° C.). In one embodiment, cyclization is realized by treatment with chloroacetaldehyde in EtOH at 70° C.

Figure 8:
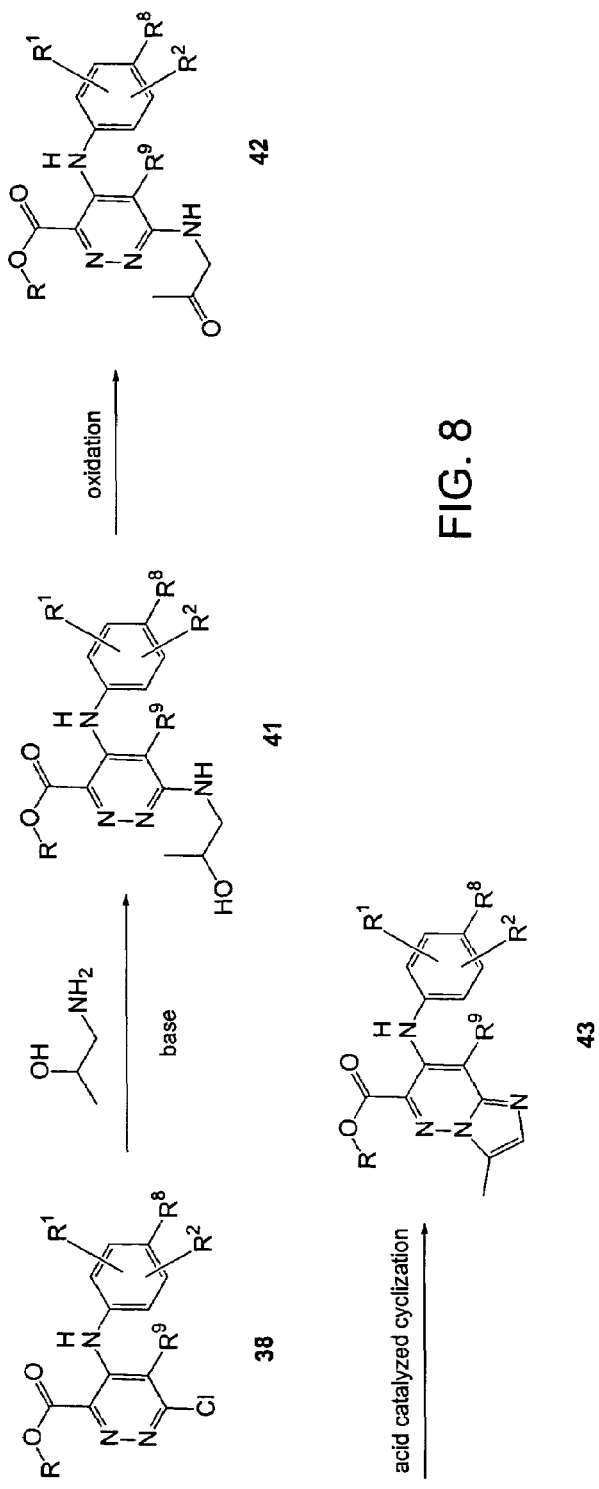
FIG. 8 shows a reaction scheme for the synthesis of compound 43.

FIG. 8 depicts the synthesis of imidazo[1,2-b]pyridazine ester 34 where $R^{10}$ is Me. 1-Aminopropan-2-ol is added to an appropriately functionalized 6-chloro-4-phenylaminopyridazine ester 38 (synthesized as shown in FIGS. 12-17) in the presence of an appropriate base, such as $NEt_3$, in an organic solvent, such as $CH_3CN$ to provide 41. Oxidation of 41 can be accomplished with an appropriate oxidizing agent, including, but not limited to TPAP and NMO, PCC, $KMnO_4$, $CrO_3$, $Na_2Cr_2O_7$. Acid catalyzed cyclization of 42 to form imidazo[1,2-b]pyridazine 43 can be accomplished with an appropriate acid, including, but not limited to $H_2SO_4$.

Figure 9:
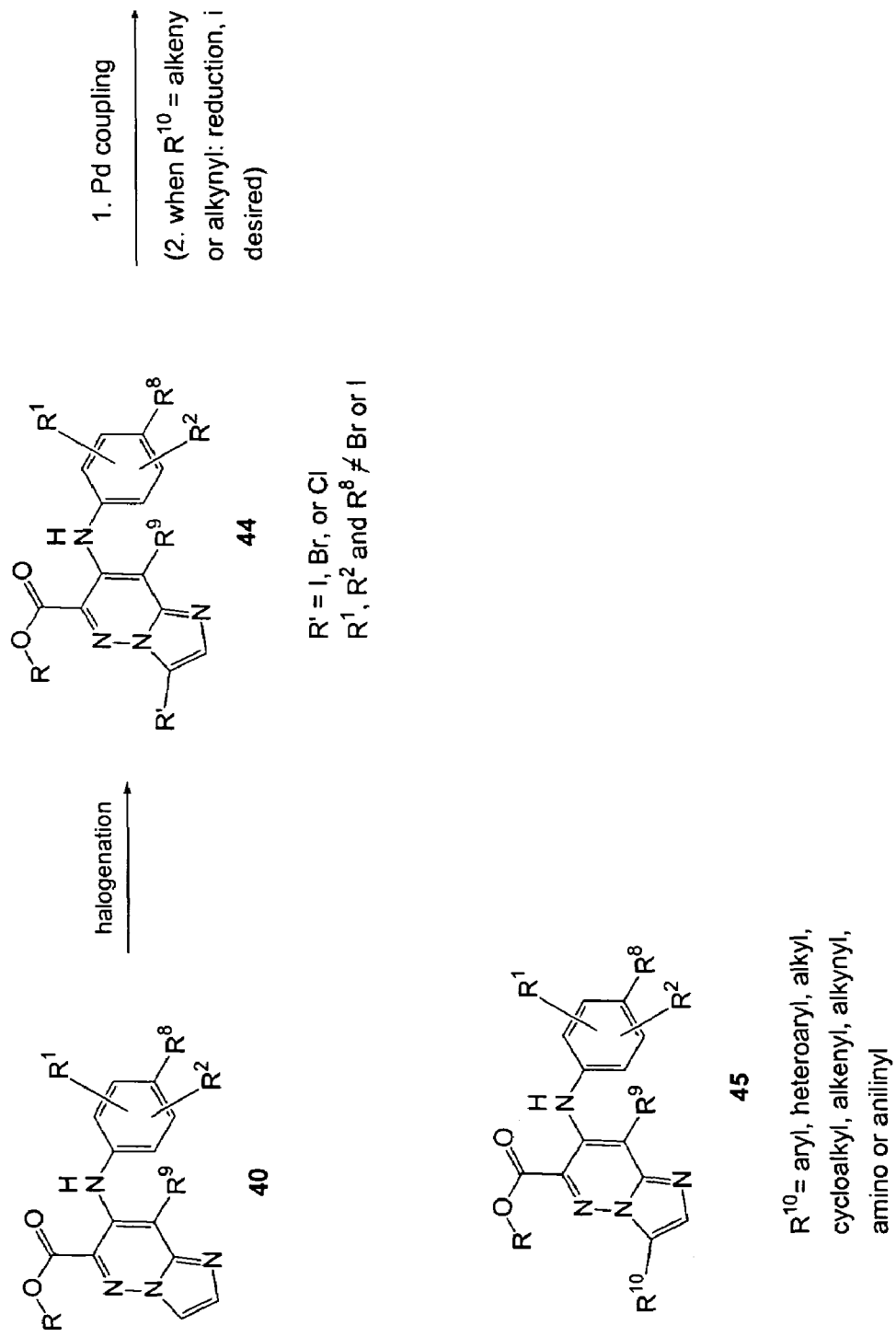
FIG. 9 shows a reaction scheme for the synthesis of compounds 44-45.

FIG. 9 depicts the synthesis of imidazo[1,2-b]pyridazine ester 34 where $R^{10}$ is aryl, heteroaryl, alkyl, cycloalkyl, alkenyl, alkynyl, amino or anilinyl. Halogenation of imidazo[1,2-b]pyridazine 40 can be accomplished by treatment with either NBS, NIS or NCS in DMF, MeCN or mixed solvent systems to form halogenated intermediate 44. Conversion of 44 to compound 45 where $R^{10}$ is aryl, heteroaryl, alkyl, cycloalkyl, alkenyl, alkynyl, amino or anilinyl can be achieved using Pd mediated cross-coupling conditions (where $R^8$ is not Br or I). When $R^{10}$ is alkenyl or alkynyl, these groups can be further reduced using the appropriate reducing agent to provide alkyl substituents at $R^{10}$. In general, this chemistry can be accomplished using a wide variety of Pd catalysts and ligands, with or without added base, in a suitable organic solvent such as DMF, PhMe, DME, THF, $CH_3CN$ at elevated temperature. The coupling partner will depend on the nature of $R^{10}$. These Pd mediated cross-couplings are well documented in the literature and are known by those skilled in the art.

Figure 10:
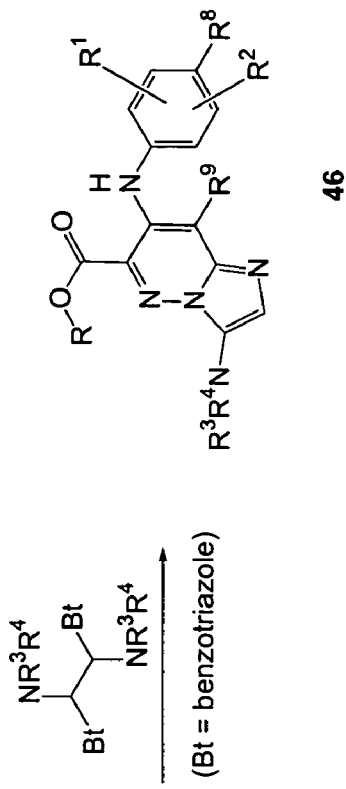
FIG. 10 shows a reaction scheme for the synthesis of compound 46.

FIG. 10 depicts the synthesis of imidazo[1,2-b]pyridazine ester 34 where $R^{10}$ is $NR^3R^4$. An appropriately functionalized 6-amino-4-phenylaminopyridazine ester 39 in a suitable organic solvent such as dichloromethane or dichloroethane is treated with a Lewis acid such as zinc bromide and condensation product as disclosed by Katritzky et al. (*J. Org. Chem.*, 2003, 68, 4935-4937: *J. Org. Chem.*, 1990, 55, 3209-3213) to provide the 3-dialkyamino-3-imidazo[1,2-b]pyridazine ring system 46. Condensation products (i.e., condensation of a glyoxal, benzotriazole and a secondary amine) can be generated using benzotriazole, glyoxal and any appropriate secondary amine including, but not limited to dimethylamine, diethylamine, pyrrolidine, piperidine, morpholine, 1-methylpiperazine, N-methyl allylamine, diallyamine, and N-methylbenzylamine as described by Katritzky et al.

Figure 11:
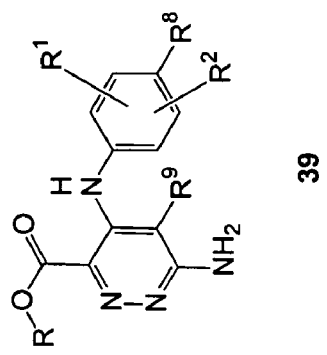
FIG. 11 shows a reaction scheme for the synthesis of compound 47.
Figure 11:
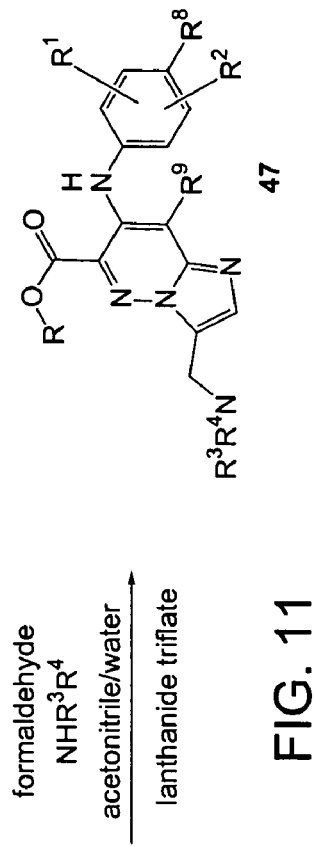

FIG. 11 depicts the synthesis of imidazo[1,2-b]pyridazine ester 34 where $R^{10}$ is $CH_2NR^3R^4$. The preparation of 3-aminomethylimidazo[1,2-b]pyridazine 47 can be accomplished using the modified Mannich reaction procedure developed by Kercher et al. (manuscript in preparation) as illustrated. The reaction is generally carried out by combining 37% aqueous formaldehyde and a suitable amine in a mixture of acetonitrile/water. Several secondary amines can be employed, including but not limited to pyrrolidine, piperadine, morpholine, dimethylamine, N-BOC-piperazine and 1-methylpiperazine. The Mannich reaction is preferentially catalyzed by a group IIIA lanthanide triflate, preferably scandium triflate, though alternatively it may be performed using an excess of protic acid (AcOH or HCl) or elevated temperatures.

Figure 12:
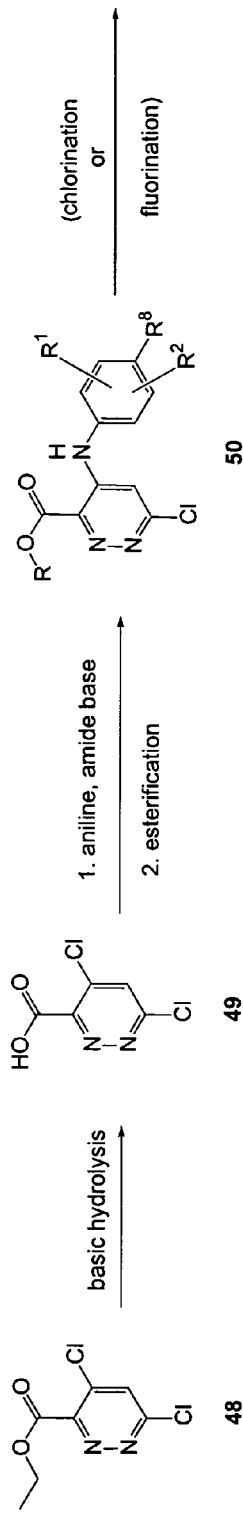
FIG. 12 shows a reaction scheme for the synthesis of compound 38.

FIGS. 12-17 depict the synthesis of an appropriately functionalized 6-chloro-4-phenylaminopyridazine ester 38, which is utilized as the starting material in FIGS. 7 and 8. FIG. 12 depicts the synthesis of the 6-chloropyridazine core where $R^9$ is H, F, or Cl. 4,6-Dichloropyridazine-3-carboxylic acid ethyl ester 48 can be synthesized as described in WO 04/031174, which is incorporated herein by reference. Basic hydrolysis of 48 using standard saponification conditions such as LiOH or NaOH in standard mixed aqueous/organic solvent systems provides acid 49. Formation of 50 can be accomplished in two steps. The first step involves the coupling of the properly substituted aniline moiety and pyridazine acid 49 by $S_NAR$ reaction. This can be achieved in a suitable organic solvent such as THF using an amide base such as LDA, LiHMDS, NaHMDS, or KHMDS at appropriate temperatures (−78° C. to room temperature). Preferably the aniline is added to LDA or LiHMDS in THF at low temperature (−20 to −80° C.). Pyridazine acid 49 is then added and the mixture is stirred at low temperature to generate the coupled product. Esterification to give the methyl ester 50 can be carried out under standard conditions, including but not limited to Fisher esterification (MeOH, $H_2SO_4$), TMSCl in MeOH or TMSCHN$_2$ in suitable organic solvents such as PhMe/MeOH. If a compound where R$^9$ is Cl or F is desired, a chlorination or fluorination step can be incorporated at this stage. Chlorination of pyridazine ester 50 can be accomplished with NCS in a suitable organic solvent such as DMF, MeCN or mixed solvent systems at room temperature. Preferably the reaction is carried out in DMF. Fluorination is achieved by treating pyridazine ester 50 with [1-(chloromethyl)-4-fluoro-1,4-diazoniabicyclo[2.2.2]octane-bis(tetrafluoroborate) in the presence of base in a suitable organic solvent at the appropriate temperature. Most preferable is the use of LiOH as base and MeCN as solvent at approximately 85° C.

Figure 13:
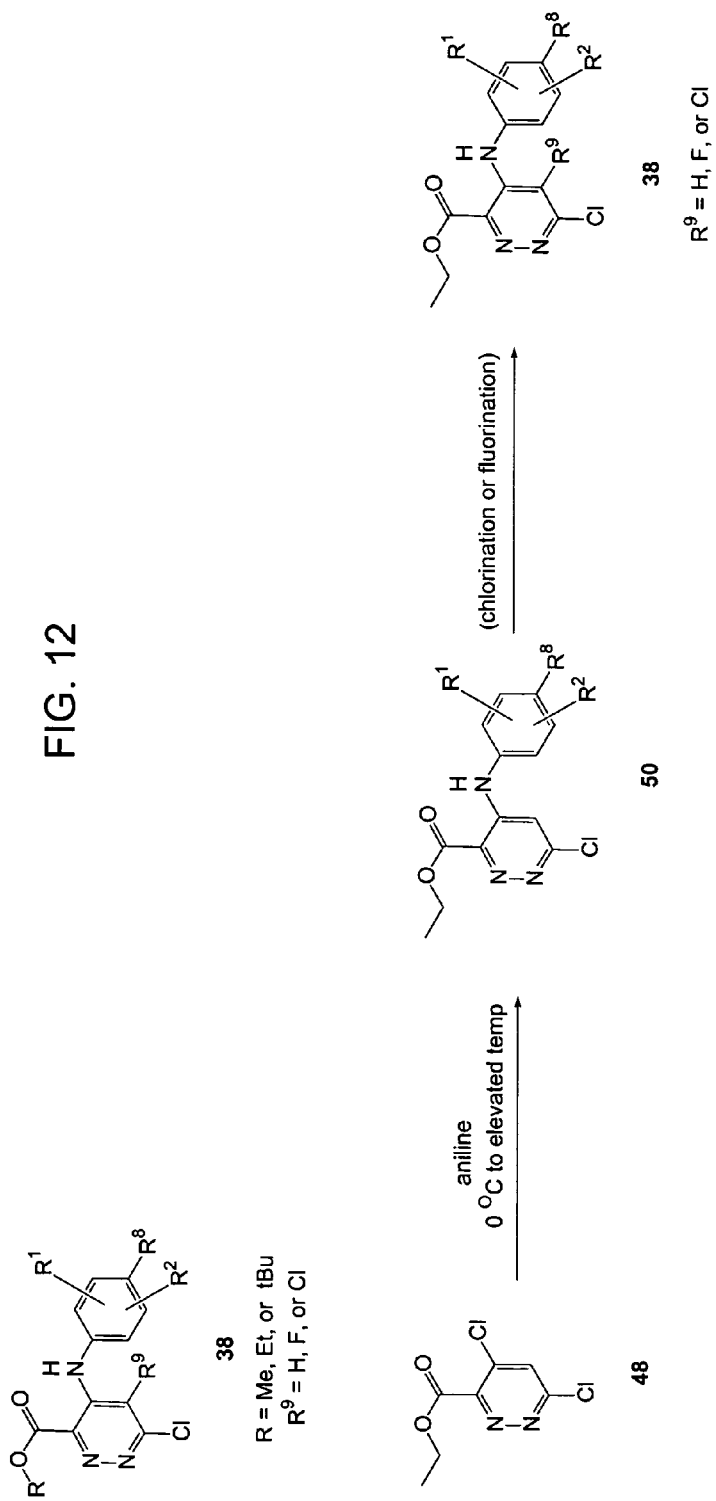
FIG. 13 shows a reaction scheme for the synthesis of compound 38.

FIG. 13 depicts an alternative synthesis of the 6-chloropyridazine core where R$^9$=H, F, or Cl. Addition of an appropriately substituted aniline to 4,6-dichloropyridazine-3-carboxylic acid ethyl ester 48 in an appropriate organic solvent such as PhMe, xylenes, NMP or DMA from 0° C. to elevated temperature can directly provide the coupled product 50. If a compound where R$^9$ is Cl or F is desired, a chlorination or fluorination step can be incorporated at this stage to provide 38. Chlorination of the pyridazine ester 50 can be accomplished with NCS in a suitable organic solvent such as DMF, MeCN or mixed solvent systems at room temperature. Preferably the reaction is carried out in DMF. Fluorination is achieved by treating pyridazine ester 50 with [1-(chloromethyl)-4-fluoro-1,4-diazoniabicyclo[2.2.2]octane-bis(tetrafluoroborate) in the presence of base in a suitable organic solvent at the appropriate temperature. Most preferable is the use of LiOH as base and MeCN as solvent at approximately 85° C.

Figure 14:
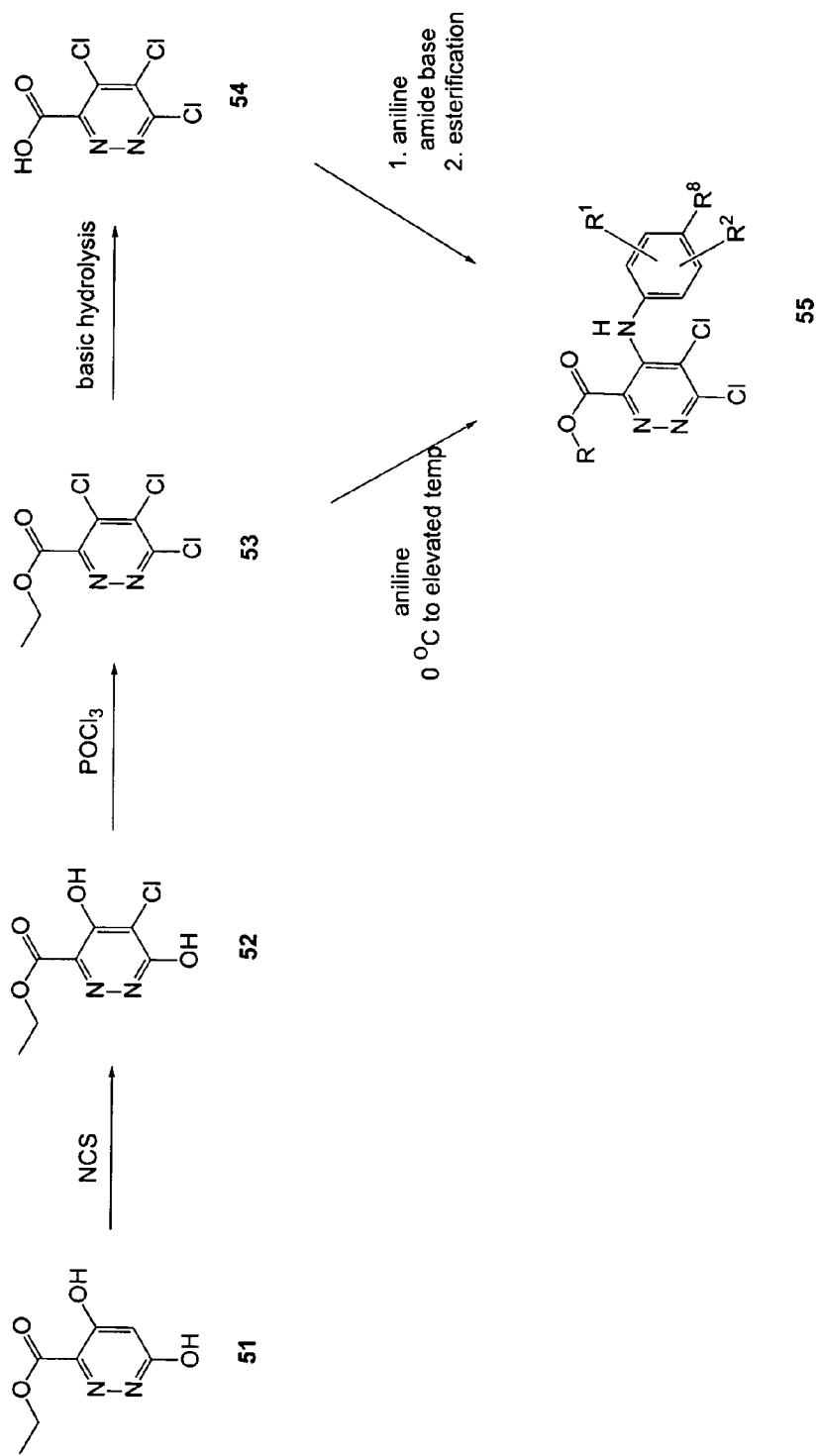
FIG. 14 shows a reaction scheme for the synthesis of compound 55.

FIG. 14 depicts the synthesis of the 6-chloropyridazine core where R$^9$ is Cl. 4,6-Dihydroxypyridazine-3-carboxylic acid ethyl ester 51 can be synthesized as described in WO 04/031174. Chlorination of pyridazine ester 51 can be accomplished with NCS in a suitable organic solvent such as DMF, MeCN or mixed solvent systems at room temperature to yield monochloropyridazine ester 52. Preferably the reaction is carried out in DMF. Pyridazine ester 52 can be further chlorinated using an appropriate reagent such as POCl$_3$, oxalyl chloride or thionyl chloride. In one embodiment, chlorination is accomplished with neat POCl$_3$ or in the presence of Et$_3$N at elevated temperatures. Hydrolysis of the resulting trichloropyridazine ester 53 to provide compound 54 can be performed under standard conditions. Addition of the appropriately substituted aniline to either 53 or 54 can be accomplished as described for the reaction schemes in FIGS. 12 and 13 detailed above to provide 55.

Figure 15:
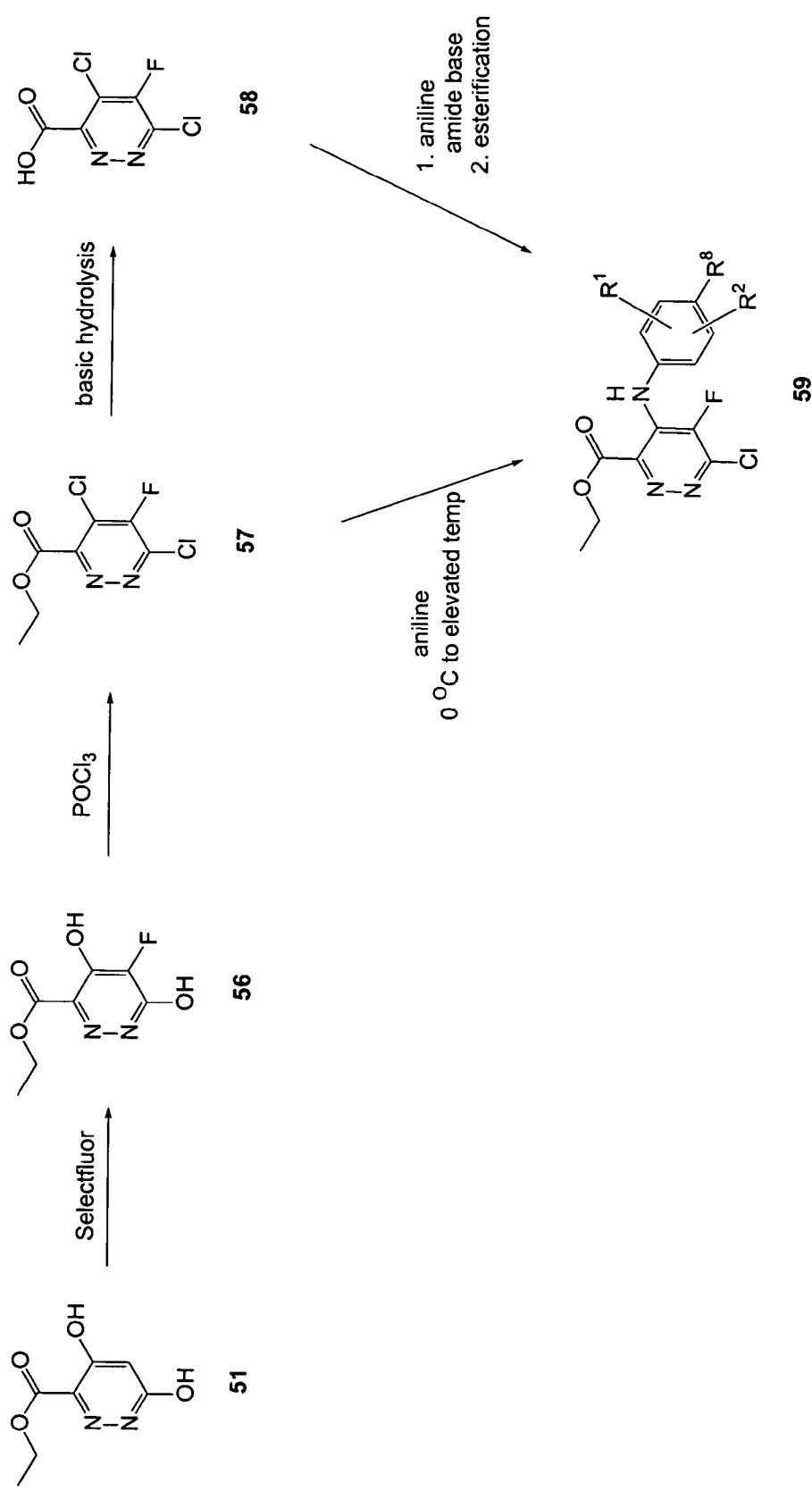
FIG. 15 shows a reaction scheme for the synthesis of compound 59.

FIG. 15 depicts the synthesis of the 6-chloropyridazine core where R$^9$ is F. Fluorination of pyridazine ester 51 can be accomplished with [1-(chloromethyl)-4-fluoro-1,4-diazoniabicyclo[2.2.2]octane-bis(tetrafluoroborate) in the presence of base in a suitable organic solvent at the appropriate temperature to yield monofluoro pyridazine ester 56. Most preferable is the use of LiOH as base and MeCN as solvent at approximately 85° C. Pyridazine ester 56 can be chlorinated using an appropriate reagent such as POCl$_3$, oxalyl chloride or thionyl chloride. In one embodiment, chlorination is accomplished with neat POCl$_3$ or in the presence of Et$_3$N at elevated temperatures. Hydrolysis of the resulting pyridazine ester 57 to provide compound 58 can be performed under standard conditions. Addition of the appropriately substituted aniline to either 57 or 58 can be accomplished as described for the reaction schemes in FIGS. 12 and 13 detailed above to provide 59.

Figure 16:
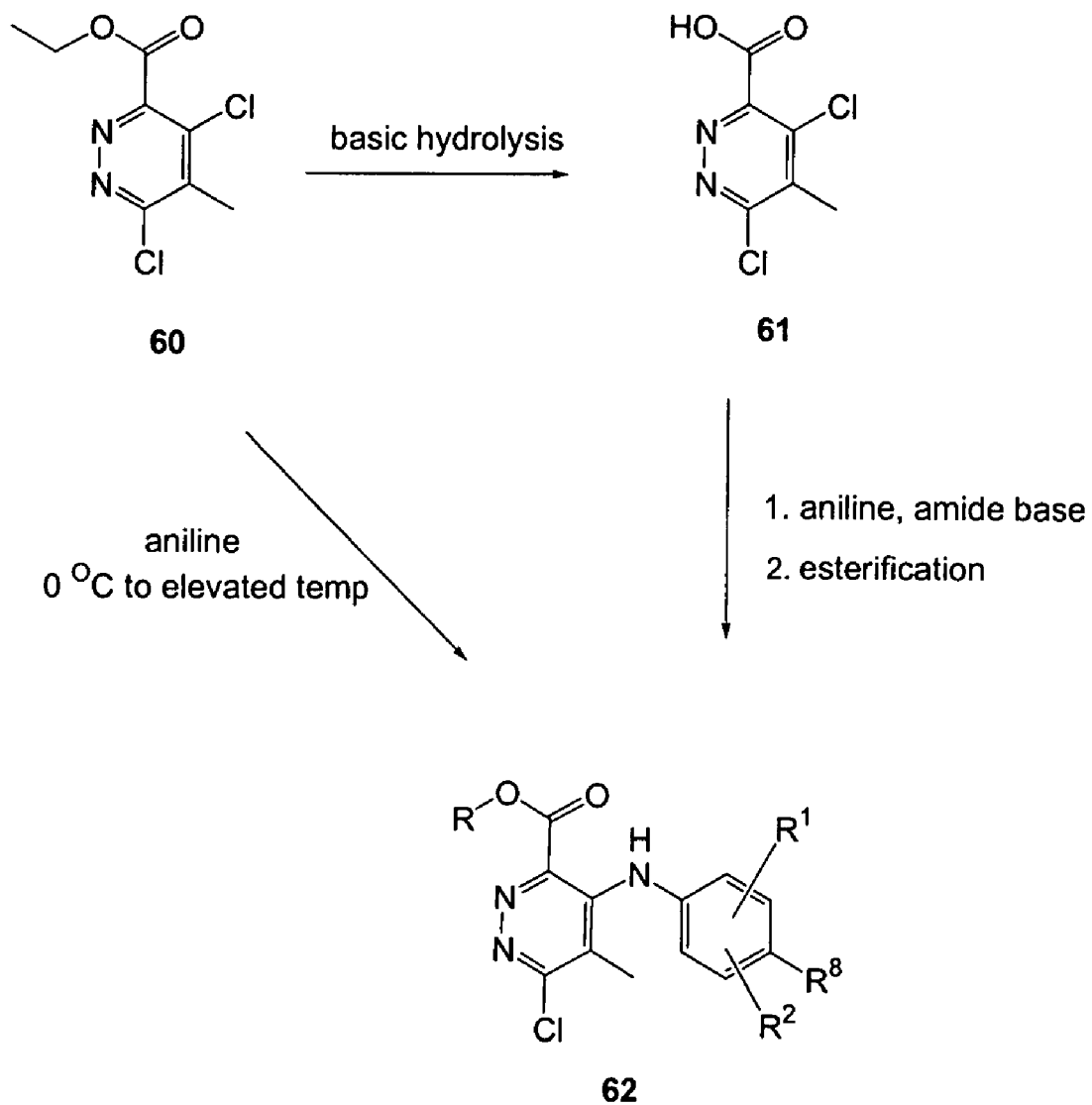
FIG. 16 shows a reaction scheme for the synthesis of compound 62.

FIG. 16 depict the synthesis of the 6-chloropyridazine core where R$^9$ is Me. Dichloro-5-methylpyridazine-3-carboxylic acid ethyl ester 60 can be prepared by minor modification of the method described in WO 04/031174. Hydrolysis of the resulting diichloropyridazine ester 60 to provide compound 61 can be performed under standard conditions. Addition of the appropriately substituted aniline to either 60 or 61 can be accomplished as described for the reaction schemes in FIGS. 12 and 13 detailed above to provide 6-chloro-5-methyl-4-phenylaminopyridazine-3-carboxylic acid ester 62.

Figure 17:
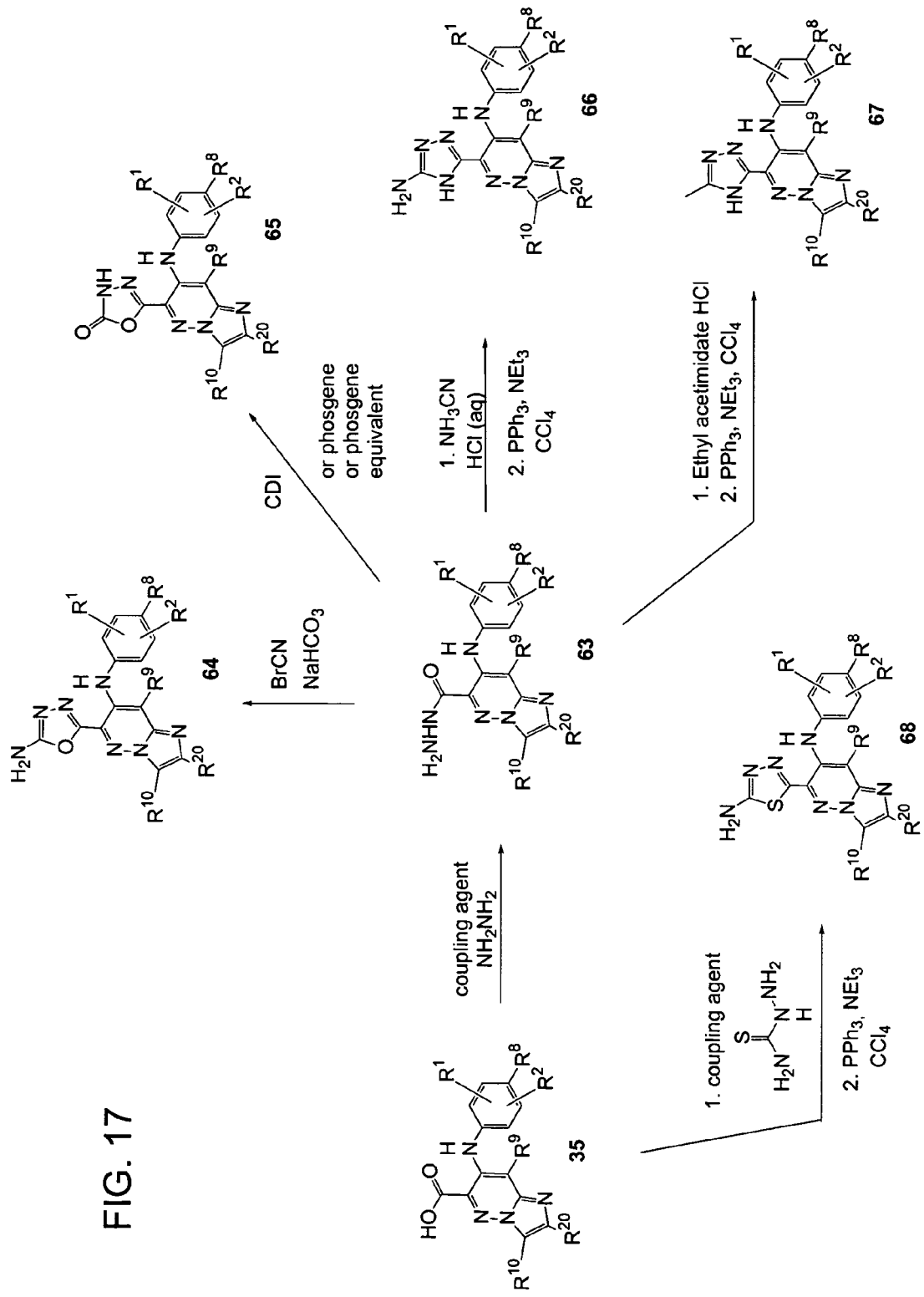
FIG. 17 shows a reaction scheme for the synthesis of compounds 63-68.
Figure 18:
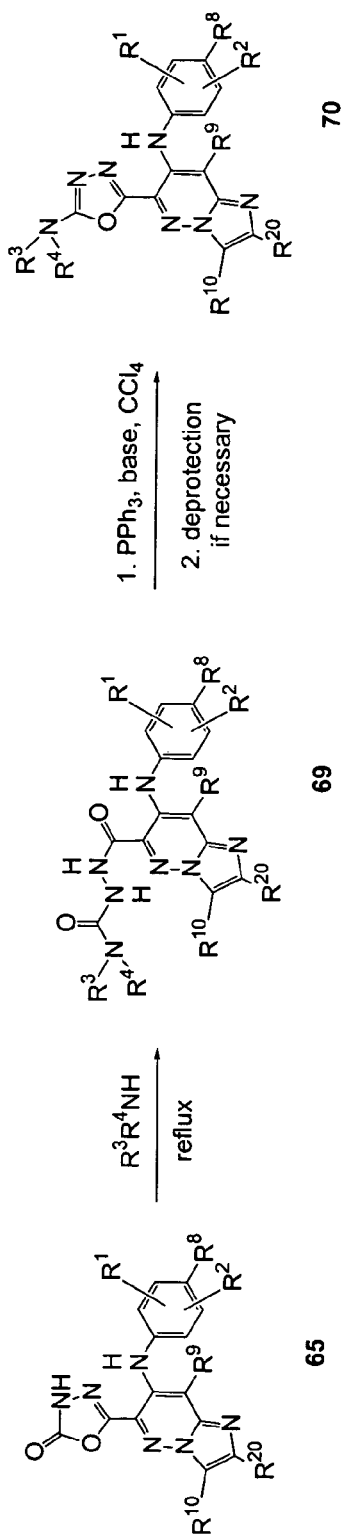
FIG. 18 shows a reaction scheme for the synthesis of compounds 69-70.

The preparation of compounds of Formula III where W is heteroaryl or heterocyclic is shown in FIGS. 17 and 18. The preparation of these analogs from carboxylic acid 35 is accomplished as described for the reaction schemes in FIG. 2 detailed above.

FIG. 19 illustrates the synthesis of compounds of Formula IV of the present invention. If a compound where R$^9$ is F is desired, a fluorination step can be introduced in a three step protocol starting from tetrachloropyridine-2-carboxylic acid 71 by esterification, fluorination and saponification. Esterification of 71 can be achieved by standard methods including but not to limited to Fisher esterification (MeOH, H$_2$SO$_4$), reaction with TMSCHN$_2$ or TMSCl in MeOH. Fluorination can be accomplished through substitution of the chloride intermediate by heating with KF in DMSO, KF and 18-Crown-6 in NMP, or CsF in MeCN. Finally, the carboxylic acid is prepared by standard saponification methods such as LiOH or NaOH in standard mixed aqueous/organic solvent systems. Dichloro-4-fluoro-3-phenylaminopyridine-2-carboxylic acid 72 can be prepared by either S$_N$Ar reaction or a copper mediated coupling. The S$_N$Ar chemistry can be achieved by treating the carboxylic acid with the desired aniline in a suitable organic solvent such as THF using an amide base such as LDA, LiHMDS, NaHMDS or KHMDS at appropriate temperatures (−78° C. to room temperature). The copper mediated coupling can be achieved by treating the carboxylic acid with the desired aniline in a suitable organic solvent in the presence of Cu or CuO and a suitable base such as K$_2$CO$_3$, or Na$_2$CO$_3$. Following esterification under standard conditions, the acetylene derivative 73 can be prepared by Sonagashira palladium mediated cross-coupling using an appropriately substituted acetylene, CuI, an amine base, palladium catalyst and organic solvent such as DME, THF, or DMF at temperatures between 25 to 100° C. (R$^8$ is not Br or I). Suitable palladium catalysts include, but are not limited to, PdCl$_2$(dppf), Pd(Ph$_3$P)$_4$, and Pd$_2$dba$_3$/dppf. Suitable amine bases include, but are not limited, to Et$_3$N, Et$_2$NH, Hunig's base, and diisopropyl amine.

With continued reference to FIG. 19, alternatively when R$^9$ is not F, carboxylic acid 71 can be taken directly into the S$_N$Ar reaction or the copper mediated coupling followed by esterification under standard methods including but not to limited to Fisher esterification (MeOH, H$_2$SO$_4$), reaction with TMSCHN$_2$ or TMSCl in MeOH to generate ester 74. If a compound where R$^9$ is alkyl is desired, the alkyl group be incorporated by the procedure of Shiota et al (J. Org. Chem. 1999, 64, 453-457) using the regioselective cross-coupling of the chloroester 74 with an appropriate alkyl organozinc and a suitable additive such as LiCl, LiBr, LiI, NaCl, or MgBr$_2$ in DMF. The alkyl group of interest may also be incorporated by use of alkyl magnesium halide as described by Troya et al (New J. Chem., 2002, 26, 1308-1313). The acetylene 73 is then prepared by the palladium mediated cross-coupling procedure described above.

With continued reference to FIG. 19, regardless of the nature of R$^9$, acetylene 73 can be carried forward in an analogous manner. Acetylene 73 can be hydrolyzed to the corresponding ketone by standard methods including but not limited to H$_2$SO$_4$, TFA, trifluorosulfonamide, FeCl$_3$, or HgSO$_4$/

$H_2SO_4$. The ketone can then be converted to the isoxazolo[4,5-b]pyridine 75 in a two-step procedure. Addition of the potassium salt of acetone oxime in a suitable organic solvent such as THF or $Et_2O$ at temperatures ranging from −78 to 5° C. is followed by acid catalyzed cyclization. The acetone oxime addition is most easily performed by addition of a THF solution of the ketone intermediate to the salt at 0° C. The cyclization can be performed under a variety of acidic aqueous conditions at a range of temperatures. If a compound is desired where $R^8$ is Br or I, then the halide of interest may be incorporated at this stage. This may be accomplished by standard aromatic halogenation chemistry including but not limited to NIS or NBS in DMF with or without catalytic aqueous acid. Basic hydrolysis under standard saponification conditions such as LiOH or NaOH in standard mixed aqueous/organic solvent systems can then provide carboxylic acid 76. Amide 77 and hydroxamate 78 can be prepared using standard coupling procedures, including but not limited to EDCI, HOBt, or PyBOP and the appropriate amine or hydroxylamine in suitable organic solvents such as DMF, THF, or methylene chloride. Alternatively, ester 75 can be directly converted to hydroxamate 78 in a suitable organic solvent such as THF using the appropriate hydroxylamine and an amide base such as LDA, LiHMDS, NaHMDS, or KHMDS at appropriate temperatures (−78° C. to room temperature). In some instances, the amine or hydroxylamine used in the coupling reaction contains a standard protecting group. In those cases, the protecting group can be removed by standard conditions known in the art.

The preparation of compounds of Formula IV is shown in FIG. 20. 5,6-dichloro-3-phenylaminopyridine-2-carboxylic acid 79 can be esterified by standard methods including but not limited to Fisher esterification (MeOH, $H_2SO_4$), reaction with $TMSCHN_2$ or TMSCl in MeOH. Nitrile 80 can then be prepared by palladium mediated coupling of the chloroester intermediate with zinc cyanide in a suitable organic solvent such as DMA, NMP or DMF at elevated temperatures ranging from 50 to 120° C. ($R^8$ is not Br or I). Several palladium catalysts may be employed including but not limited to $Pd(PPh_3)_4$, $PdCl_2(dppf)$, or $Pd_2dba_3$ with ligands such as dppe, dppp, dppf or BINAP. Preparation of aminoisoxazolo[4,5-b]pyridine 81 can be accomplished in a two-step procedure from nitrile 80 by the addition of the potassium salt of acetone oxime followed by acid mediated cyclization as described above in FIG. 19. The analogs 83 and 84 can be prepared from the intermediates 81 or 82 by the procedures described in FIG. 19.

The preparation of compounds of Formula IV where W is heteroaryl or heterocyclyl is shown in FIG. 21. The preparation of these analogs from carboxylic acid 76 is accomplished as described for the reaction schemes in FIG. 2 detailed above.

FIG. 22 illustrates the synthesis of compounds of Formula V of the present invention.

The 6-acetyl-5-chloropyridine methyl ester 92 can be prepared from the acetylene 73 as described in FIG. 19. The ketone 92 can then be converted to a mixture of N1 and N2-substituted pyrazolo[4,3-b]pyridines 93 and 94 in an manner analogous to the preparation of benzisoxazole 75 by employing the potassium salt of acetone hydrazone in place of acetone oxime in the cyclization step. Alternatively, the cyclization can also be performed by heating with hydrazine in a suitable organic solvent such as DMF or EtOH at temperature ranging from 0 to 150° C. Alkylation and separation can be accomplished as described for FIG. 1. As outlined in FIG. 22, the N1 or N2-substituted pyrazolo[4,3-b]pyridine analogs 96, 97, and 98 can be prepared by the methods described for FIG. 19 above. Additionally (as described above) ester 93 can be converted directly to hydroxamate 97 in a suitable organic solvent such as THF using the appropriate hydroxylamine and an amide base such as LDA, LiHMDS, NaHMDS, or KHMDS at appropriate temperatures (−78° C. to room temperature).

FIG. 23 illustrates the synthesis of N1 and N2-substituted 3-aminopyrazolo[4,3-b]pyridine of Formula V. Cyclization of nitrile 80 can be achieved as described in FIGS. 19 and 22. Alkylation and separation can be accomplished as described for FIG. 1. As outlined in FIG. 23, 3-aminopyrazolo[4,3-b]pyridines 99 and 100 can be further converted to the final 3-aminopyrazolo[4,3-b]pyridine analogs 102, 103, and 104 by the procedures described for FIG. 19 above. Additionally (as described above) ester 99 can be converted directly to hydroxamate 103 in a suitable organic solvent such as THF using the appropriate hydroxylamine and an amide base such as LDA, LiHMDS, NaHMDS, or KHMDS at appropriate temperatures (−78° C. to room temperature).

As shown in FIG. 24, the compounds of Formula V where W is heteroaryl or heterocyclic can be prepared from the carboxylic acid 95 by the methods described in FIG. 2. The corresponding N1-susbtituted pyrozolo[4,3-b]pyridine analogs can also be prepared in the same manner from the corresponding carboxylic acid.

The invention also relates to a pharmaceutical composition for the treatment of a hyperproliferative disorder in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for the treatment of cancer such as brain, lung, squamous cell, bladder, gastic, pancreatic, breast, head, neck, renal, kidney, ovarian, prostate, colorectal, esophageal, testicular, gynecological or thyroid cancer. In another embodiment, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to a pharmaceutical composition for the treatment of pancreatitis or kidney disease (including proliferative glomerulonephritis and diabetes-induced renal disease) or the treatment of pain in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for the prevention of blastocyte implantation in a mammal which comprises a therapeutically effective amount of a compound of the present invention, or a pharmaceutically acceptable salt, prodrug or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease or other inflammatory condition such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal that comprises administering to said mammal a therapeutically effective amount of a compound of the present invention, or a pharmaceutically acceptable salt, prodrug or hydrate thereof. In one embodiment, said method relates to the treatment of cancer such as brain, lung, squamous cell, bladder, gastric, pancreatic, breast, head, neck, renal, kidney, ovarian, prostate, colorectal, esophageal, testicular, gynecological or thyroid cancer. In another embodiment, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method for the treatment of a hyperproliferative disorder in a mammal that comprises administering to said mammal a therapeutically effective amount of a compound of the present invention, or a pharmaceutically acceptable salt, prodrug or hydrate thereof, in combination with an anti-tumor agent selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The invention also relates to a method of treating pancreatitis or kidney disease in a mammal that comprises administering to said mammal a therapeutically effective amount of a compound of the present invention, or a pharmaceutically acceptable salt, prodrug or hydrate thereof.

The invention also relates to a method of preventing blastocyte implantation in a mammal that comprises administering to said mammal a therapeutically effective amount of a compound of the present invention, or a pharmaceutically acceptable salt, prodrug or hydrate thereof.

The invention also relates to a method of treating diseases related to vasculogenesis or angiogenesis in a mammal that comprises administering to said mammal a therapeutically effective amount of a compound of the present invention, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a pharmaceutical composition for treating a disease or condition related to inflammatory disease, autoimmune disease, destructive bone disorders, proliferative disorders, infectious disease, viral disease, fibrotic disease or neurodegenerative disease in a mammal which comprises a therapeutically effective amount of a compound of the present invention, or a pharmaceutically acceptable salt, prodrug or hydrate thereof, and a pharmaceutically acceptable carrier. Examples of the above diseases and/or conditions include but is not limited to rheumatoid arthritis, atherosclerosis, inflammatory bowel disease, skin diseases such as psoriasis, eczema, and scleroderma, diabetes and diabetic complications, diabetic retinopathy, retinopathy of prematurity, age-related macular degeneration, hemangioma, chronic obstructive pulmonary disease, idiopathic pulmonary fibrosis, allergic responses including asthma allergic rhinitis and atopic dermatitis, renal disease and renal failure, polycystic kidney disease, acute coronary syndrome, congestive heart failure, osteoarthritis, neurofibromatosis, organ transplant rejection, cachexia and pain.

Patients that can be treated with compounds of the present invention, or pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a pharmaceutical composition for inhibiting abnormal cell growth in a mammal which comprises an amount of a compound of the present invention, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

This invention further relates to a method for inhibiting abnormal cell growth in a mammal or treating a hyperproliferative disorder which method comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein.

The invention also relates to a method of and to a pharmaceutical composition of inhibiting abnormal cell growth in a mammal which comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloprotienase inhibitors are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

The terms "abnormal cell growth" and "hyperproliferative disorder" are used interchangeably in this application.

"Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/theroine kinase activation occurs.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, unless otherwise indicated, refers to the act of treating as "treating" is defined immediately above.

The amount of a given agent that will correspond to such an amount will vary depending upon factors such as the particular compound, disease condition and its severity, the identity (e. g., weight) of the mammal in need of treatment, but can nevertheless be routinely determined by one skilled in the art. "Treating" is intended to mean at least the mitigation of a disease condition in a mammal, such as a human, that is affected, at least in part, by the activity of MEK, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I-V or a pharmaceutically acceptable salt or prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I-V, or a pharmaceutically acceptable salt or prodrug thereof, as defined hereinbefore in association with a pharmaceutically acceptable diluent or carrier.

To prepare the pharmaceutical compositions according to this invention, a therapeutically or prophylactically effective amount of a compound of Formula I-V or a pharmaceutically acceptable salt, solvate, metabolite or prodrug thereof (alone or together with an additional therapeutic agent) is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of Formula I-V, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of Formula I-V will naturally vary according to the nature and severity of the conditions, the age and sex of the animal or patient and the route of administration, according to well known principles of medicine.

The compounds of this invention may be used alone in combination with other drugs and therapies used in the treatment of disease states which would benefit from the inhibition of MEK. Such treatment may involve, in addition to the compounds of the invention, conventional surgery or radiotherapy or chemotherapy. Such chemotherapy may include one or more of the following categories of anti-tumor agents:

(i) antiproliferative/anti-neoplastic drugs and combinations thereof, as used in medical oncology, such as alkylating agents (for example, cis-platin, carboplatin, cyclophosphamide, nitorgen mustard, melphalan, chlorambucil, busulphan and nitorsoureas); anti-metabolites (for example, antifolates such as such as fluoropyrimidines like 5-fluorouracil and tegafur, raltitrexed, methotrexate, cytosine arabinside, hydroxyurea, or, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid); antitumor antibiotics (for example, anthracyclines like adriamycin, bleomycin, doxorubicin, daunomycin, epirubicin, idarubicin, mitomycin-C, dactinomycin and mithramycin); antimitotic agents (for example, vinca alkaloids like vincristine, vinblastine, vindesine and vinorelbine and taxoids like taxol and taxotere); and topoisomerase inhibitors (for example epipodophyllotoxins like eptoposide and teniposide, amsacrine, topotecan and campothecin):

(ii) cytostatic agents such as antiestrogens (for example, tamoxifen, toremifene, raloxifene, droloxifene and iodoxyfene), estrogen receptor down regulators (for example, fulvestratrant) antiandrogens (for example, bicalutamide, flutamide, nilutamide, cyproxerone acetate and Casodex™ (4'-cyano-3-(4-fluorophenylsulphonyl)-2-hydroxy-2-methyl-3'-(trifluoromethyl)propionanilide)), LHRH antagonists or LHRH agonists (for example, goserelin, leuporelin and buserelin), progestogens (for example, megestrol acetate), aromatase inhibitors (for example, asanastrozole, letrozole, vorazole and exemestane) and inhibitors of 5α-reductase such as finasteride;

(iii) agents which inhibit cancer cell invasion (for example, metalloproteinase inhibitors like marimastat and inhibitors of urokinase plasminogne activator receptor function);

(iv) inhibitors of growth factor function like growth factor antibodies, growth factor receptor antibodies (for example, the anti-erbB2 antibody trastumuzab [Herceptin™] and the anti-erbB1 antibody cetuximab [C225]), farnesyl transferase inhibitors, tyrosine kinase inhibitors and serine-threonine kinase inhibitors (for example, inhibitors of the epidermal growth factor family tyrosine kinases such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), inhibitors of the platelet-derived growth factor family and inhibitors of the hepatocyte growth factor family;

(v) antiangiogenic agents such as those which inhibit the effects of vascular endothelial growth factor (for example, the anti-vascular endothelial cell growth factor antibody bevacizumab [Avastin™], compounds such as those disclosed in PCT Publication Nos. WO 97/22596, WO 97/30035, WO 97/32856, and WO 98/13354) and compounds that work by other mechanisms (for example, linomide, inhibitors of integrin αvβ3 function, MMP inhibitors, COX-2 inhibitors and angiostatin);

(vi) vascular damaging agents such as Combretastatin A4 and compounds disclosed in PCT Publication Nos. WO 99/02166, WO 0/40529, WO 00/41669, WO 01/92224, WO 02/04434, and WO 02/08213;

(vii) antisense therapies (for example, those which are directed to the targets listed above such as ISIS 2503, and anti-ras antisense);

(viii) gene therapy approaches, including for example GVAX™, approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) interferon; and (x) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches to using transfected immune cells such as cytokine-transfected dendritic cells, approaches using cytokine-transfected tumor cell lines and approaches using anti-idiotypic antibodies.

Such conjoint treatment may be achieved by way of the simultaneous, sequential or separate dosing of the individual components of treatment. Such combination products employ the compounds of this invention within the dose range described hereinbefore and the other pharmaceutically active agent within its approved dose range.

According to this aspect of the invention there is provided a pharmaceutical product comprising a compound of Formula I-V as defined hereinbefore and an additional anti-tumor agent as defined hereinbefore for the conjoint treatment of cancer.

Although the compounds of Formula I-V are primarily of value as therapeutic agents for use in warm-blooded animals (including man), they are also useful whenever it is required to inhibit the effects of MEK. Thus, they are useful as pharmacological standards for use in the development of new biological tests and in the search for new pharmacological agents.

The activity of the compounds of the present invention may be determined by the following procedure. N-terminal 6 His-tagged, constitutively active MEK-1 (2-393) is expressed in *E. coli* and protein is purified by conventional methods (Ahn et al., *Science* 1994, 265, 966-970). The activity of MEK1 is assessed by measuring the incorporation of $\gamma$-$^{33}$P-phosphate from $\gamma$-$^{33}$P-ATP onto N-terminal His tagged ERK2, which is expressed in *E. coli* and is purified by conventional methods, in the presence of MEK-1. The assay is carried out in 96-well polypropylene plate. The incubation mixture (100 µL) comprises of 25 mM Hepes, pH 7.4, 10 mM $MgCl_2$, 5 mM β-glycerolphosphate, 100 µM Na-orthovanadate, 5 mM DTT, 5 nM MEK1, and 1 µM ERK2. Inhibitors are suspended in DMSO, and all reactions, including controls are performed at a final concentration of 1% DMSO. Reactions are initiated by the addition of 10 µM ATP (with 0.5 µCi $\gamma$-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvestor. Plates are allowed to air-dry prior to adding 30 µL/well of Packard Microscint 20, and plates are counted using a Packard TopCount. In this assay, compounds of the invention exhibited an $IC_{50}$ of less than 50 micromolar.

Representative compounds of the present invention, which are encompassed by the present invention include, but are not limited to the compounds of the examples and their pharmaceutically acceptable acid or base addition salts or prodrugs thereof. The examples presented below are intended to illustrate particular embodiments of the invention, and are not intended to limit the scope of the specification or the claims in any way.

The disclosures in this application of all articles and references, including patents, are incorporated herein by reference.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other MEK inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents are purchased from commercial suppliers such as Aldrich Chemical Company, Lancaster, TCI or Maybridge, and are used without further purification unless otherwise indicated. Tetrahydrofuran (THF), N,N-dimethylformamide (DMF), dichloromethane, toluene, dioxane and 1,2-difluoroethane can be purchased from Aldrich in Sure seal bottles and used as received.

The reactions set forth below are done generally under a positive pressure of nitrogen or argon or with a drying tube (unless otherwise stated) in anhydrous solvents, and the reaction flasks are typically fitted with rubber septa for the introduction of substrates and reagents via syringe. Glassware is oven dried and/or heat dried.

Column chromatography was done on a Biotage system (Manufacturer: Dyax Corporation) having a silica gel column or on a silica SepPak cartridge (Waters).

$^1$H-NMR spectra were recorded on a Varian instrument operating at 400 MHz. $^1$H-NMR spectra were obtained as CDCl$_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

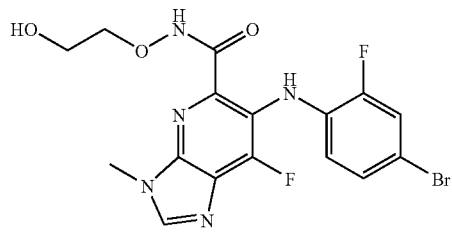

6-(4-Bromo-2-fluorophenylamino)-7-fluoro-3-methyl-3H-imidazo [4,5-b]pyridine-5-carboxylic acid (2-hydroxyethoxy)-amide Step A: Preparation of 6-bromo-5-methyl-3H-imidazo[4,5-b]pyridine 4-oxide: To a solution of 6-bromo-5-methyl-3H-imidazo[4,5-b]pyridine (1.00 equivalent) (Graboyes et al *J. Am. Chem. Soc.* 1957, 79, 6421-6426) in CH$_2$Cl$_2$ is added m-CPBA (1.50 equivalents). The resulting solution is stirred at room temperature for 16 hours. The precipitate is filtered off, washed with ether, and dried in vacuo to afford the desired product. The product is purified by re-crystallization if further purification is necessary.

Step B: Preparation of 6-bromo-7-chloro-5-methyl-3H-imidazo[4,5-b]pyridine: A solution of 6-bromo-5-methyl-3H-imidazo[4,5-b]pyridine 4-oxide (1.00 equivalent) in POCl$_3$ (excess) is stirred at 80° C. for 16 hours. The reaction mixture is concentrated in vacuo to give the crude material that is poured into ice-water. The resulting aqueous solution is neutralized with saturated aqueous NaHCO$_3$ and extracted with EtOAc. The organic layer is dried over MgSO$_4$, filtered, and concentrated in vacuo to afford the desired product. The product is purified by trituration or flash column chromatography if further purification is necessary.

Step C: Preparation of 6-bromo-7-fluoro-5-methyl-3H-imidazo[4.5-b]pyridine: To a solution of 6-bromo-7-chloro-5-methyl-3H-imidazo[4,5-b]pyridine (1.00 equivalent) in NMP is added KF (3.00 equivalents) and 18-crown-6 (0.20 equivalents) at room temperature. The resulting mixture is refluxed with stirring for 16 hours. The reaction mixture is cooled to room temperature and diluted with EtOAc and water. The organic layer is washed with brine, dried over MgSO$_4$, filtered, and concentrated in vacuo to afford the desired product that is purified by flash column chromatography as necessary.

Step D: Preparation of 6-bromo-7-fluoro-3,5-dimethyl-3H-imidazo[4,5-b]pyridine: To a solution of 6-bromo-7-fluoro-5-methyl-3H-imidazo[4,5-b]pyridine (1.00 equivalent) in DMF is added iodomethane (1.20 equivalents) and K$_2$CO$_3$ (1.50 equivalents) at room temperature. The resulting mixture is stirred at 75° C. for 1 hour. The reaction mixture is diluted with EtOAc and washed with water and brine. The organic layer is dried over MgSO$_4$, filtered, and concentrated in vacuo to give the crude material that is purified by trituration or flash column chromatography to afford the desired product.

Step E: Preparation of 6-bromo-7-fluoro-3-methyl-3H-imidazo[4.5b]pyridine-5-carboxylic acid: To a boiling suspension of 6-bromo-7-fluoro-3,5-dimethyl-3H-imidazo[4,5-b]pyridine (1.00 equivalent) and Na$_2$CO$_3$ (1.00 equivalent) in water is added powered KMnO$_4$ (3.00 equivalents) in small portions. After refluxing for 3 hours, the reaction mixture is cooled to room temperature and filtered. The filtrate is concentrated in vacuo to a half of the original volume and acidified with 6 N aqueous HCl. The precipitates are washed with water and dried in vacuo to afford the desired product. The desired product is purified by trituration or re-crystallization as necessary.

Step F: Preparation of 6-bromo-7-fluoro-3-methyl-3H-imidazo[4,5-b]pyridine-5-carboxylic acid methyl ester: To a solution of 6-bromo-7-fluoro-3-methyl-3H-imidazo[4,5-b]pyridine-5-carboxylic acid (1.00 equivalent) in THF-MeOH at 0° C. is added TMSCHN$_2$ (1.30 equivalents, 2 M solution in hexanes). The resulting mixture is warmed to room temperature and stirred for 2 hours. The reaction is quenched with AcOH. The reaction mixture is diluted with EtOAc. The organic layer is washed with saturated aqueous NaHCO$_3$ and brine, dried over MgSO₄, filtered, and concentrated in vacuo to afford the desired product that is used directly without further purification.

Step G: Preparation of 7-fluoro-6-(2-fluorophenylamino)-3-methyl-3H-imidazo[4,5-b]pyridine-5-carboxylic acid methyl ester: A mixture of 6-bromo-7-fluoro-3-methyl-3H-imidazo[4,5-b]pyridine-5-carboxylic acid methyl ester (1.00 equivalent), 2-fluoroaniline (1.00 equivalent), Pd(OAc)₂ (0.10 equivalents), rac-BINAP (0.15 equivalents), and Cs₂CO₃ (1.50 equivalents) in toluene in a sealed tube is stirred at 80° C. for 16 hours. The reaction mixture is cooled to room temperature and diluted with EtOAc. The resulting precipitate is filtered off and washed with EtOAc. The filtrate is diluted with EtOAc and washed with water. The organic layer is dried over MgSO₄, filtered, and concentrated in vacuo to give the crude material that is purified by trituration or flash column chromatography to afford the desired product.

Step H: Preparation of 6-(4-bromo-2-fluorophenylamino)-7-fluoro-3-methyl-3H-imidazo[4,5-b]pyridine-5-carboxylic acid methyl ester: To a solution of 7-fluoro-6-(2-fluorophenylamino)-3-methyl-3H-imidazo[4,5-b]pyridine-5-carboxylic acid methyl ester (1.00 equivalent) in DMF is added NBS (1.20 equivalents) at room temperature. After stirring for 16 hours at room temperature, the reaction mixture is diluted with EtOAc and washed with water. The organic layer is dried over MgSO₄, filtered, and concentrated in vacuo to give the crude material that is purified by trituration or flash column chromatography to afford the desired product as necessary.

Step I: Preparation of 6-(4-bomo-2-fluorophenylamino)-7-fluoro-3-methyl-3H-imidazo[4,5-b]pyridine-5-carboxylic acid: To a solution of 6-(4-bromo-2-fluorophenylamino)-7-fluoro-3-methyl-3H-imidazo[4,5-b]pyridine-5-carboxylic acid methyl ester (1.00 equivalent) in THF-MeOH is added 1 N aqueous LiOH (2.00 equivalents) at 0° C. The resulting mixture is warmed to room temperature and stirred for 3 hours. The reaction mixture is neutralized with 1 N aqueous HCl and extracted with EtOAc. The organic layer is washed with water, dried over MgSO₄, filtered, and concentrated in vacuo to give the crude material that is used directly without further purification.

Step J: Preparation of 6-(4-bromo-2-fluorophenylamino)-7-fluoro-3-methyl-3H-imidazo[4,5-b]pyridine-5-carboxylic acid (2-vinyloxyethoxy)-amide: To a solution of 6-(4-bromo-2-fluorophenylamino)-7-fluoro-3-methyl-3H-imidazo[4,5-b]pyridine-5-carboxylic acid (1.00 equivalent) and HOBt (1.50 equivalents) is added EDCI (1.50 equivalents) at room temperature. After stirring for 1 hour, O-(2-vinyloxy-ethyl)-hydroxylamine (1.10 equivalents) and TEA (1.20 equivalents) are added. The reaction mixture is stirred for 1 hour and diluted with EtOAc. The resulting mixture is washed with saturated aqueous NH₄Cl, brine, saturated aqueous NaHCO₃, and brine. The organic layer is dried over MgSO₄, filtered, and concentrated in vacuo to give the crude material that is used directly without further purification.

Step K: Preparation of 6-(4-bromo-2-fluorophenylamino)-7-fluoro-3-methyl-3H-imidazo[4,5-b]pyridine-5-carboxylic acid (2-hydroxyethoxy)-amide: To a solution of 6-(4-bromo-2-fluorophenylamino)-7-fluoro-3 -methyl-3H-imidazo[4,5-b]pyridine-5-carboxylic acid (2-vinyloxyethoxy)-amide (1.00 equivalent) in THF-EtOH is added 1 N aqueous HCl (2.0 equivalents) at room temperature. After stirring for 1 hour at room temperature, the reaction mixture is neutralized with saturated aqueous NaHCO3 and diluted with EtOAc. The organic layer is washed with brine, dried over MgSO₄, filtered, and concentrated in vacuo to give the crude material that is purified by trituration or flash column chromatography to afford 6-(4-bromo-2-fluorophenylamino)-7-fluoro-3-methyl-3H-imidazo[4,5-b]pyridine-5-carboxylic acid (2-hydroxyethoxy)-amide.

Example 2

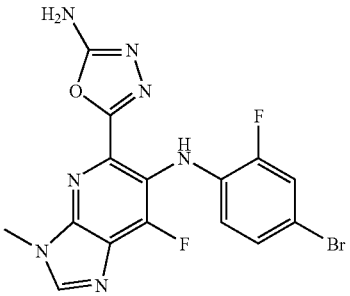

[5-(5-Amino-[1,3,4]oxadiazol-2-yl)-7-fluoro-3-methyl-3H-imidazo[4,5-b]pyridin-6-yl]-(4-bromo-2-fluorophenyl)-amine Step A: Preparation of 6-(4-bromo-2-fluorophenylamino)-7-fluoro-3-methyl-3H-imidazo[4,5-b]pyridine-5-carboxylic acid hydrazide: To a solution of 6-(4-bromo-2-fluorophenylamino)-7-fluoro-3-methyl-3H-imidazo[4,5-b]pyridine-5-carboxylic acid (1.00 equivalent) and HOBt (3.00 equivalents) is added EDCI (3.00 equivalents) at room temperature. After stirring for 1 hour, hydrazine (3.00 equivalents) and TEA (3.00 equivalents) are added. The reaction mixture is stirred for 1 hour and diluted with EtOAc. The resulting mixture is washed with saturated aqueous NH₄Cl, brine, saturated aqueous NaHCO₃, and brine. The organic layer is dried over MgSO₄, filtered, and concentrated in vacuo to give the crude material that is used directly without further purification.

Step B: Preparation of [5-(5-amino-[1,3,4]oxadiazol-2-yl)-7-fluoro-3-methyl-3H-imidazo[4,5-b]pyridin-6-yl]-(4-bromo-2-fluorophenyl)-amine: To a suspension of 6-(4-bromo-2-fluorophenylamino)-7-fluoro-3 -methyl-3H-imidazo[4,5-b]pyridine-5-carboxylic acid hydrazide (1.00 equivalent) in 1,4-dioxane at room temperature is added BrCN (2.0 equivalents) followed by a solution of NaHCO₃ (1.0 equivalents) in H₂O. After stirring for 3 hours at room temperature, the reaction mixture is diluted with water and extracted with EtOAc. The organic layer is washed with brine, dried over MgSO₄, filtered, and concentrated in vacuo to give the crude material that is purified by trituration or flash column chromatography to afford [5-(5-amino-[1,3,4]oxadiazol-2-yl)-7-fluoro-3-methyl-3H-imidazo[4,5-b]pyridin-6-yl]-(4-bromo-2-fluorophenyl)-amine.

Example 3

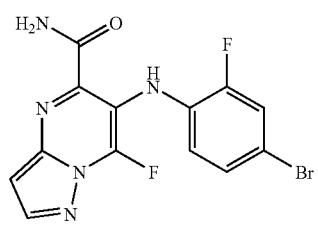

6-(4-Bromo-2-fluorophenylamino)-7-fluoropyrazolo[1,5-a]pyrimidine-5-carboxylic acid amide Step A: Preparation of 6-chloro-5-methylpyrazolo[1,5-a]pyrimidin-7-ol. A mixture of 3-aminopyrazole (10.0 g, 120.3 mmol), 2-chloro-3-oxo-butyric acid ethyl ester (16.7 mL, 120.3 mmol), and glacial acetic acid (103 mL) was heated to 120° C. for 1 hour. After cooling to room temperature, the reaction mixture was diluted with EtOH and concentrated. Trituration with $Et_2O$ gave 20.7 g (94%) desired product. MS APCI (+) m/z 184, 186 (M+, Cl pattern) detected; $^1$H NMR (400 mHz, $CD_3OD$) δ 7.90 (d, 1H), 6.17 (d, 1H), 2.53 (s, 3H).

Step B: Preparation of 6,7-dichloro-5-methylpyrazolo[1,5-a]pyrimidine. Phosphorous oxychloride (excess) is added to 6-chloro-5-methylpyrazolo[1,5-a]pyrimidin-7-ol (1.00 equivalent) and heated to 80° C. After 2 hours, the reaction mixture is concentrated under reduced pressure. The resulting residue is poured onto ice and, carefully neutralized with saturated $NaHCO_3$ (pH 8), and diluted with EtOAc. After stirring for 17 hours, the organic layer was separated and the aqueous layer was re-extracted with EtOAc, repeatedly. The combined organic extracts are dried ($MgSO_4$) and concentrated. The product is purified by flash chromatography as necessary.

Step C: Preparation of 6-chloro-7-fluoro-5-methylpyrazolo[1,5-a]pyrimidine. A mixture of 6,7-dichloro-5-methylpyrazolo[1,5-a]pyrimidine (1.00 equivalent), 18-crown-6 (5 mol %), and KF (3.00 equivalents) in MeCN is heated under reflux with stirring. After 17 hours, the reaction mixture is poured into water, extracted with EtOAc, dried ($MgSO_4$), and concentrated. The product is purified by flash chromatography as necessary.

Step D: Preparation of 6-chloro-7-fluoropyrazolo[1,5-a]pyrimidine-5-carboxylic acid. Potassium permanganate (2.00 equivalents) is added to 6-chloro-7-fluoro-5-methylpyrazolo[1,5-a]pyrimidine (1.00 equivalent) in water, and the mixture is heated at 100° C. After 3 hours, the reaction mixture is cooled to room temperature, and the precipitated oxides of manganese are filtered and washed with hot water. The filtrate is concentrated under reduced pressure, diluted with EtOAc, washed with 10% aqueous HCl solution, dried ($MgSO_4$), and concentrated. The product may be triturated with an appropriate solvent such as diethyl ether or dichloromethane if further purification is necessary.

Step E: Preparation of 6-(4-bromo-2-fluorophenylamino)-7-fluoropyrazolo[1,5-a]pyrimidine-5-carboxylic acid. To a solution of i-$Pr_2NH$ (3.50 equivalents) in THF at 0° C. is added n-BuLi (3.50 equivalents, 2.5 M solution in hexanes). After stirring 15 minutes, the mixture is cooled to −78° C. 4-Bromo-2-fluorophenylamine (2.50 equivalents) is added. After vigorous stirring for 10 minutes, a mixture of the 6-chloro-7-fluoropyrazolo[1,5-a]pyrimidine-5-carboxylic acid (1.00 equivalent) in THF is added. The dry-ice bath is removed after 30 minutes, and the reaction mixture is stirred for 17 hours at room temperature. The reaction mixture is treated with a 10% aqueous HCl solution, extracted with EtOAc, dried ($MgSO_4$), and concentrated. Trituration with methylene chloride give desired product.

Step F: Preparation of 6-(4-bromo-2-fluorophenylamino)-7-fluoropyrazolo[1,5-a]pyrimidine-5-carboxylic acid amide. A mixture of 6-(4-bromo-2-fluorophenylamino)-7-fluoropyrazolo[1,5-a]pyrimidine-5-carboxylic acid (1.00 equivalent), EDCI (1.50 equivalents), and HOBt (1.50 equivalents) in DMF is stirred for 30 minutes. $NH_4Cl$ (3.00 equivalents) is added followed by $Et_3N$ (2.50 equivalents). After 1 hour, the reaction mixture is diluted with EtOAc and washed with saturated $NH_4Cl$ solution, saturated $NaHCO_3$ solution and brine. The organic layer is dried ($MgSO_4$) and concentrated. The product is purified by flash chromatography as necessary.

Example 4

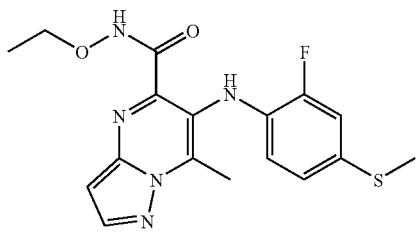

6-(2-Fluoro-4-methylsulfanyl-phenylamino)-7-methylpyrazolo[1,5-a]pyrimidine-5-carboxylic acid ethoxyamide Step A: Preparation of 6-chloro-7-methylpyrazolo[1,5-a]pyrimidine-5-carboxylic acid ethyl ester. 3-Chloro-2,4-dioxo-pentanoic ethyl ester (0.325 g, 1.685 mmol) is added to a solution of 3-aminopyrazole (0.14 g, 1.685 mmol) and piperidine (0.18 mL, 1.85 mmol) in MeCN (15 mL), and the reaction mixture heated at 90° C. for 17 hours. After cooling to room temperature, the reaction mixture is diluted with EtOH and concentrated. Purification by flash chromatography (0.5% MeOH in methylene chloride) gives 80 mg (20%) desired product. $^1$H NMR (400 mHz, $CD_3OD$) δ 8.27 (d, 1H), 6.84 (d, 1H), 4.48 (q, 2H), 2.97 (s, 3H), 1.42 (t, 3H).

Step B: Preparation of 6-(2-fluoro-4-methylsulfanyl-phenylamino)-7-methylpyrazolo[1,5-a]pyrimidine-5-carboxylic acid ethyl ester. 2-Fluoro-4-methylsulfanyl-phenylamine (1.01 equivalents), palladium(II) acetate (0.10 equivalents), rac-2,2-bis(diphenylphosphino)-1,1'-binaphthyl (0.15 equivalents), and cesium carbonate (1.50 equivalents) are added to a solution of 6-chloro-7-methylpyrazolo[1,5-a]pyrimidine-5-carboxylic acid ethyl ester (1.00 equivalent) in toluene in a sealed vial. After stirring 10 minutes, the mixture is heated to 80° C. After 24 hours, the reaction mixture is cooled to room temperature and diluted with EtOAc. The resulting precipitate is filtered and washed with EtOAc. The filtrate is diluted with EtOAc and washed with water. The aqueous layer is re-extracted with EtOAc. The combined organic layers are washed with brine, dried ($MgSO_4$) and concentrated. The product is purified by flash chromatography as necessary.

Step C: Preparation of 6-(2-fluoro-4-methylsulfanyl-phenylamino)-7-methylpyrazolo[1,5-a]pyrimidine-5-carboxylic acid ethoxyamide. O-Ethyl-hydroxylamine HCl salt (2.50 equivalents) is added to a solution of 6-(2-fluoro-4-methylsulfanyl-phenylamino)-7-methylpyrazolo[1,5-a]pyrimidine-5-carboxylic acid ethyl ester (1.00 equivalent) in THF. The solution is cooled to 0° C. and lithium bis(trimethylsilyl)amide (6.00 equivalents, 1.0 M solution in hexanes) is added dropwise. The reaction mixture is warmed to room temperature. After stirring for 1 hour, the reaction is quenched by addition of a saturated aqueous solution of $NaHCO_3$ and partitioned between EtOAc and brine. The aqueous layer is re-extracted with EtOAc. The combined organic extracts is dried (MgSO$_4$) and concentrated. The product is purified by flash chromatography as necessary.

Example 5

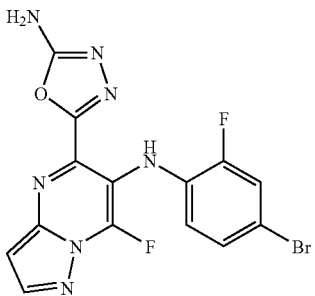

[5-(5-Amino-[1,3,4]oxadiazol-2-yl)-7-fluoropyrazolo[1,5-a]pyrimidin-6-yl]-(4-bromo-2-fluorophenyl)-amine Step A: Preparation of 6-(4-bromo-2-fluorophenylamino)-7-fluoropyrazolo[1,5-a]pyrimidine-5-carboxylic acid hydrazide. A mixture of 6-(4-bromo-2-fluorophenylamino)-7-fluoropyrazolo[1,5-a]pyrimidine-5-carboxylic acid (1.00 equivalent), EDCI (1.50 equivalents), and HOBt (1.50 equivalents) in DMF is stirred for 30 minutes. Hydrazine (3.00 equivalents) is added followed by Et$_3$N (2.50 equivalents). After 3 hours, the reaction mixture is diluted with EtOAc and washed with saturated NH$_4$Cl solution, saturated NaHCO$_3$ solution and brine. The organic layer is dried (MgSO$_4$) and concentrated. The product is purified by flash chromatography as necessary.

Step B: Preparation of [5-(5-amino-[1,3,4]oxadiazol-2-yl)-7-fluoropyrazolo[1,5-a]pyrimidin-6-yl]-(4-bromo-2-fluorophenyl)-amine. Cyanogen bromide (2.02 equivalents) is added to a suspension of 6-(4-bromo-2-fluorophenylamino)-7-fluoropyrazolo[1,5-a]pyrimidine-5-carboxylic acid hydrazide (1.00 equivalent) in dioxane followed by an aqueous NaHCO$_3$ solution (1.01 equivalents). After 17 hours, the reaction mixture is diluted with water and extracted with EtOAc. The combined organic extracts are washed with brine, dried (MgSO$_4$) and concentrated under reduced pressure. The product is purified by flash chromatography as necessary.

Example 6

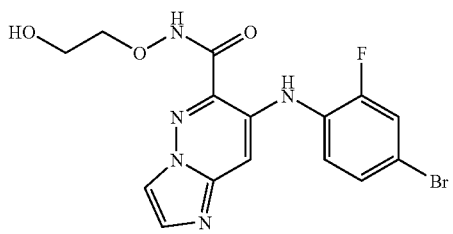

7-(4-Bromo-2-fluorophenylamino)-imidazo[1,2-b]pyridazine-6-carboxylic acid (2-hydroxyethoxy)-amide Step A. Preparation of 4,6-dichloropyridazine-3-carboxylic acid ethyl ester: 4,6-Dichloro-pyridazine-3-carboxylic acid ethyl ester is prepared from 3-oxo-pentanedioic acid diethyl ester according to the procedure described in WO 04/031174.

Step B. Preparation of 4,6-dichloropyridazine-3-carboxylic acid: To a solution of 4,6-dichloropyridazine-3-carboxylic acid ethyl ester (1.00 equivalent) in 4:1 v/v THF/MeOH is added aqueous 1 M NaOH (5.00 equivalents). The reaction mixture is stirred at room temperature for 1 hour. The reaction mixture is acidified to pH 1-2 with aqueous 1 M HCl, diluted with water, and extracted with ethyl acetate/THF. The organic layer is washed with water, saturated NaCl, is dried (Na$_2$SO$_4$), and is concentrated under reduced pressure to afford the desired product.

Step C. Preparation of 4-(4-bromo-2-fluorophenylamino)-6-chloro-pyridazine-3-carboxylic acid: LiHMDS (1.0 M solution in hexanes, 3.20 equivalents) is added dropwise to a stirred solution of 4-bromo-2-fluorophenylamine (2.10 equivalents) in THF cooled to −78° C. After one hour, 4,6-dichloropyridazine-3-carboxylic acid (1.00 equivalent) is added dropwise as a solution in THF. The reaction mixture is allowed to warm to room temperature slowly and is stirred for 16 hours. The reaction mixture is quenched with water, diluted with ethyl acetate and acidified with aqueous 1 M HCl. The layers are separated and the aqueous phase is extracted with ethyl acetate (3×). The combined organic phases are dried (Na$_2$SO$_4$) and concentrated under reduced pressure to give the desired product. The product may be triturated with an appropriate solvent such as diethyl ether or dichloromethane if further purification is necessary.

Step D. Preparation of 4-(4-bromo-2-fluorophenylamino)-6-chloro-pyridazine-3-carboxylic acid tert-butyl ester: 2-tert-Butyl-1,3-diisopropylisourea (5.50 equivalents) is added to 4-(4-bromo-2-fluorophenylamino)-6-chloro-pyridazine-3-carboxylic acid (1.00 equivalent) in THF. The reaction mixture is stirred for 5 hours at reflux. The reaction mixture is cooled to room temperature and diluted with EtOAc. The organic layer is washed with 10% K$_2$CO$_3$ and saturated NaCl, dried (Na$_2$SO$_4$), and concentrated in vacuo. The crude product is redissolved in dichloromethane and the resulting white solid is removed by filtration (urea byproduct). The filtrate is concentrated under reduced pressure to provide the desired product. The product may be purified by flash column chromatography if further purification is necessary.

Step E. Preparation of 6-azido-4-(4-bromo-2-fluorophenylamino)-pyridazine-3-carboxylic acid tert-butyl ester: Sodium azide (2.00 equivalents) is added to a solution of 4-(4-bromo-2-fluorophenylamino)-6-chloro-pyridazine-3-carboxylic acid tert-butyl ester (1.00 equivalent) in DMF and the reaction mixture is stirred at 80° C. for 16 hours. After cooling to room temperature, the reaction mixture is diluted with ethyl acetate and washed with water, saturated NaHCO$_3$ and saturated NaCl. The organic layer is dried (Na$_2$SO$_4$) and concentrated under reduced pressure to provide the desired product. The product may be purified by flash column chromatography if further purification is necessary.

Step F. Preparation of 6-amino-4-(4-bromo-2-fluorophenylamino)-pyridazine-3-carboxylic acid tert-butyl ester: Zinc powder (5.00 equivalents) is added portion-wise to a suspension of 6-6-azido-4-(4-bromo-2-fluorophenylamino)-pyridazine-3-carboxylic acid tert-butyl ester (1.00 equivalent) in 3:1 v/v dichloromethane/acetic acid. After fifteen minutes, the reaction mixture is poured into ethyl acetate. The organic layer is washed with water, saturated NaHCO₃ and saturated NaCl. The organic layer is dried (Na₂SO₄) and concentrated under reduced pressure to provide the desired product. The product may be triturated with an appropriate solvent such as diethyl ether or dichloromethane if further purification is necessary.

Step G. Preparation of 7-(4-bromo-2-fluorophenylamino)-imidazo[1,2-b]pyridazine-6-carboxylic acid: Chloroacetaldehyde (50% aqueous solution, 5.00 equivalents) is added to a suspension of 6-amino-4-(4-bromo-2-fluorophenylamino)-pyridazine-3-carboxylic acid tert-butyl ester (1.00 equivalent) in ethanol contained in a sealed tube. The reaction mixture is heated at 80° C. for two days and then cooled to room temperature. The reaction mixture is concentrated and then diluted with ethyl acetate. The organic layer is washed with saturated NaCl, dried (Na₂SO₄) and concentrated under reduced pressure to provide the desired product. The product may be triturated with an appropriate solvent such as diethyl ether or dichloromethane if further purification is necessary.

Step H. Preparation of 7-(4-bromo-2-fluorophenylamino)-imidazo[1,2-b]pyridazine-6-carboxylic acid (2-vinyloxyethoxy)-amide: A mixture of 7-(4-bromo-2-fluorophenylamino)-imidazo[1,2-b]pyridazine-6-carboxylic acid (1.00 equiv), EDCI (1.50 equivalents), and HOBt (1.50 equivalents) in DMA is stirred for 30 minutes at room temperature under N₂. O-(2-vinyloxy-ethyl)-hydroxylamine (3.00 equivalents) is added followed by Et₃N (2.50 equivalents). After the reaction mixture is stirred for 16 hours at room temperature, it is diluted with EtOAc and washed with saturated NH₄Cl solution, saturated NaHCO₃ solution and saturated NaCl. The organic layer is dried (Na₂SO₄) and concentrated under reduced pressure to yield the desired product. The product may be purified by flash column chromatography if further purification is necessary.

Step I. Preparation of 7-(4-bromo-2-fluorophenylamino)-imidazo[1,2-b]pyridazine-6-carboxylic acid (2-hydroxyethoxy)-amide: To a solution of 7-(4-bromo-2-fluorophenylamino)-imidazo[1,2-b]pyridazine-6-carboxylic acid (2-vinyloxyethoxy)-amide (1.00 equivalent) in ethanol is added aqueous 2 M HCl (5.00 equivalents). The reaction mixture is stirred for 16 hours at room temperature. The reaction mixture is adjusted with aqueous 1 M NaOH until the pH is 7. The reaction mixture is diluted with EtOAc and H₂O. The organic layer is separated and washed with saturated NaCl, dried (Na₂SO₄), and concentrated under reduced pressure to yield the desired product. The product may be purified by flash column chromatography if further purification is necessary.

Example 7

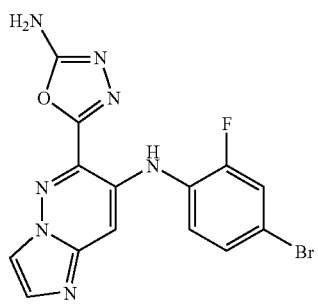

[6-(5-Amino-[1,3,4]oxadiazol-2-yl)-imidazo[1,2-b]pyridazin-7-yl]-(4-bromo-2-fluorophenyl)-amine Step A. Preparation of 7-(4-bromo-2-fluorophenylamino)-imidazo[1,2-b]pyridazine-6-carboxylic acid hydrazide: A mixture of 7-(4-bromo-2-fluorophenylamino)-imidazo[1,2-b]pyridazine-6-carboxylic acid (1.00 equiv), EDCI (1.50 equivalents), and HOBt (1.50 equivalents) in DMA is stirred for 30 minutes at room temperature under N₂. Hydrazine (3.00 equivalents) is added followed by Et₃N (2.50 equivalents). After the reaction mixture is stirred for 16 hours at room temperature, it is diluted with EtOAc and washed with saturated NH₄Cl solution, saturated NaHCO₃ solution and saturated NaCl. The organic layer is dried (Na₂SO₄) and concentrated under reduced pressure to yield the desired product. The product may be purified by flash column chromatography if further purification is necessary.

Step B: Preparation [6-(5-amino-[1,3,4]oxadiazol-2-yl)-imidazo[1,2-b]pyridazin-7-yl]-(4-bromo-2-fluorophenyl)-amine. 7-(4-Bromo-2-fluorophenylamino)-imidazo[1,2-b]pyridazine-6-carboxylic acid hydrazide (1.00 equivalent) is suspended in dioxane. Cyanogen bromide (1.01 equivalents) is added, followed by a solution of sodium bicarbonate (1.00 equivalent) in H₂O. The reaction mixture is stirred at room temperature for 16 hours. The reaction mixture is diluted with ethyl acetate and washed with water and saturated aqueous NaCl. The organic layer is dried (Na₂SO₄) and concentrated under reduced pressure to yield the desired product. The product may be purified by flash column chromatography if further purification is necessary.

Example 8

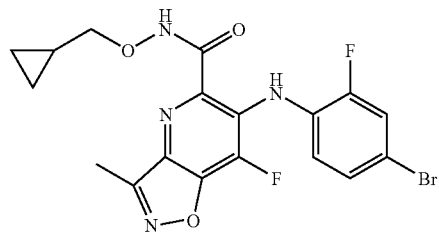

6-(4-Bromo-2-fluorophenylamino)-7-fluoro-3-methyl-isoxazolo[4,5-b]pyridine-5-carboxylic acid cyclopropylmethoxyamide Step A: Preparation of 3,4,5,6-tetrachloropyridine-2-carboxylic acid methyl ester: The title compound is prepared by the procedure previously described in Step F of Example 1.

Step B: Preparation of 3,5,6-trichloro-4-fluoropyridine-2-carboxylic acid methyl ester: To a solution of 3,4,5,6-tetrachloropyridine-2-carboxylic acid methyl ester (1.00 equivalent) in MeCN is added CsF (1.00 equivalent) at room temperature. The resulting mixture is refluxed with stirring for 16 hours. The reaction mixture is cooled to room temperature and diluted with EtOAc and water. The organic layer is washed with brine, dried over MgSO₄, filtered, and concentrated in vacuo to afford the desired product that is purified by flash column chromatography as necessary.

Step C: Preparation of 3,5,6-trichloro-4-fluoropyridine-2-carboxylic acid: The title compound is prepared by the procedure previously described in Step I of Example 1.

Step D: Preparation of 5,6-dichloro-4-fluoro-3-(2-fluorophenylamino)-pyridine-2-carboxylic acid: To a solution of 4-fluoroaniline (2.00 equivalents) in THF at −78° C. is added LiHMDS (3.00 equivalents, 1 M solution in THF). After complete addition, the resulting mixture is stirred for 1 hour at −78° C. A solution of 3,5,6-trichloro-4-fluoropyridine-2-carboxylic acid (1.00 equivalent) is added at −78° C. The reaction mixture is slowly warmed to room temperature and stirred for 16 hours. The reaction is quenched with 10% aqueous HCl at 0° C., acidified to pH 1, warmed to room temperature, and stirred for 1 hour. The precipitates are filtered, and washed with ether to yield the desired product that is directly used without further purification.

Step E: Preparation of 5,6-dichloro-4-fluoro-3-(2-fluorophenylamino)-pyridine-2-carboxylic acid methyl ester: The title compound is prepared by the procedure previously described in Step F of Example 1.

Step F: Preparation of 5-chloro-4-fluoro-3-(2-fluorophenylamino)-6-trimethylsilanylethynyl-pyridine-2-carboxylic acid methyl ester: A mixture of 5,6-dichloro-4-fluoro-3-(2-fluorophenylamino)-pyridine-2-carboxylic acid methyl ester (1.00 equivalent), TMS-acetylene (1.20 equivalents), Pd(PPh$_3$)$_2$Cl$_2$ (0.10 equivalents), CuI (0.10 equivalents), and i-Pr$_2$NH (2.00 equivalents) in THF is stirred for 16 hours at room temperature. THF is evaporated in vacuo. The reaction mixture is diluted with EtOAc and washed with saturated aqueous NH$_4$Cl and brine. The organic layer is dried over MgSO$_4$, filtered, and concentrated to give the crude material that is purified by flash column chromatography to afford the desired product.

Step G: Preparation of 6-acetyl-5-chloro-4-fluoro-3-(2-fluorophenylamino)-pyridine-2-carboxylic acid methyl ester: A mixture of 5-chloro-4-fluoro-3-(2-fluorophenylamino)-6-trimethylsilanylethynyl-pyridine-2-carboxylic acid methyl ester (1.00 equivalent), HgSO$_4$ (1.00 equivalent), and conc. H$_2$SO$_4$ (2.00 equivalents) in acetone-water is refluxed with stirring for 3 hours. The reaction mixture is concentrated in vacuo, diluted with EtOAc, and washed with water and brine. The organic layer is dried over MgSO$_4$, filtered, and concentrated in vauco to give the crude material that is purified by trituration or flash column chromatography to afford the desired product as necessary.

Step H: Preparation of 7-fluoro-6-(2-fluorophenylamino)-3-methyl-isoxazolo[4,5-b]pyridine-5-carboxylic acid methyl ester: To a solution of acetone oxime (2.20 equivalents) at room temperature is added t-BuOK (2.20 equivalents, 1.0 M solution in THF). After stirring for 30 minutes room temperature, the reaction mixture is cooled to 0° C. A solution 6-acetyl-5-chloro-4-fluoro-3-(2-fluorophenylamino)-pyridine-2-carboxylic acid methyl ester (1.00 equivalent) in THF is added. After stirring for 1 hour at 0-5° C., the reaction mixture is quenched with saturated aqueous NH$_4$Cl and diluted with EtOAc. The organic layer is washed with brine, dried over MgSO$_4$, concentrated in vacuo to give 6-acetyl-4-fluoro-3-(2-fluorophenylamino)-5-isopropylideneaminooxy-pyridine-2-carboxylic acid methyl ester that is used directly. A mixture of 6-acetyl-4-fluoro-3-(2-fluorophenylamino)-5-isopropylideneaminooxy-pyridine-2-carboxylic acid methyl ester in 5% aqueous MeOH is refluxed with stirring for 1 hour. The reaction mixture is diluted with EtOAc and washed with water. The organic layer is dried over MgSO$_4$, filtered, and concentrated in vacuo to give the crude material that is purified by flash column chromatography to afford the desired product.

Step I: Preparation of 6-(4-bromo-2-fluorophenylamino)-7-fluoro-3-methyl-isoxazolo[4,5-b]pyridine-5-carboxylic acid methyl ester: The title compound is prepared by the procedure previously described in Step H of Example 1.

Step J: Preparation of 6-(4-bromo-2-fluorophenylamino)-7-fluoro-3-methylisoxazolo[4,5-b]pyridine-5-carboxylic acid: The title compound is prepared by the procedure previously described in Step I of Example 1.

Step K: Preparation of 6-(4-bromo-2-fluorophenylamino)-7-fluoro-3-methylisoxazolo[4,5-b]pyridine-5-carboxylic acid cyclopropylmethoxyamide: The title compound is prepared using O-cyclopropylmethyl-hydroxylamine by the method previously described in Step J of Example 1.

Example 9

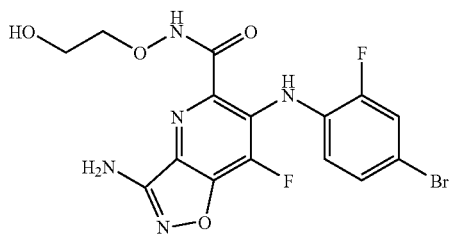

3-Amino-6-(4-bromo-2-fluorophenylamino)-7-fluoroisoxazolo[4,5-b]pyridine-5-carboxylic acid (2-hydroxyethoxy)-amide Step A: Preparation of 5-chloro-6-cyano-4-fluoro-3-(2-fluorophenylamino)-pyridine-2-carboxylic acid methyl ester: A mixture of 5,6-dichloro-4-fluoro-3-(2-fluorophenylamino)-pyridine-2-carboxylic acid methyl ester (1.00 equivalent) (prepared in Example 8), dppf (0.02 equivalents), Pd$_2$dba$_3$ (0.01 equivalents), and Zn(CN)$_2$ (0.60 equivalents) in NMP is stirred at 120° C. in a sealed tube. After stirring for 20 hours, the reaction mixture is cooled to room temperature and quenched with a 4:1:4 (volume) mixture solution of saturated aqueous NH$_4$Cl-conc NH$_4$OH-water. The mixture is extracted with EtOAc. The organic layer is washed with saturated aqueous NH$_4$Cl/conc. NH$_4$OH/water, and brine. The organic layer is dried over MgSO$_4$, filtered, and concentrated in vacuo to give the crude material that is purified by flash column chromatography to afford the desired product.

Step B: Preparation of 3-amino-7-fluoro-6-(2-fluorophenylamino)-isoxazolo[4,5-b]pyridine-5-carboxylic acid methyl ester: The title compound is prepared by a two step procedures as described in Step H of Example 8.

Step C: Preparation of 3-amino-6-(4-bromo-2-fluorophenylamino)-7-fluoroisoxazolo[4,5-b]pyridine-5-carboxylic acid methyl ester: The title compound is prepared by the method described in Step H of Example 1.

Step D: Preparation of 3-amino-6-(4-bromo-2-fluorophenylamino)-7-fluoroisoxazolo[4,5-b]pyridine-5-carboxylic acid: The title compound is prepared by the method described in step I of Example 1.

Step E: Preparation of 3-amino-6-(4-bromo-2-fluorophenylamino)-7-fluoroisoxazolo[4,5-b]pyridine-5-carboxylic acid (2-vinyloxyethoxy)-amide: The title compound is prepared using O-(2-vinyloxy-ethyl)-hydroxylamine by the method described in Step J of Example 1.

Step F: Preparation of 3-amino-6-(4-bromo-2-fluorophenylamino)-7-fluoroisoxazolo[4,5-b]pyridine-5-carboxylic acid (2-hydroxyethoxy)-amide: The title compound is prepared by the method described in Step K of Example 1.

Example 10

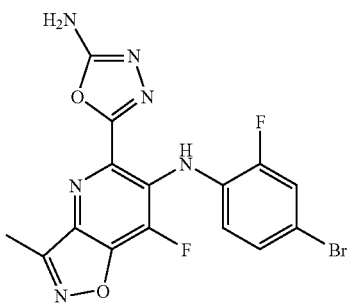

[5-(5-Amino-[1,3,4]oxadiazol-2-yl)-7-fluoro-3-methyl-isoxazolo[4,5-b]pyridin-6-yl]-(4-bromo-2-fluorophenyl)-amine The title compound is prepared using 6-(4-bromo-2-fluorophenylamino)-7-fluoro-3-methyl-isoxazolo[4,5-b]pyridine-5-carboxylic acid (prepared in Example 8) by the procedures previously described in Steps A and B of Example 2.

Example 11

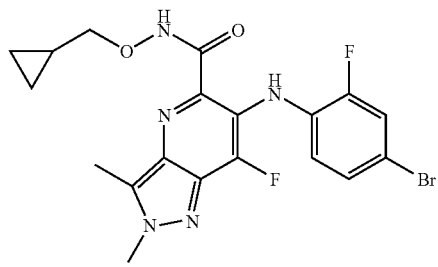

6-(4-Bromo-2-fluorophenylamino)-7-fluoro-2,3-dimethyl-2H-pyrazolo[4,3-b]pyridine-5-carboxylic acid cyclopropylmethoxyamide Step A: Preparation of 7-fluoro-6-(2-fluorophenylamino)-3-methyl-2H-pyrazolo[4,3-b]pyridine-5-carboxylic acid methyl ester: The title compound is prepared from 6-acetyl-5-chloro-4-fluoro-3-(2-fluorophenylamino)-pyridine-2-carboxylic acid methyl ester (prepared in Example 8) and the potassium salt of acetone hydrazone in place of the potassium salt of acetone oxime by the method previously described in step H of Example 8.

Step B: Preparation of 7-fluoro-6-(2-fluorophenylamino)-2,3-dimethyl-2H-pyrazolo[4,3-b]pyridine-5-carboxylic acid methyl ester: The title compound is prepared by the procedure previously described in Step D of Example 1.

Step C: Preparation of 6-(4-bromo-2-fluorophenylamino)-7-fluoro-2,3-dimethyl-2H-pyrazolo[4,3-b]pyridine-5-carboxylic acid methyl ester: The title compound is prepared by the procedure previously described in Step H of Example 1.

Step D: Preparation of 6-(4-bromo-2-fluorophenylamino)-7-fluoro-2,3-dimethyl-2H-pyrazolo[4,3-b]pyridine-5-carboxylic acid: The title compound is prepared by the procedure previously described in Step I of Example 1.

Step E: Preparation of 6-(4-bromo-2-fluorophenylamino)-7-fluoro-2,3-dimethyl-2H-pyrazolo[4,3-b]pyridine-5-carboxylic acid cyclopropylmethoxyamide: The title compound is prepared using O-cyclopropylmethyl-hydroxylamine by the procedure previously described in Step J of Example 1.

Example 12

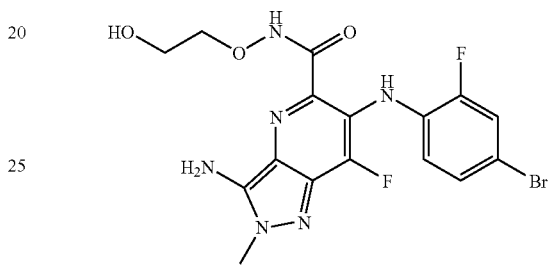

3-Amino-6-(4-bromo-2-fluorophenylamino)-7-fluoro-2-methyl-2H-pyrazolo[4,3-b]pyridine-5-carboxylic acid (2-hydroxyethoxy)-amide Step A: Preparation of 3-amino-7-fluoro-6-(2-fluorophenylamino)-2H-pyrazolo[4,3-b]pyridine-5-carboxylic acid methyl ester: The title compound is prepared from 5-chloro-6-cyano-4-fluoro-3-(2-fluorophenylamino)-pyridine-2-carboxylic acid methyl ester (prepared in Example 9) and the potassium salt of acetone hydrazone in place of the potassium salt of acetone oxime by the method previously described in step H of Example 8.

Step B: Preparation of 3-amino-7-fluoro-6-(2-fluorophenylamino)-2-methyl-2H-pyrazolo[4,3-b]pyridine-5-carboxylic acid methyl ester: The title compound is prepared by the procedure previously described in Step D of Example 1.

Step C: Preparation of 3-amino-6-(4-bromo-2-fluorophenylamino)-7-fluoro-2-methyl-2H-pyrazolo[4,3-b]pyridine-5-carboxylic acid methyl ester: The title compound is prepared by the method described in Step H of Example 1.

Step D: Preparation of 3-amino-6-(4-bromo-2-fluorophenylamino)-7-fluoro-2-methyl-2H-pyrazolo[4,3-b]pyridine-5-carboxylic acid: The title compound is prepared by the method described in Step I of Example 1.

Step E: Preparation of 3-amino-6-(4-bromo-2-fluorophenylamino)-7-fluoro-2-methyl-2H-pyrazolo[4,3-b]pyridine-5-carboxylic acid (2-vinyloxyethoxy)-amide: The title compound is prepared using O-(2-vinyloxy-ethyl)-hydroxylamine by the method described in Step J of Example 1.

Step F: Preparation of 3-amino-6-(4-bromo-2-fluorophenylamino)-7-fluoro-2-methyl-2H-pyrazolo[4,3-b]pyridine-5-carboxylic acid (2-hydroxyethoxy)-amide: The title compound is prepared by the method described in Step K of Example 1.

Example 13

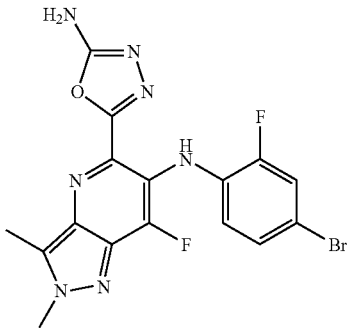

[5-(5-Amino-[1,3,4]oxadiazol-2-yl)-7-fluoro-2,3-dimethyl-2H-pyrazolo[4,3-b]pyridin-6-yl]-(4-bromo-2-fluorophenyl)-amine The title compound is prepared using 6-(4-bromo-2-fluorophenylamino)-7-fluoro-2,3-dimethyl-2H-pyrazolo[4,3-b]pyridine-5-carboxylic acid (prepared in Example 11) by the methods previously described in Steps A and B of Example 2.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound having the Formula:

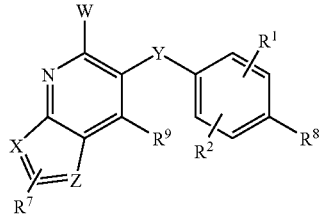

and pharmaceutically acceptable salts and prodrugs thereof, where

X is N;
Y is $NR^{15}$, O, S, S(O), S(O)$_2$, C(O) or CH$_2$;
Z is N;

$R^1$, $R^2$, $R^8$, and $R^9$ are independently hydrogen, hydroxy, halogen, cyano, nitro, trifluoromethyl, difluoromethyl, fluoromethyl, fluoromethoxy, difluoromethoxy, trifluoromethoxy, azido, —$SR^{11}$, —$OR^3$, —$C(O)R^3$, —$C(O)OR^3$, —$NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^7$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, or heterocyclylalkyl, wherein any of said alkyl, alkenyl, alkynyl, cycloalkyl, aryl, arylalkyl, heteroaryl, heteroarylalkyl, heterocyclyl and heterocyclylalkyl are optionally substituted with one or more groups independently selected from oxo (with the proviso that it is not substituted on an aryl or heteroaryl), halogen, cyano, nitro, trifluoromethyl, difluoromethyl, fluoromethyl, fluoromethoxy, difluoromethoxy, trifluoromethoxy, azido, —$NR^{11}SO_2R^{14}$, —$SO_2NR^{11}R^{12}$, —$C(O)R^{11}$, $C(O)OR^{11}$, —$OC(O)R^{11}$, —$NR^{11}C(O)OR^{14}$, —$NR^{11}C(O)R^{12}$, —$C(O)NR^{11}R^{12}$, —$SR^{11}$, —$S(O)R^{14}$, —$SO_2R^{14}$, —$NR^{11}R^{12}$, —$NR^{11}C(O)NR^{12}R^{13}$, —$NR^{11}C(NCN)NR^{12}R^{13}$, —$OR^{11}$, $C_1$-$C_{10}$ alkyl, $C_2$-$C_{10}$ alkenyl, $C_2$-$C_{10}$ alkynyl, $C_3$-$C_{10}$ cycloalkyl, aryl, heteroaryl, arylalkyl, heteroarylalkyl, heterocyclyl, and heterocyclylalkyl, and wherein said cycloalkyl, heterocycloalkyl, aryl or heteroaryl rings may be further substituted with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, aryl, arylalkyl, heteroaryl, heteroarylalkyl, heterocyclyl and heterocyclylalkyl are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

or R$^3$ and R$^4$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^4$ and R$^5$ independently are hydrogen or C$_1$-C$_6$ alkyl, or R$^4$ and R$^5$ together with the atom to which they are attached form a 4 to 10 membered carbocyclic, heteroaryl or heterocyclic ring, wherein said alkyl or any of said carbocyclic, heteroaryl and heterocyclic rings are optionally substituted with one or more groups independently selected from halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^6$ is trifluoromethyl, C$_1$-C$_{10}$ alkyl, C$_3$-C$_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl are optionally substituted with one or more groups independently selected from oxo (with the proviso that it is not substituted on an aryl or heteroaryl), halogen, cyano, nitro, trifluoromethyl, difluoromethoxy, trifluoromethoxy, azido, —NR$^{11}$SO$_2$R$^{14}$, —SO$_2$NR$^{11}$R$^{12}$, —C(O)R$^{11}$, C(O)OR$^{11}$, —OC(O)R$^{11}$, —NR$^{11}$C(O)OR$^{14}$, —NR$^{11}$C(O)R$^{12}$, —C(O)NR$^{11}$R$^{12}$, —SR$^{11}$, —S(O)R$^{14}$, —SO$_2$R$^{14}$, —NR$^{11}$R$^{12}$, —NR$^{11}$C(O)NR$^{12}$R$^{13}$, —NR$^{11}$C(NCN)NR$^{12}$R$^{13}$, —OR$^{11}$, aryl, heteroaryl, arylalkyl, heteroarylalkyl, heterocyclyl, and heterocyclylalkyl;

R$^{11}$, R$^{12}$ and R$^{13}$ independently are hydrogen, lower alkyl, lower alkenyl, aryl or arylalkyl, and R$^{14}$ is lower alkyl, lower alkenyl, aryl or arylalkyl;

or any two of R$^{11}$, R$^{12}$, R$^{13}$ or R$^{14}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) or CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)NR$^4$SO$_2$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl) and CR$^3$OR$^3$ are optionally substituted with one or more groups independently selected from halogen, cyano, nitro, azido, —NR$^3$R$^4$, —OR$^3$, C$_1$-C$_{10}$ alkyl, C$_2$-C$_{10}$ alkenyl, C$_2$-C$_{10}$ alkynyl, cycloalkyl and heterocycloalkyl, wherein any of said C$_1$-C$_{10}$ alkyl, C$_2$-C$_{10}$ alkenyl, C$_2$-C$_{10}$ alkynyl, cycloalkyl and heterocycloalkyl are optionally substituted with 1 or more groups independently selected from —NR$^3$R$^4$ and —OR$^3$;

R$^{15}$ is hydrogen, halogen, methyl, fluoromethyl, difluoromethyl, trifluoromethyl or ethyl;

m is 0, 1, 2, 3, 4 or 5; and j is 0, 1 or 2.

2. The compound of claim 1, where Y is NH.

3. The compound of claim 2, where R$^9$ is hydrogen, halogen, methyl, fluoromethyl, difluoromethyl, trifluoromethyl or ethyl.

4. The compound of claim 3, where W is selected from heteroaryl, C(O)OR$^3$, C(O)NR$^3$R$^4$, C(O)NR$^4$OR$^3$ and C(O)NR$^4$S(O)$_2$R$^3$, wherein any of said heteroaryl, C(O)OR$^3$, C(O)NR$^3$R$^4$, C(O)NR$^4$OR$^3$ or C(O)NR$^4$S(O)$_2$R$^3$ are optionally substituted with one or more groups selected from halogen, hydroxyl, cyano, nitro, azido, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethoxy, C$_1$-C$_4$ alkyl, C$_2$-C$_4$ alkenyl, C$_2$-C$_4$ alkynyl, C$_3$-C$_6$ cycloalkyl and C$_3$-C$_6$ heterocycloalkyl, wherein any of said C$_1$-C$_4$ alkyl, C$_2$-C$_4$ alkenyl, C$_2$-C$_4$ alkynyl, cycloalkyl or heterocycloalkyl can be further optionally substituted with one or more groups selected from NR$^3$R$^4$ and OR$^3$.

5. The compound of claim 3, where W is selected from C(O)OR$^3$, C(O)NHR$^3$, and C(O)NHOR$^3$, wherein any of said C(O)OR$^3$, C(O)NHR$^3$, and C(O)NHOR$^3$ are optionally substituted with one or more groups selected from halogen, hydroxyl, cyano, nitro, azido, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethoxy, C$_1$-C$_4$ alkyl, C$_2$-C$_4$ alkenyl, C$_2$-C$_4$ alkynyl, C$_3$-C$_6$ cycloalkyl and C$_3$-C$_6$ heterocycloalkyl, wherein any of said C$_1$-C$_4$ alkyl, C$_2$-C$_4$ alkenyl, C$_2$-C$_4$ alkynyl, cycloalkyl or heterocycloalkyl can be further optionally substituted with one or more groups selected from NR$^3$R$^4$ and OR$^3$; and R$^3$ is selected from hydrogen, C$_1$-C$_4$ alkyl, C$_2$-C$_4$ alkenyl, C$_2$-C$_4$ alkynyl, C$_3$-C$_6$ cycloalkyl and C$_3$-C$_6$ heterocycloalkyl, wherein any of said C$_1$-C$_4$ alkyl, C$_2$-C$_4$ alkenyl, C$_2$-C$_4$ alkynyl, cycloalkyl or heterocycloalkyl are optionally substituted with one or more groups selected from NR$^3$R$^4$ and OR$^3$.

6. The compound of claim 5, where R$^7$ is C$_1$-C$_4$ alkyl, C$_2$-C$_4$ alkenyl or C$_2$-C$_4$ alkynyl, wherein said C$_1$-C$_4$ alkyl, C$_2$-C$_4$ alkenyl and C$_2$-C$_4$ alkynyl, may be optionally substituted with one or more groups selected from halogen, hydroxyl, cyano, nitro, azido, fluoromethyl, difluoromethyl, trifluoromethyl, methoxy, fluoromethoxy, difluoromethoxy, amino, aminomethyl, dimethylamino, aminoethyl, diethylamino, ethoxy, cycloalkyl, heterocycloalkyl, aryl and heteroaryl, wherein said cycloalkyl, heterocycloalkyl, aryl or heteroaryl rings may be optionally substituted with one or more groups selected from halogen, hydroxyl, cyano, nitro, azido, fluoromethyl, difluoromethyl, trifluoromethyl, C$_1$-C$_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$.

7. The compound of claim 6, where $R^1$ and $R^2$ are independently hydrogen, halogen, methyl, fluoromethyl, difluoromethyl, trifluoromethyl or ethyl; and $R^8$ is halogen, hydroxyl, cyano, nitro, azido, methyl, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethyl, ethoxy or $SR^{11}$.

8. The compound of claim 7, where $R^1$ is halogen or methyl, $R^2$ is hydrogen and $R^8$ is hydrogen, halogen, methyl, fluoromethyl, difluoromethyl, trifluoromethyl or $SR^{11}$.

9. The compound of claim 8, where $R^1$ is halogen, $R^8$ is halogen, $R^9$ is alkyl or halogen, and $R^2$ is in the position adjacent to Y, where $R^2$ is hydrogen.

10. The compound of claim 3, where W is selected from

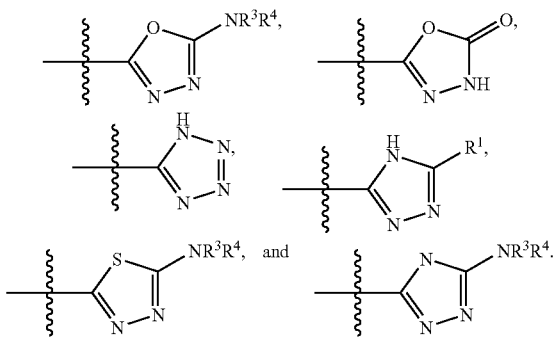

11. The compound of claim 10, where $R^7$ is $C_1$-$C_4$ alkyl, $C_2$-$C_4$ alkenyl or $C_2$-$C_4$ alkynyl, wherein said $C_1$-$C_4$ alkyl, $C_2$-$C_4$ alkenyl and $C_2$-$C_4$ alkynyl may be optionally substituted with one or more groups selected from halogen, hydroxyl, cyano, nitro, azido, fluoromethyl, difluoromethyl, trifluoromethyl, methoxy, fluoromethoxy, difluoromethoxy, amino, aminomethyl, dimethylamino, aminoethyl, diethylamino, ethoxy, cycloalkyl, heterocycloalkyl, aryl or heteroaryl, wherein said cycloalkyl, heterocycloalkyl, aryl or heteroaryl rings may be optionally substituted with one or more groups selected from halogen, hydroxyl, cyano, nitro, azido, fluoromethyl, difluoromethyl, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, $NR^3R^4$ and $OR^3$.

12. The compound of claim 11, where $R^1$ and $R^2$ are independently hydrogen, halogen, methyl, fluoromethyl, difluoromethyl, trifluoromethyl or ethyl; and $R^8$ is halogen, hydroxyl, cyano, nitro, azido, methyl, fluoromethyl, difluoromethyl, trifluoromethyl, methoxy, fluoromethoxy, difluoromethoxy, trifluoromethoxy, amino, aminomethyl, dimethylamino, aminoethyl, diethylamino, ethyl, ethoxy or $SR^{11}$.

13. The compound of claim 12, where $R^1$ is halogen or methyl, $R^2$ is hydrogen and $R^8$ is hydrogen, halogen, methyl, fluoromethyl, difluoromethyl, trifluoromethyl or $SR^{11}$.

14. The compound of claim 13, where $R^1$ is halogen, $R^2$ is hydrogen, $R^8$ is halogen, $R^9$ is alkyl or halogen, and $R^2$ is in the position adjacent to Y, where $R^2$ is hydrogen.

15. A composition comprising a compound of claim 1 and a pharmaceutically acceptable carrier.

16. A composition comprising a compound of claim 5 and a pharmaceutically acceptable carrier.

17. A composition comprising a compound of claim 10 and a pharmaceutically acceptable carrier.

18. A method for preparing a compound of formula 7

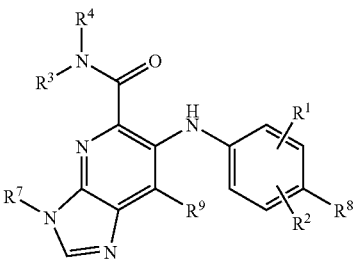

wherein
$R^1$, $R^2$ and $R^9$ are independently hydrogen, halogen, methyl, fluoromethyl, difluoromethyl, trifluoromethyl or ethyl;
$R^4$ is hydrogen or $C_1$-$C_6$ alkyl;
$R^3$ and $R^7$ are independently alkyl, alkenyl, alkynyl, cycloalkyl, heterocycloalkyl, aryl or heteroaryl, wherein said alkyl, alkenyl, alkynyl, cycloalkyl, heterocycloalkyl, aryl or heteroaryl may be optionally substituted with one or more groups selected from halogen, hydroxyl, cyano, nitro, amino, azido, fluoromethyl, difluoromethyl, trifluoromethyl, methoxy, fluoromethoxy, difluoromethoxy, amino, aminomethyl, dimethylamino, aminoethyl, diethylamino, ethoxy, cycloalkyl, heterocycloalkyl, aryl or heteroaryl; and
$R^8$ is halogen, hydroxyl, cyano, nitro, azido, methyl, fluoromethyl, difluoromethyl, trifluoromethyl, methoxy, fluoromethoxy, difluoromethoxy, trifluoromethoxy, amino, aminomethyl, dimethylamino, aminoethyl, diethylamino, $SR^1$, ethyl, or ethoxy;
said method comprising:
(a) reacting a compound of formula 5

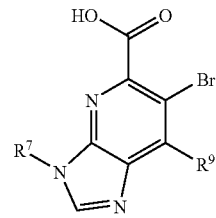

with an aniline derivative to provide a compound of formula 6

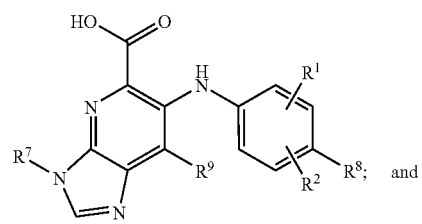

(b) reacting a compound of formula 6 with an amine to provide a compound of formula 7.

* * * * *